United States Patent [19]
Otten et al.

[11] Patent Number: 6,013,607
[45] Date of Patent: Jan. 11, 2000

[54] 2-HETAROYLCYCLOHEXANE-1,3-DIONES

[75] Inventors: Martina Otten, Ludwigshafen; Wolfgang von Deyn, Neustadt; Stefan Engel, Idstein; Regina Luise Hill, Speyer; Uwe Kardorff; Marcus Vossen, both of Mannheim; Peter Plath, Frankenthal; Helmut Walter, Obrigheim; Karl-Otto Westphalen, Speyer; Ulf Misslitz, Neustadt, all of Germany

[73] Assignee: BASF Aktiengesellschaft, Ludwigshafen, Germany

[21] Appl. No.: 09/125,378

[22] PCT Filed: Feb. 20, 1997

[86] PCT No.: PCT/EP97/00802

§ 371 Date: Aug. 17, 1998

§ 102(e) Date: Aug. 17, 1998

[87] PCT Pub. No.: WO97/30986

PCT Pub. Date: Aug. 28, 1997

[30] Foreign Application Priority Data

Feb. 24, 1996 [DE] Germany .............. 196 07 105
Mar. 29, 1996 [DE] Germany .............. 196 12 687

[51] Int. Cl.[7] .................. A01N 43/24; C07D 327/08; C07D 339/08
[52] U.S. Cl. ........................... 504/288; 549/15
[58] Field of Search ............... 504/288; 549/15

[56] References Cited

U.S. PATENT DOCUMENTS

| | | | |
|---|---|---|---|
| 4,249,937 | 2/1981 | Iwataki et al. | 71/97 |
| 4,780,127 | 10/1988 | Michaely et al. | 71/103 |
| 4,909,835 | 3/1990 | Tobler | 71/103 |
| 5,468,878 | 11/1995 | Nasuno et al. | 549/23 |
| 5,468,905 | 11/1995 | Suzuki et al. | 568/346 |
| 5,480,858 | 1/1996 | Sakamoto et al. | 504/288 |

FOREIGN PATENT DOCUMENTS 186 118  7/1986  European Pat. Off. .
283 261  9/1988  European Pat. Off. .

OTHER PUBLICATIONS

J. Org. Chem., vol. 39, Apr. 5, 1974, No. 7, 1811–1814.
Chem. Abst. vol. 126, No. 2, Abst. No. 18883v, S.542.
J. Am. Chem. Soc., vol. LXXVI, Jan.–Mar. 1954, 1068–1074.
J. Org. Chem., vol. 44, No. 12, 1979, 1977–1981.
J. Heterocyclic Chem., 20, 823 (1983), 867–870.
Japanese Abstr. JP8245618–A.
Synthesis, Jul. 1975, 451–452.

*Primary Examiner*—Amelia Owens
*Attorney, Agent, or Firm*—Keil & Weinkauf

[57] ABSTRACT

Hetaroyl derivatives of the formula I

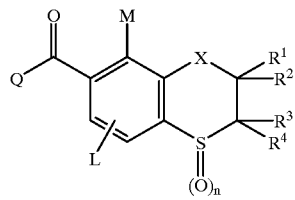

where the substituents have the following meanings:

L and M hydrogen, $C_1$–$C_6$-alkyl, $C_2$–$C_6$-alkenyl, $C_2$–$C_6$-alkynyl, $C_1$–$C_4$-alkoxy, it being possible for these groups to be unsubstituted or substituted by one to five halogen atoms or $C_1$–$C_4$-alkoxy; halogen, cyano, nitro;

X oxygen or sulfur which can be substituted by one or two oxygens;

n zero, one, two;

Q,$R^1$,$R^2$,$R^3$ and $R^4$ have the meanings given in claim 1, processes for preparing the hetaroyl derivatives, compositions which contain them and the use of these derivatives or compositions containing them for controlling weeds are described.

13 Claims, No Drawings

2-HETAROYLCYCLOHEXANE-1,3-DIONES

This application is a 371 of PCT/EP97/00802 filed Feb. 20, 1997.

The present invention-relates to novel hetaroyl derivatives having herbicidal activity, processes for preparing the hetaroyl derivatives, compositions which contain them and the use of these derivatives or compositions containing them for controlling weeds.

The literature discloses herbicidally active 2-hetaroylcylohexadiones, for example in WO 948988, WO 9404524 and EP 283261.

The herbicidal properties of the known compounds and the tolerability to crop plants can only be satisfactory, however, to a limited extent.

It is an object of the present invention to find novel 2-hetaroylcyclohexanediones having improved properties.

We have found that this object is achieved by the hetaroyl derivatives of the formula I

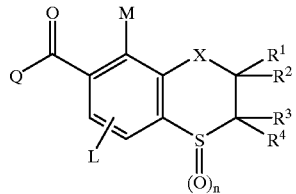

where the substituents have the following meanings:

L and M hydrogen, $C_1$–$C_6$-alkyl, $C_2$–$C_6$-alkenyl, $C_2$–$C_6$-alkynyl, $C_1$–$C_4$-alkoxy, it being possible for these groups to be unsubstituted or substituted by one to five halogen atoms or $C_1$–$C_4$-alkoxy; halogen, cyano, nitro;

X oxygen or sulfur which can be substituted by one or two oxygens;

n zero, one, two;

$R^1$ hydrogen, $C_1$–$C_6$-alkyl, $C_2$–$C_6$-alkenyl, $C_2$–$C_6$-alkynyl, $C_1$–$C_4$-alkoxy [sic], it being possible for these groups to be unsubstituted or substituted by one to five halogen atoms or $C_1$–$C_4$-alkoxy; halogen;

phenyl which can be monosubstituted or polysubstituted by the following groups: $C_1$–$C_4$-alkyl, hydrogen, $C_1$–$C_4$-alkoxy, $C_1$–$C_4$-haloalkyl, $C_1$–$C_4$-haloalkoxy, halogen, nitro, cyano, $C_1$–$C_4$-alkyloxycarbonyl;

$R^2$ hydrogen, $C_1$–$C_6$-alkyl, $C_2$–$C_6$-alkenyl, $C_2$–$C_6$-alkynyl, $C_1$–$C_4$-alkoxy, it being possible for these groups to be unsubstituted or substituted by one to five halogen atoms or $C_1$–$C_4$-alkoxy; halogen;

phenyl which can be monosubstituted or polysubstituted by the following groups: $C_1$–$C_4$-alkyl, hydrogen, $C_1$–$C_4$-alkoxy, $C_1$–$C_4$-haloalkyl, $C_1$–$C_4$-haloalkoxy, halogen, nitro, cyano, $C_1$–$C_4$-alkyloxycarbonyl; $R^3$ and $R^2$ can form a bond;

$R^3$ hydrogen, $C_1$–$C_6$-alkyl, $C_2$–$C_6$-alkenyl, $C_2$–$C_6$-alkynyl, $C_1$–$C_4$-alkoxy, it being possible for these groups to be unsubstituted or substituted by one to five halogen atoms or $C_1$–$C_4$-alkoxy; halogen;

phenyl which can be monosubstituted or polysubstituted by the following groups: $C_1$–$C_4$-alkyl, hydrogen, $C_1$–$C_4$-alkoxy, $C_1$–$C_4$-haloalkyl, $C_1$–$C_4$-haloalkoxy, halogen, nitro, cyano, $C_1$–$C_4$-alkyloxycarbonyl; $R^3$ and $R^2$ can form a bond;

$R^4$ hydrogen, $C_1$–$C_6$-alkyl, $C_2$–$C_6$-alkenyl, $C_2$–$C_6$-alkynyl, $C_1C_4$-alkoxy, it being possible for these groups to be unsubstituted or substituted by one to five halogen atoms or $C_1$–$C_4$-alkoxy; halogen;

phenyl which can be monosubstituted or polysubstituted by the following groups: $C_1$–$C_4$-alkyl, hydrogen, $C_1$–$C_4$-alkoxy, $C_1$–$C_4$-haloalkyl, $C_1$–$C_4$-haloalkoxy, halogen, nitro, cyano, $C_1$–$C_4$-alkyloxycarbonyl;

Q a cyclohexane-1,3-dione ring, linked in the 2-position, of the formula II

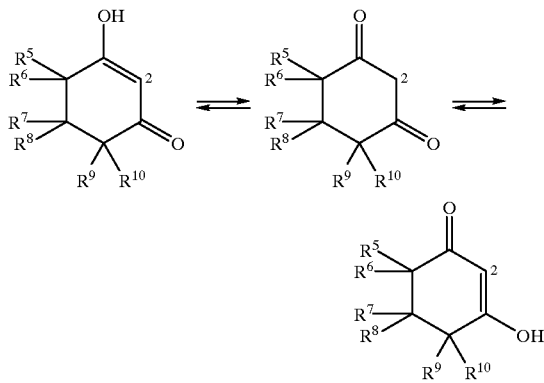

where the substituents have the following meanings:

$R^5$, $R^6$ and $R^{10}$ hydrogen, $C_1$–$C_4$-alkyl;

$R^7$ hydrogen, $C_1$–$C_4$-alkyl, $C_3$–$C_4$-cycloalkyl, it being possible for these groups, if desired, to carry one to three of the following substituents: halogen, $C_1$–$C_4$-thioalkyl or $C_1$–$C_4$-alkoxy; or $C_1$–$C_4$-alkoxy; $C_1$–$C_6$-alkoxyalkyl, tetrahydropyran-3-yl, tetrahydropyran-4-yl; or $R^7$ and $R^9$ can together form a bond or a three- to six-membered carbocyclic ring;

$R^8$ hydrogen, $C_1$–$C_4$-alkyl;

$R^9$ hydrogen, $C_1$–$C_4$-alkyl or a group $COOR^{11}$;

$R^{11}$ $C_1$–$C_4$-alkyl;

and agriculturally utilizable salts.

Compounds of the formula I are obtained by reacting compounds of the formula II with a benzoic acid derivative of the formula III and rearranging them to give hetaroyl derivatives of the formula I.

Scheme 1

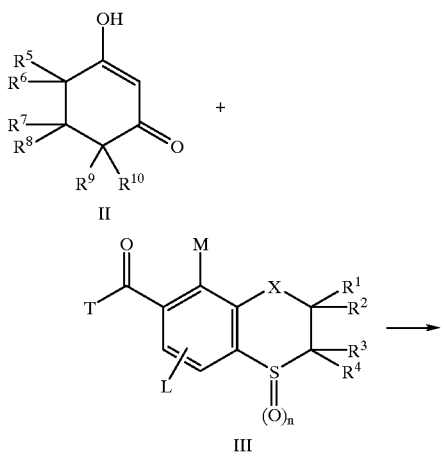

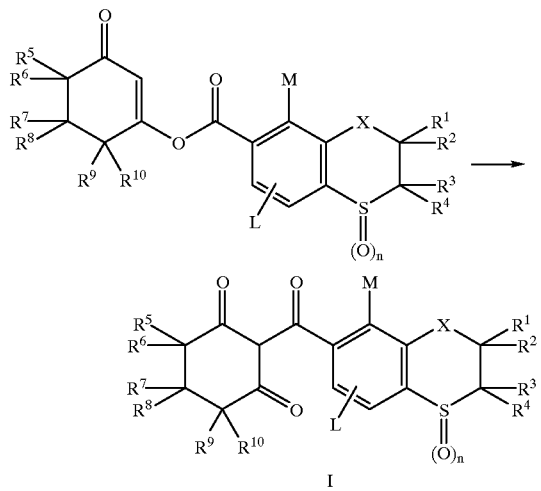

In the above scheme 1, T in the formulae mentioned has the meaning halogen or OH and L, M, X, $R^1$, $R^2$, $R^3$, $R^4$ and n have the meanings given above.

The first step of the reaction sequence, the acylation, is carried out in a generally known manner, eg. by addition of an acid chloride of the formula III (T=Cl) or of a carboxylic acid III T(=OH) activated, for example, with DCC (dicyclocarbodiimides or similar agents known from the literature, eg. triphenylphosphine/DEAD=diethyl azodicarboxylate, 2-pyridine disulfide/triphenylphosphine to the solution or suspension of a cyclohexanedione II, if appropriate in the presence of an auxiliary base. The reactants and the auxiliary base are in this case expediently employed in equimolar amounts. A small excess, eg. from 1.2 to 1.5 mol equivalents, based on II, of the auxiliary base can be advantageous under certain circumstances.

Suitable auxiliary bases are tertiary alkylamines, pyridine or alkali metal carbonates. The solvents used can be, for example, methylene chloride, dioxane, diethyl ether, toluene, acetonitrile or ethyl acetate.

During the addition of the acid chloride, the reaction mixture is preferably cooled to from 0 to 10° C., and it is then stirred at from 20 to 100° C., in particular 25 to 50° C., until the reaction is complete. Working-up is carried out in the customary manner, eg. the reaction mixture is poured into water and the useful product is extracted, eg. with methylene chloride. After drying of the organic phase and removal of the solvent, the crude enol ester can be employed for the rearrangement without further purification. Preparation examples for benzoyl enol esters of cyclohexane-1,3-diones are found, for example, in EP-A 186118 or U.S. Pat. No. 4,780,127.

The rearrangement of the enol esters to the compounds of the formula Ia–Ie is expediently carried out at from 20 to 40° C. in a solvent and in the presence of an auxiliary base, and with the aid of a cyano compound as a catalyst.

The solvents used can be, for example, acetonitrile, methylene chloride, 1,2-dichloroethane, ethyl acetate or toluene. A preferred solvent is acetonitrile. Suitable auxiliary bases are tertiary alkylamines, pyridine or alkali metal carbonates, which are preferably employed in an equimolar amount or up to a four-fold excess, based on the benzoyl enol ester. A preferred auxiliary base is triethylamine in twice the amount.

Suitable catalysts are potassium cyanide, acetone cyanohydrin and trimethylsilyl cyanide, preferably in an amount of from 1 to 50 mol percent, based on the enol ester. Acetone cyanohydrin is preferably added, eg. in an amount of from 5 to 15, in particular 10, mol percent. Examples of cyanide-catalyzed rearrangement of enol esters are found, for example, in EP-A 186118 or U.S. Pat. No. 4,780,127.

Working-up is carried out in a manner known per se, eg. the reaction mixture is acidified with dilute mineral acids such as 5% strength hydrochloric acid or sulfuric acid and extracted with an organic solvent such as methylene chloride or ethyl acetate. For purification, the extract is extracted with cold 5 to 10% strength alkali metal carbonate solution, the final product passing into the aqueous phase. By acidifying the aqueous solution, the product of the formula Ia-Ie is precipitated or again extracted with methylene chloride or ethyl acetate, dried and then freed from the solvent.

The 1,3-diketones of the formula II used as starting material are known and can be prepared by methods known per se, such as are described, for example, in EP-A 71707, EP-A 142741, EP-A 243313, U.S. Pat. No. 4,249,937 and WO 92/13821. Cyclohexanedione and dimedone are commercially available compounds.

Benzoic acid derivatives of the formula III can be prepared in the following manner:

Benzoyl halides such as, for example, benzoyl chlorides of the formula III (T=Cl) are prepared in a manner known per se by reaction of the benzoic acids of the formula III (T=OH) with thionyl chloride.

The benzoic acids of the formula III (T=OH) can be prepared from the corresponding esters of the formula III (T=$C_1$–$C_4$-alkoxy) in a known manner by acidic or basic hydrolysis.

The intermediates of the formula III can be prepared starting from compounds which are in some cases known from the literature, such as substituted phenolcarboxylic acids IV or thiocarboxylic acids V. Unknown compounds IV or V can be synthesized by use of reactions known from the literature (ref.: Houben Weyl, Methoden der Organischen Chemie [Methods of Organic Chemistry] Volume VI, IX and E11).

Further reaction to give the intermediates of the formula III proceeds via processes known from the literature (eg. Synthesis 1975, 451; J. Org. Chem. 1974, 39–1811; J. Am. Chem. Soc. 1954, 76, 1068; Heterocyclic Compounds, Volume: Multi-Sulfur and Sulfur and Oxygen Five and Six-Membered Heterocycles; J. Org. Chem. 1979, 44, 1977).

Scheme 2
A)
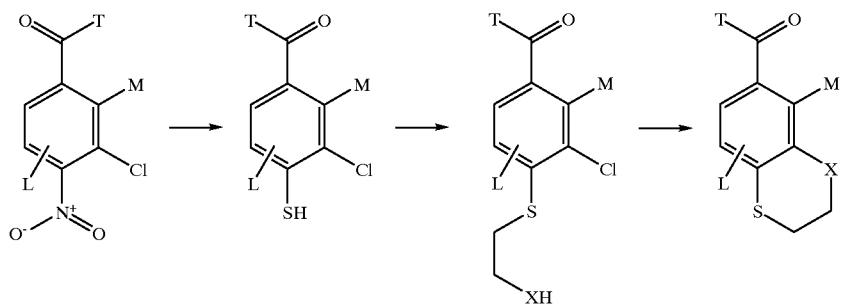
or
B)
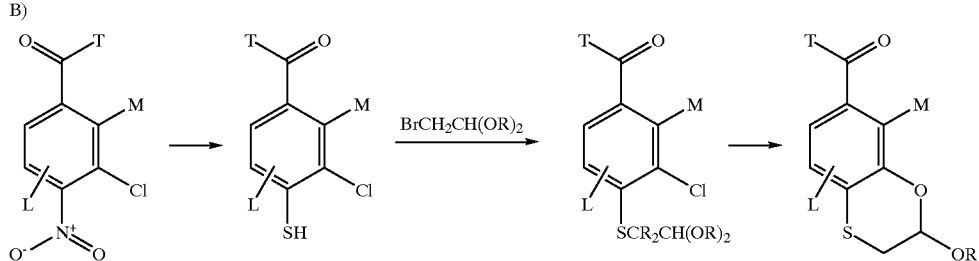
or
C)
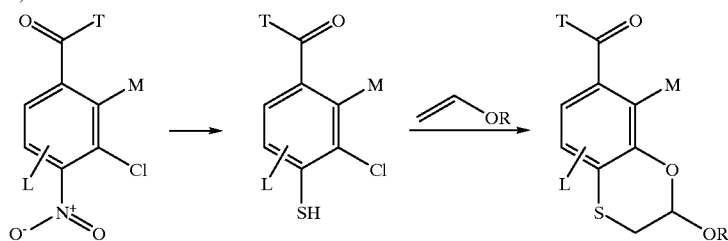
D)
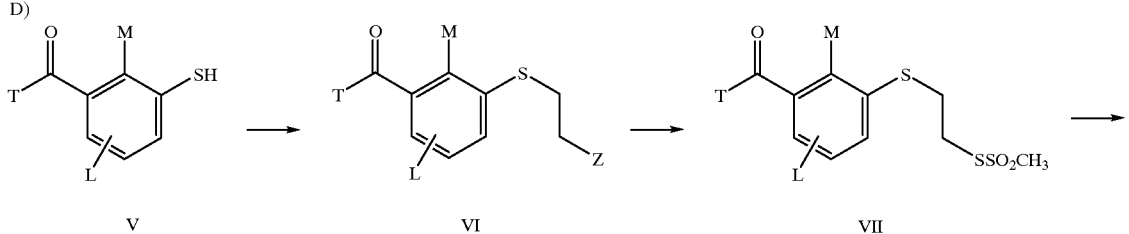
(Z = Br, OH, OSO$_2$CH$_3$, OSO$_2$p-CH$_3$—C$_6$H$_4$)

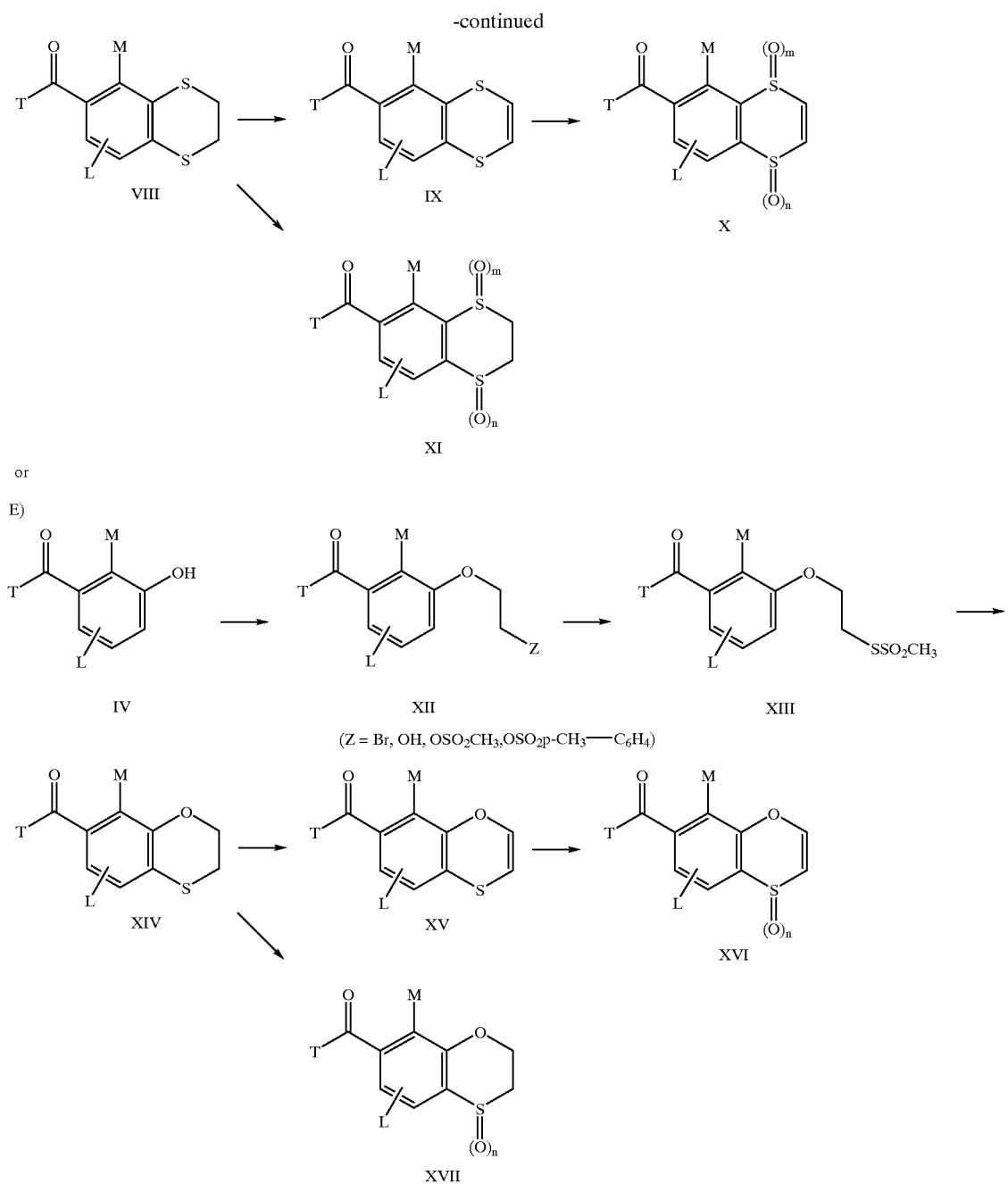

2,3-Dihydrobenz-1,4-oxathiin derivatives can then be synthesized, for example, as shown in Scheme 2A, by intermolecular nucleophilic substitution on the aromatic compound (X=O,S; T=OH, $C_1$–$C_4$-alkoxy) (Lit: J. Heterocycl. Chem. 20, 1983, 867). Routes B and C describe the route specified in the literature to 2-alkoxy-2,3-dihydrobenz-1,4-oxathiin derivatives (Lit: J. Am. Chem. Soc. 76, 1954, 1068; J. Org. Chem. 44, 1979, 1977). Phenols or thiols can be alkylated with alkyl bromides in alkaline solution as shown in scheme 2 in D and E. The reactants and the base are in this case expediently employed in equimolar amounts. An excess of base may be advantageous. Preferred solvents are alcohols such as ethanol or DMF and preferred bases are alkoxides such as, for example, sodium methoxide or, for example, NaH. The reaction can be carried out under normal pressure or at elevated pressure. The preferred pressure range is from 1 to 10 bar. The reaction mixture is preferably stirred at 20–150° C., in particular at 60–80° C. Working-up is carried out, for example, by pouring the reaction mixture onto dilute alkali solution such as sodium hydroxide solution and the useful product can be obtained by extraction with, for example, ethyl acetate, dried and freed from the solvent.

Then, for example, a replacement of Z with potassium methanethiosulfonate in alcoholic solution can be carried out. Preferred solvents are ethanol, methanol and isopropanol. The reaction mixture is in this case preferably stirred at 20–100° C., in particular at 60–80° C.

Working-up is carried out, for example, by addition of water, the useful product being filtered off with suction or extracted by extraction with, for example, methylene chloride and dried.

Cyclization to give the dihydrobenzoxathiin or dihydrobenzodithiin structure is carried out with addition of a Lewis acid in an inert solvent. In this connection, aluminum trichloride is preferred as the Lewis acid and nitromethane or methylene chloride as the inert solvent. The reaction mixture is kept at 20–50° C. Working-up is carried out, for example, by addition of dilute mineral acid such as hydrochloric acid and the useful product is filtered off with suction or extracted by extraction with ether, dried and freed from the solvent.

By oxidation according to methods known from the literature and/or dehydrogenation (Houben Weyl Methoden der Organischen Synthese Volume IV/1a and b), the compounds can be further functionalized.

The benzoic acids of the formula III can also be obtained by reacting the corresponding bromo- or iodo-substituted compounds of the formula XVIII

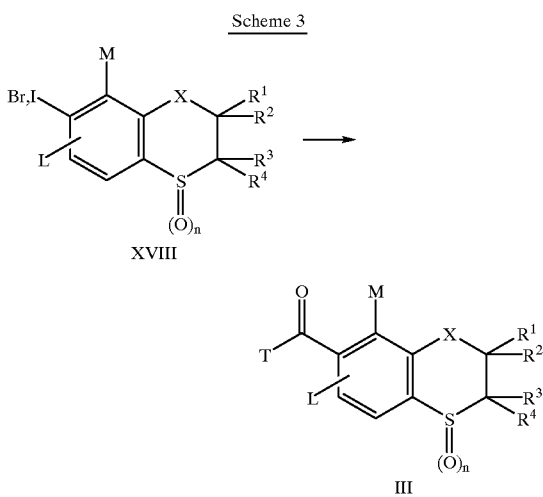

Scheme 3 where
T is OH, $C_1$–$C_4$-alkoxy; and
L, M, X, $R^1$ to $R^4$ and n have the meanings described above; with carbon monoxide and water at elevated pressure in the presence of a palladium, nickel, cobalt or rhodium transition metal catalyst and of a base.

The catalysts nickel, cobalt, rhodium and in particular palladium can be present in metallic form or in the form of customary salts such as in the form of halogen compounds, eg. $PdCl_2$, $RhCl_3.H_2O$, acetates, eg. $Pd(OAc)_2$, cyanides etc., in the known valency states. Metal complexes with tertiary phosphines, metal alkylcarbonyls, metal carbonyls, eg. $CO_2(CO)_8$, $Ni(CO)_4$, metal carbonyl complexes with tertiary phosphines, eg. $(PPh_3)_2Ni(CO)_2$, or transition metal salts complexed with tertiary phosphines can also be present. The last-mentioned embodiment is preferred in particular in the case of palladium as a catalyst. In this connection, the nature of the phosphine ligands is widely variable. For example, they can be represented by the following formulae:

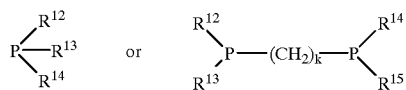

where k is the numbers 1, 2, 3 or 4 and the radicals $R^{12}$ to $R^{15}$ are low-molecular-weight alkyl, eg. $C_1$–$C_6$-alkyl, aryl, $C_1$–$C_4$-alkylaryl, eg. benzyl, phenethyl or aryloxy. Aryl is, for example, naphthyl, anthryl and preferably unsubstituted or substituted phenyl, where, with respect to the substituents, attention has to be paid only to their inertness to the carboxylation reaction, otherwise they can be widely varied and include all inert organocarbon radicals such as $C_1$–$C_6$-alkyl radicals, eg. methyl, carboxyl radicals such as COOH, COOM (M is, for example, an alkali metal, alkaline earth metal or ammonium salt), or organocarbon radicals bonded via oxygen, such as $C_1$–$C_6$-alkoxy radicals.

The phosphine complexes can be prepared in a manner known per se, eg. as described in the documents mentioned at the outset. For example, customary commercially available metal salts such as $PdCl_2$ or $Pd(OCOCH_3)_2$ are used as starting materials and the phosphine, eg. $P(C_6H_5)_3$, $P(n-C_4H_9)_3$, $PCH_3(C_6H_5)_2$, 1,2-bis(diphenylphosphino)ethane, is added.

The amount of phosphine, based on the transition metal, is customarily from 0 to 20, in particular 0.1 to 10, mol equivalents, particularly preferably 1 to 5 mol equivalents.

The amount of transition metal is not critical. Of course, for reasons of cost rather a small amount, eg. from 0.1 to 10 mol %, in particular 1 to 5 mol %, based on the starting substance II or III, will be used.

For preparation of the benzoic acids III (T=OH), the reaction is carried out with carbon monoxide and at least equimolar amounts of water, based on the starting substances VI. The reaction component water can simultaneously also be used as a solvent, ie. the maximum amount is not critical.

However, depending on the nature of the starting substances and the catalysts used, it may also be advantageous instead of the reaction component to use as a solvent another inert solvent or the base used for the carboxylation.

Suitable inert solvents for carboxylation reactions are customary solvents such as hydrocarbons, eg. toluene, xylene, hexane, pentane, cyclohexane, ethers, eg. methyl tert-butyl ether, tetrahydrofuran, dioxane, dimethoxyethane, substituted amides such as dimethylformamide, persubstituted ureas such as tetra-$C_1$–$C_4$-alkylureas or nitrites such as benzonitrile or acetonitrile.

In a preferred embodiment of the process, one of the reaction components, in particular the base, is used in an excess, so that no additional solvent is necessary.

Bases suitable for the process are all inert bases which are able to bind hydrogen iodide or hydrogen bromide liberated during the reaction. Examples which may be mentioned here are tertiary amines such as tert-alkylamines, eg. trialkylamines such as triethylamine, cyclic amines such as N-methylpiperidine or N,N'-dimethylpiperazine, pyridine, alkali metal [lacuna] or hydrogencarbonates, or tetraalkyl-substituted urea derivatives such as tetra-$C_1$–$C_4$-alkylurea, eg. tetramethylurea.

The amount of base is not critical, customarily from 1 to 10, in particular from 1 to 5, mol are used. When simultaneously using the base as a solvent, the amount is generally proportioned such that the reaction components are dissolved, unnecessarily high excesses being avoided for reasons of practicability in order to save costs, to be able to employ small reaction vessels and to guarantee the reaction components maximum contact.

During the reaction, the carbon monoxide pressure is adjusted such that an excess of CO, based on VI, is always present. Preferably, the carbon monoxide pressure at room temperature is from 1 to 250 bar, in particular from 5 to 150 bar, of CO.

The carbonylation is generally carried out continuously or batchwise at from 20 to 250° C., in particular 30 to 150° C.

In the case of batchwise operation, carbon monoxide is expediently continuously injected onto the reaction mixture to maintain a constant pressure.

The arylhalogen compounds XVIII used as starting compounds are known or can easily be prepared by suitable combination of known syntheses and according to the reaction sequences described above.

With a view to the intended use of the benzoyl derivatives of the general formula I, suitable substituents are the following radicals:

L, M hydrogen, $C_1$–$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 1,1,2-trimethylpropyl, 1,2,2-trimethylpropyl, 1-ethyl-1-methylpropyl or 1-ethyl-2-methylpropyl, in particular methyl, ethyl, 1-methylethyl, 1-methylpropyl, 2-methylpropyl, 1,1-dimethylethyl and 1,1-dimethylpropyl;

$C_2$–$C_6$-alkenyl such as 2-propenyl, 2-butenyl, 3-butenyl, 1-methyl-2-propenyl, 2-methyl-2-propenyl, 2-pentenyl, 3-pentenyl, 4-pentenyl, 3-methyl-2-butenyl, 1-methyl-2-butenyl, 2-methyl-2-butenyl, 1-methyl-3-butenyl, 2-methyl-4-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3 pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,3-dimethyl-3-butenyl, 1,3-dimethyl-2-butenyl, 1,2-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and ethyl-2-methyl-2-propenyl, in particular 1-methyl-2-propenyl, 1-methyl-2-butenyl, 1,1-dimethyl-2-propenyl and 1,1-dimethyl-2-butenyl;

$C_2$–$C_6$-alkynyl such as propargyl, 2-butynyl, 3-butynyl, 2-pentynyl, 3-pentynyl, 4-pentynyl, 1-methyl-3-butynyl, 2-methyl-3-butynyl, 1-methyl-2-butynyl, 1,1-dimethyl-2 propynyl, 1-ethyl-2-propynyl, 2-hexynyl, 3-hexynyl, 4-hexynyl, 5-hexynyl, -1-methyl-2-pentynyl, 1-methyl-3-pentynyl, 1-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, -2,2-dimethyl-3-butynyl, 1-ethyl-2-butynyl, 1-ethyl-3-butynyl, 2-ethyl-3-butynyl and 1-ethyl-1-methyl-2-propynyl;

$C_1$–$C_4$-alkoxy such as methoxy, ethoxy, n-propoxy, 1-methylethoxy, n-butoxy, 1-methylpropoxy, 2-methylpropoxy and 1, 1-dimethylethoxy, in particular $C_1$–$C_3$-alkoxy such as methoxy, ethoxy, i-propoxy, it being possible for these groups to be substituted, if desired, by one to five halogen atoms such as fluorine, chlorine, bromine and iodine, preferably fluorine and chlorine or $C_1$–$C_4$-alkoxy as mentioned above.

Preferred hetaroyl derivatives are those of the formula Ia,

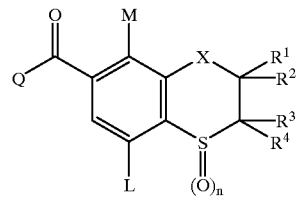

Ia where L is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, cyano or nitro and M is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, cyano or nitro and Q, X, $R_1$ to $R_4$ [sic] and n have the meanings given above.

Furthermore preferred hetaroyl derivatives are those of the formula Ib

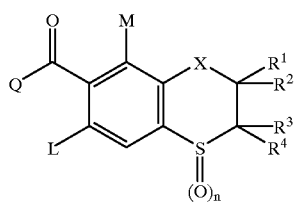

Ib where L is $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, cyano or nitro and M is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, cyano or nitro and Q, X, $R_1$ to $R_4$ [sic] and n have the meanings given above.

Preferred hetaroyl derivatives are also those of the formula I where the radicals L and M are hydrogen, methyl, methoxy, chlorine, cyano, nitro and trifluoromethyl.

Furthermore preferred hetaroyl derivatives are also those of the formula Ic

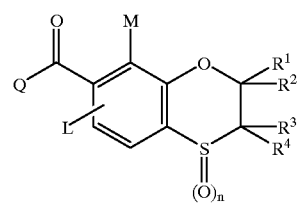

Ic where L is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, cyano or nitro and M is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, cyano or nitro and Q, $R_1$ to $R_4$ and n have the meanings given above.-

Preferred hetaroyl derivatives are also those of the formula Id

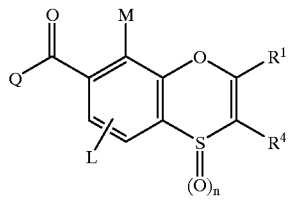

Id where L is hydrogen, $C_1-C_6$-alkyl, $C_2-C_6$-alkenyl, $C_2-C_6$-alkynyl, $C_1-C_4$-alkoxy, $C_1-C_4$-haloalkyl, $C_1-C_4$-haloalkoxy, halogen, cyano or nitro and M is hydrogen, $C_1-C_6$-alkyl, $C_2-C_6$-alkenyl, $C_2-C_6$-alkynyl, $C_1-C_4$-alkoxy, $C_1-C_4$-haloalkyl, $C_1-C_4$-haloalkoxy, halogen, cyano or nitro and Q, $R_1$, $R_4$ and n have the meanings given above.

Preferred hetaroyl derivatives are furthermore those of the formula Ie

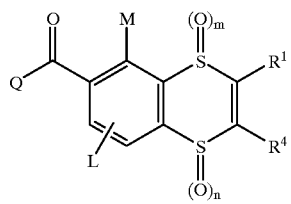

Ie where L is hydrogen, $C_1-C_6$-alkyl, $C_2-C_6$-alkenyl, $C_2-C_6$-alkynyl, $C_1-C_4$-alkoxy, $C_1-C_4$-haloalkyl, $C_1-C_4$-haloalkoxy, halogen, cyano or nitro and M is hydrogen, $C_1-C_6$-alkyl, $C_2-C_6$-alkenyl, $C_2-C_6$-alkynyl, $C_1-C_4$-alkoxy, $C_1-C_4$-haloalkyl, $C_1-C_4$-haloalkoxy, halogen, cyano or nitro, and m is zero, one or two and Q, $R_1$, $R_4$ and n have the meanings given above.

Preferred hetaroyl derivatives are also those of the formula If

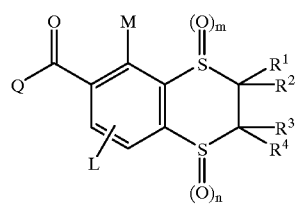

If where L is hydrogen, $C_1-C_6$-alkyl, $C_2-C_6$-alkenyl, $C_2-C_6$-alkynyl, $C_1-C_4$-alkoxy, $C_1-C_4$-haloalkyl, $C_1-C_4$-haloalkoxy, halogen, cyano or nitro and M is hydrogen, $C_1-C_6$-alkyl, $C_2-C_6$-alkenyl, $C_2-C_6$-alkynyl, $C_1-C_4$-alkoxy, $C_1-C_4$-haloalkyl, $C_1-C_4$-haloalkoxy, halogen, cyano or nitro, and m is zero, one or two and Q, $R_1$ to $R_4$ and n have the meanings given above.

Preferred hetaroyl derivatives of the formula I to If are also those whose substituents consist of a combination of the preferred substituents.

Particularly preferred compounds of the formula I are listed in the following Tables 1–6.

TABLE 1

| No. | $R^5$ | $R^6$ | $R^7$ | $R^8$ | M | L | X | n |
|-----|-------|-------|-------|-------|---|---|---|---|
| 1.1 | H | H | H | H | H | H | O | 0 |
| 1.2 | H | H | H | H | H | H | O | 2 |
| 1.3 | $CH_3$ | $CH_3$ | H | H | H | H | O | 0 |
| 1.4 | $CH_3$ | $CH_3$ | H | H | H | H | O | 2 |
| 1.5 | H | H | H | $CH_3$ | H | H | O | 0 |
| 1.6 | H | H | H | $CH_3$ | H | H | O | 2 |
| 1.7 | H | H | $CH_3$ | $CH_3$ | H | H | O | 0 |
| 1.8 | H | H | $CH_3$ | $CH_3$ | H | H | O | 2 |
| 1.9 | H | H | H | H | $CH_3$ | H | O | 0 |
| 1.10 | H | H | H | H | $CH_3$ | H | O | 2 |
| 1.11 | $CH_3$ | $CH_3$ | H | H | $CH_3$ | H | O | 0 |
| 1.12 | $CH_3$ | $CH_3$ | H | H | $CH_3$ | H | O | 2 |
| 1.13 | H | H | H | $CH_3$ | $CH_3$ | H | O | 0 |
| 1.14 | H | H | H | $CH_3$ | $CH_3$ | H | O | 2 |
| 1.15 | H | H | $CH_3$ | $CH_3$ | $CH_3$ | H | O | 0 |
| 1.16 | H | H | $CH_3$ | $CH_3$ | $CH_3$ | H | O | 2 |
| 1.17 | H | H | H | H | Cl | H | O | 0 |
| 1.18 | H | H | H | H | Cl | H | O | 2 |
| 1.19 | $CH_3$ | $CH_3$ | H | H | Cl | H | O | 0 |
| 1.20 | $CH_3$ | $CH_3$ | H | H | Cl | H | O | 2 |
| 1.21 | H | H | H | $CH_3$ | Cl | H | O | 0 |
| 1.22 | H | H | H | $CH_3$ | Cl | H | O | 2 |
| 1.23 | H | H | $CH_3$ | $CH_3$ | Cl | H | O | 0 |
| 1.24 | H | H | $CH_3$ | $CH_3$ | Cl | H | O | 2 |
| 1.25 | H | H | H | H | Cl | Cl | O | 0 |
| 1.26 | H | H | H | H | Cl | Cl | O | 2 |

TABLE 1-continued

| No. | $R^5$ | $R^6$ | $R^7$ | $R^8$ | M | L | X | n |
|---|---|---|---|---|---|---|---|---|
| 1.27 | CH$_3$ | CH$_3$ | H | H | Cl | Cl | O | 0 |
| 1.28 | CH$_3$ | CH$_3$ | H | H | Cl | Cl | O | 2 |
| 1.29 | H | H | H | CH$_3$ | Cl | Cl | O | 0 |
| 1.30 | H | H | H | CH$_3$ | Cl | Cl | O | 2 |
| 1.31 | H | H | CH$_3$ | CH$_3$ | Cl | Cl | O | 0 |
| 1.32 | H | H | CH$_3$ | CH$_3$ | Cl | Cl | O | 2 |
| 1.33 | H | H | H | H | CH$_3$ | CH$_3$ | O | 0 |
| 1.34 | H | H | H | H | CH$_3$ | CH$_3$ | O | 2 |
| 1.35 | CH$_3$ | CH$_3$ | H | H | CH$_3$ | CH$_3$ | O | 0 |
| 1.36 | CH$_3$ | CH$_3$ | H | H | CH$_3$ | CH$_3$ | O | 2 |
| 1.37 | H | H | H | CH$_3$ | CH$_3$ | CH$_3$ | O | 0 |
| 1.38 | H | H | H | CH$_3$ | CH$_3$ | CH$_3$ | O | 2 |
| 1.39 | H | H | CH$_3$ | CH$_3$ | CH$_3$ | CH$_3$ | O | 0 |
| 1.40 | H | H | CH$_3$ | CH$_3$ | CH$_3$ | CH$_3$ | O | 2 |
| 1.41 | H | H | H | H | NO$_2$ | H | O | 0 |
| 1.42 | H | H | H | H | NO$_2$ | H | O | 2 |
| 1.43 | CH$_3$ | CH$_3$ | H | H | NO$_2$ | H | O | 0 |
| 1.44 | CH$_3$ | CH$_3$ | H | H | NO$_2$ | H | O | 2 |
| 1.45 | H | H | H | CH$_3$ | NO$_2$ | H | O | 0 |
| 1.46 | H | H | H | CH$_3$ | NO$_2$ | H | O | 2 |
| 1.47 | H | H | CH$_3$ | CH$_3$ | NO$_2$ | H | O | 0 |
| 1.48 | H | H | CH$_3$ | CH$_3$ | NO$_2$ | H | O | 2 |
| 1.49 | H | H | H | H | OCH$_3$ | H | O | 0 |
| 1.50 | H | H | H | H | OCH$_3$ | H | O | 2 |
| 1.51 | CH$_3$ | CH$_3$ | H | H | OCH$_3$ | H | O | 0 |
| 1.52 | CH$_3$ | CH$_3$ | H | H | OCH$_3$ | H | O | 2 |
| 1.53 | H | H | H | CH$_3$ | OCH$_3$ | H | O | 0 |
| 1.54 | H | H | H | CH$_3$ | OCH$_3$ | H | O | 2 |
| 1.55 | H | H | CH$_3$ | CH$_3$ | OCH$_3$ | H | O | 0 |
| 1.56 | H | H | CH$_3$ | CH$_3$ | OCH$_3$ | H | O | 2 |
| 1.57 | H | H | H | H | H | H | S | 0 |
| 1.58 | H | H | H | H | H | H | S | 2 |
| 1.59 | CH$_3$ | CH$_3$ | H | H | H | H | S | 0 |
| 1.60 | CH$_3$ | CH$_3$ | H | H | H | H | S | 2 |
| 1.61 | H | H | H | CH$_3$ | H | H | S | 0 |
| 1.62 | H | H | H | CH$_3$ | H | H | S | 2 |
| 1.63 | H | H | CH$_3$ | CH$_3$ | H | H | S | 0 |
| 1.64 | H | H | CH$_3$ | CH$_3$ | H | H | S | 2 |
| 1.65 | H | H | H | H | CH$_3$ | H | S | 0 |
| 1.66 | H | H | H | H | CH$_3$ | H | S | 2 |
| 1.67 | CH$_3$ | CH$_3$ | H | H | CH$_3$ | H | S | 0 |
| 1.68 | CH$_3$ | CH$_3$ | H | H | CH$_3$ | H | S | 2 |
| 1.69 | H | H | H | CH$_3$ | CH$_3$ | H | S | 0 |
| 1.70 | H | H | H | CH$_3$ | CH$_3$ | H | S | 2 |
| 1.71 | H | H | CH$_3$ | CH$_3$ | CH$_3$ | H | S | 0 |
| 1.72 | H | H | CH$_3$ | CH$_3$ | CH$_3$ | H | S | 2 |
| 1.73 | H | H | H | H | Cl | H | S | 0 |
| 1.74 | H | H | H | H | Cl | H | S | 2 |
| 1.75 | CH$_3$ | CH$_3$ | H | H | Cl | H | S | 0 |
| 1.76 | CH$_3$ | CH$_3$ | H | H | Cl | H | S | 2 |
| 1.77 | H | H | H | CH$_3$ | Cl | H | S | 0 |
| 1.78 | H | H | H | CH$_3$ | Cl | H | S | 2 |
| 1.79 | H | H | CH$_3$ | CH$_3$ | Cl | H | S | 0 |
| 1.80 | H | H | CH$_3$ | CH$_3$ | Cl | H | S | 2 |
| 1.81 | H | H | H | H | Cl | Cl | S | 0 |
| 1.82 | H | H | H | H | Cl | Cl | S | 2 |
| 1.83 | CH$_3$ | CH$_3$ | H | H | Cl | Cl | S | 0 |
| 1.84 | CH$_3$ | CH$_3$ | H | H | Cl | Cl | S | 2 |
| 1.85 | H | H | H | CH$_3$ | Cl | Cl | S | 0 |
| 1.86 | H | H | H | CH$_3$ | Cl | Cl | S | 2 |
| 1.87 | H | H | CH$_3$ | CH$_3$ | Cl | Cl | S | 0 |
| 1.88 | H | H | CH$_3$ | CH$_3$ | Cl | Cl | S | 2 |
| 1.89 | H | H | H | H | CH$_3$ | CH$_3$ | S | 0 |
| 1.90 | H | H | H | H | CH$_3$ | CH$_3$ | S | 2 |
| 1.91 | CH$_3$ | CH$_3$ | H | H | CH$_3$ | CH$_3$ | S | 0 |
| 1.92 | CH$_3$ | CH$_3$ | H | H | CH$_3$ | CH$_3$ | S | 2 |
| 1.93 | H | H | H | CH$_3$ | CH$_3$ | CH$_3$ | S | 0 |

TABLE 1-continued

[Structure: cyclohexane-1,3-dione with OH and substituents R⁵, R⁶, R⁷, R⁸, connected via carbonyl to a benzene ring with M, L substituents and a fused ring containing X and S(O)ₙ]

| No. | $R^5$ | $R^6$ | $R^7$ | $R^8$ | M | L | X | n |
|---|---|---|---|---|---|---|---|---|
| 1.94 | H | H | H | $CH_3$ | $CH_3$ | $CH_3$ | S | 2 |
| 1.95 | H | H | $CH_3$ | $CH_3$ | $CH_3$ | $CH_3$ | S | 0 |
| 1.96 | H | H | $CH_3$ | $CH_3$ | $CH_3$ | $CH_3$ | S | 2 |
| 1.97 | H | H | H | H | $NO_2$ | H | S | 0 |
| 1.98 | H | H | H | H | $NO_2$ | H | S | 2 |
| 1.99 | $CH_3$ | $CH_3$ | H | H | $NO_2$ | H | S | 0 |
| 1.100 | $CH_3$ | $CH_3$ | H | H | $NO_2$ | H | S | 2 |
| 1.101 | H | H | H | $CH_3$ | $NO_2$ | H | S | 0 |
| 1.102 | H | H | H | $CH_3$ | $NO_2$ | H | S | 2 |
| 1.103 | H | H | $CH_3$ | $CH_3$ | $NO_2$ | H | S | 0 |
| 1.104 | H | H | $CH_3$ | $CH_3$ | $NO_2$ | H | S | 2 |
| 1.105 | H | H | H | H | $OCH_3$ | H | S | 0 |
| 1.106 | H | H | H | H | $OCH_3$ | H | S | 2 |
| 1.107 | $CH_3$ | $CH_3$ | H | H | $OCH_3$ | H | S | 0 |
| 1.108 | $CH_3$ | $CH_3$ | H | H | $OCH_3$ | H | S | 2 |
| 1.109 | H | H | H | $CH_3$ | $OCH_3$ | H | S | 0 |
| 1.110 | H | H | H | $CH_3$ | $OCH_3$ | H | S | 2 |
| 1.111 | H | H | $CH_3$ | $CH_3$ | $OCH_3$ | H | S | 0 |
| 1.112 | H | H | $CH_3$ | $CH_3$ | $OCH_3$ | H | S | 2 |
| 1.113 | H | H | H | H | H | H | $SO_2$ | 0 |
| 1.114 | H | H | H | H | H | H | $SO_2$ | 2 |
| 1.115 | $CH_3$ | $CH_3$ | H | H | H | H | $SO_2$ | 0 |
| 1.116 | $CH_3$ | $CH_3$ | H | H | H | H | $SO_2$ | 2 |
| 1.117 | H | H | H | $CH_3$ | H | H | $SO_2$ | 0 |
| 1.118 | H | H | H | $CH_3$ | H | H | $SO_2$ | 2 |
| 1.119 | H | H | $CH_3$ | $CH_3$ | H | H | $SO_2$ | 0 |
| 1.120 | H | H | $CH_3$ | $CH_3$ | H | H | $SO_2$ | 2 |
| 1.121 | H | H | H | H | $CH_3$ | H | $SO_2$ | 0 |
| 1.122 | H | H | H | H | $CH_3$ | H | $SO_2$ | 2 |
| 1.123 | $CH_3$ | $CH_3$ | H | H | $CH_3$ | H | $SO_2$ | 0 |
| 1.124 | $CH_3$ | $CH_3$ | H | H | $CH_3$ | H | $SO_2$ | 2 |
| 1.125 | H | H | H | $CH_3$ | $CH_3$ | H | $SO_2$ | 0 |
| 1.126 | H | H | H | $CH_3$ | $CH_3$ | H | $SO_2$ | 2 |
| 1.127 | H | H | $CH_3$ | $CH_3$ | $CH_3$ | H | $SO_2$ | 0 |
| 1.128 | H | H | $CH_3$ | $CH_3$ | $CH_3$ | H | $SO_2$ | 2 |
| 1.129 | H | H | H | H | Cl | H | $SO_2$ | 0 |
| 1.130 | H | H | H | H | Cl | H | $SO_2$ | 2 |
| 1.131 | $CH_3$ | $CH_3$ | H | H | Cl | H | $SO_2$ | 0 |
| 1.132 | $CH_3$ | $CH_3$ | H | H | Cl | H | $SO_2$ | 2 |
| 1.133 | H | H | H | $CH_3$ | Cl | H | $SO_2$ | 0 |
| 1.134 | H | H | H | $CH_3$ | Cl | H | $SO_2$ | 2 |
| 1.135 | H | H | $CH_3$ | $CH_3$ | Cl | H | $SO_2$ | 0 |
| 1.136 | H | H | $CH_3$ | $CH_3$ | Cl | H | $SO_2$ | 2 |
| 1.137 | H | H | H | H | Cl | Cl | $SO_2$ | 0 |
| 1.138 | H | H | H | H | Cl | Cl | $SO_2$ | 2 |
| 1.139 | $CH_3$ | $CH_3$ | H | H | Cl | Cl | $SO_2$ | 0 |
| 1.140 | $CH_3$ | $CH_3$ | H | H | Cl | Cl | $SO_2$ | 2 |
| 1.141 | H | H | H | $CH_3$ | Cl | Cl | $SO_2$ | 0 |
| 1.142 | H | H | H | $CH_3$ | Cl | Cl | $SO_2$ | 2 |
| 1.143 | H | H | $CH_3$ | $CH_3$ | Cl | Cl | $SO_2$ | 0 |
| 1.144 | H | H | $CH_3$ | $CH_3$ | Cl | Cl | $SO_2$ | 2 |
| 1.145 | H | H | H | H | $CH_3$ | $CH_3$ | $SO_2$ | 0 |
| 1.146 | H | H | H | H | $CH_3$ | $CH_3$ | $SO_2$ | 2 |
| 1.147 | $CH_3$ | $CH_3$ | H | H | $CH_3$ | $CH_3$ | $SO_2$ | 0 |
| 1.148 | $CH_3$ | $CH_3$ | H | H | $CH_3$ | $CH_3$ | $SO_2$ | 2 |
| 1.149 | H | H | H | $CH_3$ | $CH_3$ | $CH_3$ | $SO_2$ | 0 |
| 1.150 | H | H | H | $CH_3$ | $CH_3$ | $CH_3$ | $SO_2$ | 2 |
| 1.151 | H | H | $CH_3$ | $CH_3$ | $CH_3$ | $CH_3$ | $SO_2$ | 0 |
| 1.152 | H | H | $CH_3$ | $CH_3$ | $CH_3$ | $CH_3$ | $SO_2$ | 2 |
| 1.153 | H | H | H | H | $NO_2$ | H | $SO_2$ | 0 |
| 1.154 | H | H | H | H | $NO_2$ | H | $SO_2$ | 2 |
| 1.155 | $CH_3$ | $CH_3$ | H | H | $NO_2$ | H | $SO_2$ | 0 |
| 1.156 | $CH_3$ | $CH_3$ | H | H | $NO_2$ | H | $SO_2$ | 2 |
| 1.157 | H | H | H | $CH_3$ | $NO_2$ | H | $SO_2$ | 0 |
| 1.158 | H | H | H | $CH_3$ | $NO_2$ | H | $SO_2$ | 2 |
| 1.159 | H | H | $CH_3$ | $CH_3$ | NO | H | $SO_2$ | 0 |
| 1.160 | H | H | $CH_3$ | $CH_3$ | $NO_2$ | H | $SO_2$ | 2 |

TABLE 1-continued

| No. | R⁵ | R⁶ | R⁷ | R⁸ | M | L | X | n |
|---|---|---|---|---|---|---|---|---|
| 1.161 | H | H | H | H | OCH₃ | H | SO₂ | 0 |
| 1.162 | H | H | H | H | OCH₃ | H | SO₂ | 2 |
| 1.163 | CH₃ | CH₃ | H | H | OCH₃ | H | SO₂ | 0 |
| 1.164 | CH₃ | CH₃ | H | H | OCH₃ | H | SO₂ | 2 |
| 1.165 | H | H | H | CH₃ | OCH₃ | H | SO₂ | 0 |
| 1.166 | H | H | H | CH₃ | OCH₃ | H | SO₂ | 2 |
| 1.167 | H | H | CH₃ | CH₃ | OCH₃ | H | SO₂ | 0 |
| 1.168 | H | H | CH₃ | CH₃ | OCH₃ | H | SO₂ | 2 |
| 1.169 | H | H | 2-Ethylthiopropyl | H | H | H | O | 0 |
| 1.170 | H | H | 2-Ethylthiopropyl | H | H | H | O | 2 |
| 1.171 | H | H | 2-Ethylthiopropyl | H | CH₃ | H | O | 0 |
| 1.172 | H | H | 2-Ethylthiopropyl | H | CH₃ | H | O | 0 |
| 1.173 | H | H | 2-Etbylthiopropyl | H | Cl | H | O | 0 |
| 1.174 | H | H | 2-Ethylthiopropyl | H | Cl | H | O | 2 |
| 1.175 | H | H | 2-Ethylthiopropyl | H | Cl | Cl | O | 0 |
| 1.176 | H | H | 2-Ethylthiopropyl | H | Cl | Cl | O | 2 |
| 1.177 | H | H | 2-Ethylthiopropyl | H | CH₃ | CH₃ | O | 0 |
| 1.178 | H | H | 2-Ethylthiopropyl | H | CH₃ | CH₃ | O | 2 |
| 1.179 | H | H | 2-Ethylthiopropyl | H | NO₂ | H | O | 0 |
| 1.180 | H | H | 2-Ethylthiopropyl | H | NO₂ | H | O | 2 |
| 1.181 | H | H | 2-Ethylthiopropyl | H | OCH₃ | H | O | 0 |
| 1.182 | H | H | 2-Ethylthiopropyl | H | OCH₃ | H | O | 2 |
| 1.183 | H | H | 2-Ethylthiopropyl | H | H | H | S | 0 |
| 1.184 | H | H | 2-Ethylthiopropyl | H | H | H | S | 2 |
| 1.185 | H | H | 2-Ethylthiopropyl | H | CH₃ | H | S | 0 |
| 1.186 | H | H | 2-Ethylthiopropyl | H | CH₃ | H | S | 2 |
| 1.187 | H | H | 2-Ethylthiopropyl | H | Cl | H | S | 0 |
| 1.188 | H | H | 2-Ethylthiopropyl | H | Cl | H | S | 2 |
| 1.189 | H | H | 2-Ethylthiopropyl | H | Cl | Cl | S | 0 |
| 1.190 | H | H | 2-Ethylthiopropyl | H | Cl | Cl | S | 2 |
| 1.191 | H | H | 2-Ethylthiopropyl | H | CH₃ | CH₃ | S | 0 |
| 1.192 | H | H | 2-Ethylthiopropyl | H | CH₃ | CH₃ | S | 2 |
| 1.193 | H | H | 2-Ethylthiopropyl | H | H | H | SO₂ | 0 |
| 1.194 | H | H | 2-Ethylthiopropyl | H | H | H | SO₂ | 2 |
| 1.195 | H | H | 2-Ethylthiopropyl | H | CH₃ | H | SO₂ | 0 |
| 1.196 | H | H | 2-Ethylthiopropyl | H | CH₃ | H | SO₂ | 2 |
| 1.197 | H | H | 2-Ethylthiopropyl | H | Cl | H | SO₂ | 0 |
| 1.198 | H | H | 2-Ethylthiopropyl | H | Cl | H | SO₂ | 2 |
| 1.199 | H | H | 2-Ethylthiopropyl | H | Cl | Cl | SO₂ | 0 |
| 1.200 | H | H | 2-Ethylthiopropyl | H | Cl | Cl | SO₂ | 2 |
| 1.201 | H | H | 2-Ethylthiopropyl | H | CH₃ | CH₃ | SO₂ | 0 |
| 1.202 | H | H | 2-Ethylthiopropyl | H | CH₃ | CH₃ | SO₂ | 2 |
| 1.203 | H | H | Tetrahydropyran-3-yl | H | H | H | O | 0 |
| 1.204 | H | H | Tetrahydropyran-3-yl | H | H | H | O | 2 |
| 1.205 | H | H | Tetrahydropyran-3-yl | H | CH₃ | H | O | 0 |
| 1.206 | H | H | Tetrahydropyran-3-yl | H | CH₃ | H | O | 0 |
| 1.207 | H | H | Tetrahydropyran-3-yl | H | Cl | H | O | 0 |
| 1.208 | H | H | Tetrahydropyran-3-yl | H | Cl | H | O | 2 |
| 1.209 | H | H | Tetrahydropyran-3-yl | H | Cl | Cl | O | 0 |
| 1.210 | H | H | Tetrahydropyran-3-yl | H | Cl | Cl | O | 2 |
| 1.211 | H | H | Tetrahydropyran-3-yl | H | CH₃ | CH₃ | O | 0 |
| 1.212 | H | H | Tetrahydropyran-3-yl | H | CH₃ | CH₃ | O | 2 |
| 1.213 | H | H | Tetrahydropyran-3-yl | H | NO₂ | H | O | 0 |
| 1.214 | H | H | Tetrahydropyran-3-yl | H | NO₂ | H | O | 2 |
| 1.215 | H | H | Tetrahydropyran-3-yl | H | OCH₃ | H | O | 0 |
| 1.216 | H | H | Tetrahydropyran-3-yl | H | OCH₃ | H | O | 2 |
| 1.217 | H | H | Tetrahydropyran-3-yl | H | H | H | S | 0 |
| 1.218 | H | H | Tetrahydropyran-3-yl | H | H | H | S | 2 |
| 1.219 | H | H | Tetrahydropyran-3-yl | H | CH₃ | H | S | 0 |
| 1.220 | H | H | Tetrahydropyran-3-yl | H | CH₃ | H | S | 2 |
| 1.221 | H | H | Tetrahydropyran-3-yl | H | Cl | H | S | 0 |
| 1.222 | H | H | Tetrahydropyran-3-yl | H | Cl | H | S | 2 |
| 1.223 | H | H | Tetrahydropyran-3-yl | H | Cl | Cl | S | 0 |
| 1.224 | H | H | Tetrahydropyran-3-yl | H | Cl | Cl | S | 2 |
| 1.225 | H | H | Tetrahydropyran-3-yl | H | CH₃ | CH₃ | S | 0 |
| 1.226 | H | H | Tetrahydropyran-3-yl | H | CH₃ | CH₃ | S | 2 |
| 1.227 | H | H | Tetrahydropyran-3-yl | H | H | H | SO₂ | 0 |

TABLE 1-continued

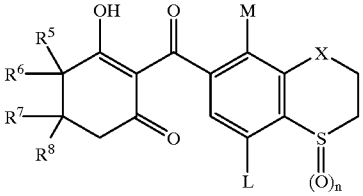

| No. | R⁵ | R⁶ | R⁷ | R⁸ | M | L | X | n |
|---|---|---|---|---|---|---|---|---|
| 1.228 | H | H | Tetrahydropyran-3-yl | H | H | H | SO₂ | 2 |
| 1.229 | H | H | Tetrahydropyran-3-yl | H | CH₃ | H | SO₂ | 0 |
| 1.230 | H | H | Tetrahydropyran-3-yl | H | CH₃ | H | SO₂ | 2 |
| 1.231 | H | H | Tetrahydropyran-3-yl | H | Cl | H | SO₂ | 0 |
| 1.232 | H | H | Tetrahydropyran-3-yl | H | Cl | H | SO₂ | 2 |
| 1.233 | H | H | Tetrahydropyran-3-yl | H | Cl | Cl | SO₂ | 0 |
| 1.234 | H | H | Tetrahydropyran-3-yl | H | Cl | Cl | SO₂ | 2 |
| 1.235 | H | H | Tetrahydropyran-3-yl | H | CH₃ | CH₃ | SO₂ | 0 |
| 1.236 | H | H | Tetrahydropyran-3-yl | H | CH₃ | CH₃ | SO₂ | 2 |
| 1.237 | H | H | Tetrahydropyran-4-yl | H | CH₃ | H | O | 2 |
| 1.238 | H | H | Tetrahydropyran-4-yl | H | Cl | H | O | 2 |
| 1.239 | H | H | Tetrahydropyran-4-yl | H | Cl | Cl | O | 2 |
| 1.240 | H | H | Tetrahydropyran-4-yl | H | CH₃ | CH₃ | O | 2 |
| 1.241 | H | H | Tetrahydropyran-4-yl | H | CH₃ | H | S | 2 |
| 1.242 | H | H | Tetrahydropyran-4-yl | H | Cl | H | S | 2 |
| 1.243 | H | H | Tetrahydropyran-4-yl | H | CH₃ | H | SO₂ | 2 |
| 1.244 | H | H | Tetrahydropyran-4-yl | H | Cl | H | SO₂ | 2 |
| 1.245 | R | H | 1-Methylthiocyclo-propyl | H | CH₃ | H | O | 2 |
| 1.246 | H | H | 1-Methylthiocyclo-propyl | H | Cl | H | O | 2 |
| 1.247 | H | H | 1-Methylthiocyclo-propyl | H | Cl | Cl | O | 2 |
| 1.248 | H | H | 1-Methylthiocyclo-propyl | H | CH₃ | CH₃ | O | 2 |
| 1.249 | H | H | 1-Methylthiocyclo-propyl | H | CH₃ | H | S | 2 |
| 1.250 | H | H | 1-Methylthiocyclo-propyl | H | Cl | H | S | 2 |
| 1.251 | H | H | 1-Methylthiocyclo-propyl | H | CH₃ | H | SO₂ | 2 |
| 1.252 | H | H | 1-Methylthiocyclo-propyl | H | Cl | H | SO₂ | 2 |
| 1.253 | H | H | (Dimethoxy)methyl | H | CH₃ | H | O | 2 |
| 1.254 | H | H | (Dimethoxy)methyl | H | Cl | H | O | 2 |
| 1.255 | H | H | (Dimethoxy)methyl | H | Cl | Cl | O | 2 |
| 1.256 | H | H | (Dimethoxy)methyl | H | CH₃ | CH₃ | O | 2 |
| 1.257 | H | H | (Dimethoxy)methyl | H | CH₃ | H | S | 2 |
| 1.258 | H | H | (Dimethoxy)methyl | H | Cl | H | S | 2 |
| 1.259 | H | H | (Dimethoxy)methyl | H | CH₃ | H | SO₂ | 2 |
| 1.260 | H | H | (Dimethoxy)methyl | H | Cl | H | SO₂ | 2 |

TABLE 2

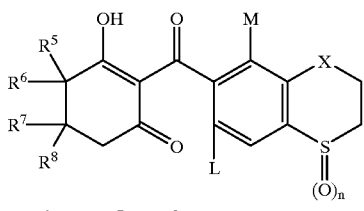

TABLE 2-continued

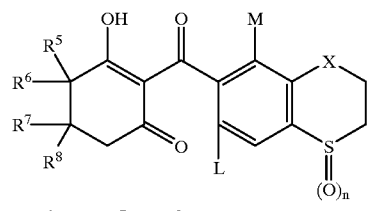

| No. | R⁵ | R⁶ | R⁷ | R⁸ | L | M | X | n | No. | R⁵ | R⁶ | R⁷ | R⁸ | L | M | X | n |
|---|---|---|---|---|---|---|---|---|---|---|---|---|---|---|---|---|---|
| 2.1 | H | H | H | H | CH₃ | H | O | 0 | 2.9 | H | H | H | H | Cl | H | O | 0 |
| 2.2 | H | H | H | H | CH₃ | H | O | 2 | 2.10 | H | H | H | H | Cl | H | O | 2 |
| 2.3 | CH₃ | CH₃ | H | H | CH₃ | H | O | 0 | 2.11 | CH₃ | CH₃ | H | H | Cl | H | O | 0 |
| 2.4 | CH₃ | CH₃ | H | H | CH₃ | H | O | 2 | 2.12 | CH₃ | CH₃ | H | H | Cl | H | O | 2 |
| 2.5 | H | H | H | CH₃ | CH₃ | H | O | 0 | 2.13 | H | H | H | CH₃ | Cl | H | O | 0 |
| 2.6 | H | H | H | CH₃ | CH₃ | H | O | 2 | 2.14 | H | H | H | CH₃ | Cl | H | O | 2 |
| 2.7 | H | H | CH₃ | CH₃ | CH₃ | H | O | 0 | 2.15 | H | H | CH₃ | CH₃ | Cl | H | O | 0 |
| 2.8 | H | H | CH₃ | CH₃ | CH₃ | H | O | 2 | 2.16 | H | H | CH₃ | CH₃ | Cl | H | O | 2 |

TABLE 2-continued

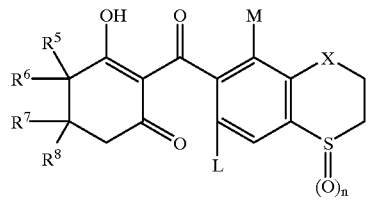

| No. | R⁵ | R⁶ | R⁷ | R⁸ | L | M | X | n |
|---|---|---|---|---|---|---|---|---|
| 2.17 | H | H | H | H | Cl | Cl | O | 0 |
| 2.18 | H | H | H | H | Cl | Cl | O | 2 |
| 2.19 | CH₃ | CH₃ | H | H | Cl | Cl | O | 0 |
| 2.20 | CH₃ | CH₃ | H | H | Cl | Cl | O | 2 |
| 2.21 | H | H | H | CH₃ | Cl | Cl | O | 0 |
| 2.22 | H | H | H | CH₃ | Cl | Cl | O | 2 |
| 2.23 | H | H | CH₃ | CH₃ | Cl | Cl | O | 0 |
| 2.24 | H | H | CH₃ | CH₃ | Cl | Cl | O | 2 |
| 2.25 | H | H | H | H | CH₃ | CH₃ | O | 0 |
| 2.26 | H | H | H | H | CH₃ | CH₃ | O | 2 |
| 2.27 | CH₃ | CH₃ | H | H | CH₃ | CH₃ | O | 0 |
| 2.28 | CH₃ | CH₃ | H | H | CH₃ | CH₃ | O | 2 |
| 2.29 | H | H | H | CH₃ | CH₃ | CH₃ | O | 0 |
| 2.30 | H | H | H | CH₃ | CH₃ | CH₃ | O | 2 |
| 2.31 | H | H | CH₃ | CH₃ | CH₃ | CH₃ | O | 0 |
| 2.32 | H | H | CH₃ | CH₃ | CH₃ | CH₃ | O | 2 |
| 2.33 | H | H | H | H | CH₃ | H | S | 0 |
| 2.34 | H | H | H | H | CH₃ | H | S | 2 |
| 2.35 | CH₃ | CH₃ | H | H | CH₃ | H | S | 0 |
| 2.36 | CH₃ | CH₃ | H | H | CH₃ | H | S | 2 |
| 2.37 | H | H | H | CH₃ | CH₃ | H | S | 0 |
| 2.38 | H | H | H | CH₃ | CH₃ | H | S | 2 |
| 2.39 | H | H | CH₃ | CH₃ | CH₃ | H | S | 0 |
| 2.40 | H | H | CH₃ | CH₃ | CH₃ | H | S | 2 |
| 2.41 | H | H | H | H | Cl | H | S | 0 |
| 2.42 | H | H | H | H | Cl | H | S | 2 |
| 2.43 | CH₃ | CH₃ | H | H | Cl | H | S | 0 |
| 2.44 | CH₃ | CH₃ | H | H | Cl | H | S | 2 |
| 2.45 | H | H | H | CH₃ | Cl | H | S | 0 |
| 2.46 | H | H | H | CH₃ | Cl | H | S | 2 |
| 2.47 | H | H | CH₃ | CH₃ | Cl | H | S | 0 |
| 2.48 | H | H | CH₃ | CH₃ | Cl | H | S | 2 |
| 2.49 | H | H | H | H | Cl | Cl | S | 0 |
| 2.50 | H | H | H | H | Cl | Cl | S | 2 |
| 2.51 | CH₃ | CH₃ | H | H | Cl | Cl | S | 0 |
| 2.52 | CH₃ | CH₃ | H | H | Cl | Cl | S | 2 |
| 2.53 | H | H | H | CH₃ | Cl | Cl | S | 0 |
| 2.54 | H | H | H | CH₃ | Cl | Cl | S | 2 |
| 2.55 | H | H | CH₃ | CH₃ | Cl | Cl | S | 0 |
| 2.56 | H | H | CH₃ | CH₃ | Cl | Cl | S | 2 |
| 2.57 | H | H | H | H | CH₃ | CH₃ | S | 0 |
| 2.58 | H | H | H | H | CH₃ | CH₃ | S | 2 |
| 2.59 | CH₃ | CH₃ | H | H | CH₃ | CH₃ | S | 0 |
| 2.60 | CH₃ | CH₃ | H | H | CH₃ | CH₃ | S | 2 |
| 2.61 | H | H | H | CH₃ | CH₃ | CH₃ | S | 0 |
| 2.62 | H | H | H | CH₃ | CH₃ | CH₃ | S | 2 |
| 2.63 | H | H | CH₃ | CH₃ | CH₃ | CH₃ | S | 0 |
| 2.64 | H | H | CH₃ | CH₃ | CH₃ | CH₃ | S | 2 |
| 2.65 | H | H | H | H | CH₃ | H | SO₂ | 0 |
| 2.66 | H | H | H | H | CH₃ | H | SO₂ | 2 |
| 2.67 | CH₃ | CH₃ | H | H | CH₃ | H | SO₂ | 0 |
| 2.68 | CH₃ | CH₃ | H | H | CH₃ | H | SO₂ | 2 |
| 2.69 | H | H | H | CH₃ | CH₃ | H | SO₂ | 0 |
| 2.70 | H | H | H | CH₃ | CH₃ | H | SO₂ | 2 |
| 2.71 | H | H | CH₃ | CH₃ | CH₃ | H | SO₂ | 0 |
| 2.72 | H | H | CH₃ | CH₃ | CH₃ | H | SO₂ | 2 |
| 2.73 | H | H | H | H | Cl | H | SO₂ | 0 |
| 2.74 | H | H | H | H | Cl | H | SO₂ | 2 |
| 2.75 | CH₃ | CH₃ | H | H | Cl | H | SO₂ | 0 |
| 2.76 | CH₃ | CH₃ | H | H | Cl | H | SO₂ | 2 |
| 2.77 | H | H | H | CH₃ | Cl | H | SO₂ | 0 |
| 2.78 | H | H | H | CH₃ | Cl | H | SO₂ | 2 |
| 2.79 | H | H | CH₃ | CH₃ | Cl | H | SO₂ | 0 |
| 2.80 | H | H | CH₃ | CH₃ | Cl | H | SO₂ | 2 |
| 2.81 | H | H | H | H | Cl | Cl | SO₂ | 0 |
| 2.82 | H | H | H | H | Cl | Cl | SO₂ | 2 |
| 2.83 | CH₃ | CH₃ | H | H | Cl | Cl | SO₂ | 0 |

TABLE 2-continued

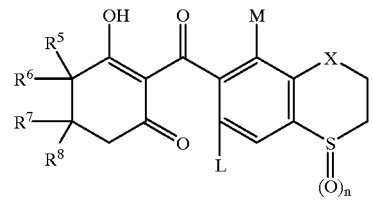

| No. | R⁵ | R⁶ | R⁷ | R⁸ | L | M | X | n |
|---|---|---|---|---|---|---|---|---|
| 2.84 | CH₃ | CH₃ | H | H | Cl | Cl | SO₂ | 2 |
| 2.85 | H | H | H | CH₃ | Cl | Cl | SO₂ | 0 |
| 2.86 | H | H | H | CH₃ | Cl | Cl | SO₂ | 2 |
| 2.87 | H | H | CH₃ | CH₃ | Cl | Cl | SO₂ | 0 |
| 2.88 | H | H | CH₃ | CH₃ | Cl | Cl | SO₂ | 2 |
| 2.89 | H | H | H | H | CH₃ | CH₃ | SO₂ | 0 |
| 2.90 | H | H | H | H | CH₃ | CH₃ | SO₂ | 2 |
| 2.91 | CH₃ | CH₃ | H | H | CH₃ | CH₃ | SO₂ | 0 |
| 2.92 | CH₃ | CH₃ | H | H | CH₃ | CH₃ | SO₂ | 2 |
| 2.93 | H | H | H | CH₃ | CH₃ | CH₃ | SO₂ | 0 |
| 2.94 | H | H | H | CH₃ | CH₃ | CH₃ | SO₂ | 2 |
| 2.95 | H | H | CH₃ | CH₃ | CH₃ | CH₃ | SO₂ | 0 |
| 2.96 | H | H | CH₃ | CH₃ | CH₃ | CH₃ | SO₂ | 2 |

TABLE 3

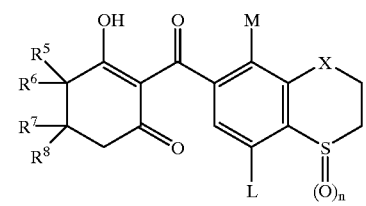

| No. | R⁵ | R⁶ | R⁷ | R⁸ | M | L | X | n |
|---|---|---|---|---|---|---|---|---|
| 7.1 | H | H | H | H | H | H | O | 0 |
| 7.2 | H | H | H | H | H | H | O | 2 |
| 7.3 | CH₃ | CH₃ | H | H | H | H | O | 0 |
| 7.4 | CH₃ | CH₃ | H | H | H | H | O | 2 |
| 7.5 | H | H | H | CH₃ | H | H | O | 0 |
| 7.6 | H | H | H | CH₃ | H | H | O | 2 |
| 7.7 | H | H | CH₃ | CH₃ | H | H | O | 0 |
| 7.8 | H | H | CH₃ | CH₃ | H | H | O | 2 |
| 7.9 | H | H | H | H | CH₃ | H | O | 0 |
| 7.10 | H | H | H | H | CH₃ | H | O | 2 |
| 7.11 | CH₃ | CH₃ | H | H | CH₃ | H | O | 0 |
| 7.12 | CH₃ | CH₃ | H | H | CH₃ | H | O | 2 |
| 7.13 | H | H | H | CH₃ | CH₃ | H | O | 0 |
| 7.14 | H | H | H | CH₃ | CH₃ | H | O | 2 |
| 7.15 | H | H | CH₃ | CH₃ | CH₃ | H | O | 0 |
| 7.16 | H | H | CH₃ | CH₃ | CH₃ | H | O | 2 |
| 7.17 | H | H | H | H | Cl | H | O | 0 |
| 7.18 | H | H | H | H | Cl | H | O | 2 |
| 7.19 | CH₃ | CH₃ | H | H | Cl | H | O | 0 |
| 7.20 | CH₃ | CH₃ | H | H | Cl | H | O | 2 |
| 7.21 | H | H | H | CH₃ | Cl | H | O | 0 |
| 7.22 | H | H | H | CH₃ | Cl | H | O | 2 |
| 7.23 | H | H | CH₃ | CH₃ | Cl | H | O | 0 |
| 7.24 | H | H | CH₃ | CH₃ | Cl | H | O | 2 |
| 7.25 | H | H | H | H | Cl | Cl | O | 0 |
| 7.26 | H | H | H | H | Cl | Cl | O | 2 |
| 7.27 | CH₃ | CH₃ | H | H | Cl | Cl | O | 0 |
| 7.28 | CH₃ | CH₃ | H | R | Cl | Cl | O | 2 |
| 7.29 | H | H | H | CH₃ | Cl | Cl | O | 0 |
| 7.30 | H | H | H | CH₃ | Cl | Cl | O | 2 |
| 7.31 | H | H | CH₃ | CH₃ | Cl | Cl | O | 0 |
| 7.32 | H | H | CH₃ | CH₃ | Cl | Cl | O | 2 |
| 7.33 | H | H | H | H | CH₃ | CH₃ | O | 0 |
| 7.34 | H | H | H | H | CH₃ | CH₃ | O | 2 |
| 7.35 | CH₃ | CH₃ | H | H | CH₃ | CH₃ | O | 0 |
| 7.36 | CH₃ | CH₃ | H | H | CH₃ | CH₃ | O | 2 |

TABLE 3-continued

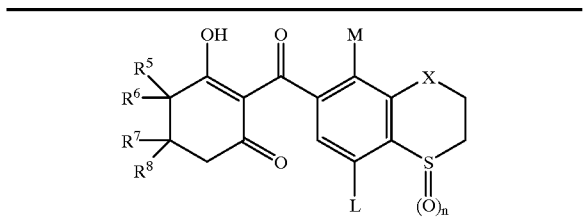 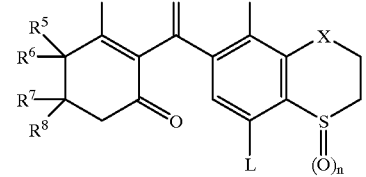

| No. | R⁵ | R⁶ | R⁷ | R⁸ | M | L | X | n |
|---|---|---|---|---|---|---|---|---|
| 7.37 | H | H | H | CH₃ | CH₃ | CH₃ | O | 0 |
| 7.38 | H | H | H | CH₃ | CH₃ | CH₃ | O | 2 |
| 7.39 | H | H | CH₃ | CH₃ | CH₃ | CH₃ | O | 0 |
| 7.40 | H | H | CH₃ | CH₃ | CH₃ | CH₃ | O | 2 |
| 7.41 | H | H | H | H | NO₂ | H | O | 0 |
| 7.42 | H | H | H | H | NO₂ | H | O | 2 |
| 7.43 | CH₃ | CH₃ | H | H | NO₂ | H | O | 0 |
| 7.44 | CH₃ | CH₃ | H | H | NO₂ | H | O | 2 |
| 7.45 | H | H | H | CH₃ | NO₂ | H | O | 0 |
| 7.46 | H | H | H | CH₃ | NO₂ | H | O | 2 |
| 7.47 | H | H | CH₃ | CH₃ | NO₂ | H | O | 0 |
| 7.48 | H | H | CH₃ | CH₃ | NO₂ | H | O | 2 |
| 7.49 | H | H | H | H | OCH₃ | H | O | 0 |
| 7.50 | H | H | H | H | OCH₃ | H | O | 2 |
| 7.51 | CH₃ | CH₃ | H | H | OCH₃ | H | O | 0 |
| 7.52 | CH₃ | CH₃ | H | H | OCH₃ | H | O | 2 |
| 7.53 | H | H | H | CH₃ | OCH₃ | H | O | 0 |
| 7.54 | H | H | H | CH₃ | OCH₃ | H | O | 2 |
| 7.55 | H | H | CH₃ | CH₃ | OCH₃ | H | O | 0 |
| 7.56 | H | H | CH₃ | CH₃ | OCH₃ | H | O | 2 |
| 7.57 | H | H | H | H | H | H | S | 0 |
| 7.58 | H | H | H | H | H | H | S | 2 |
| 7.59 | CH₃ | CH₃ | H | H | H | H | S | 0 |
| 7.60 | CH₃ | CH₃ | H | H | H | H | S | 2 |
| 7.61 | H | H | H | CH₃ | H | H | S | 0 |
| 7.62 | H | H | H | CH₃ | H | H | S | 2 |
| 7.63 | H | H | CH₃ | CH₃ | H | H | S | 0 |
| 7.64 | H | H | CH₃ | CH₃ | H | H | S | 2 |
| 7.65 | H | H | H | H | CH₃ | H | S | 0 |
| 7.66 | H | H | H | H | CH₃ | H | S | 2 |
| 7.67 | CH₃ | CH₃ | H | H | CH₃ | H | S | 0 |
| 7.68 | CH₃ | CH₃ | H | H | CH₃ | H | S | 2 |
| 7.69 | H | H | H | CH₃ | CH₃ | H | S | 0 |
| 7.70 | H | H | H | CH₃ | CH₃ | H | S | 2 |
| 7.71 | H | H | CH₃ | CH₃ | CH₃ | H | S | 0 |
| 7.72 | H | H | CH₃ | CH₃ | CH₃ | H | S | 2 |
| 7.73 | H | H | H | H | Cl | H | S | 0 |
| 7.74 | H | H | H | H | Cl | H | S | 2 |
| 7.75 | CH₃ | CH₃ | H | H | Cl | H | S | 0 |
| 7.76 | CH₃ | CH₃ | H | H | Cl | H | S | 2 |
| 7.77 | H | H | H | CH₃ | Cl | H | S | 0 |
| 7.78 | H | H | H | CH₃ | Cl | H | S | 2 |
| 7.79 | H | H | CH₃ | CH₃ | Cl | H | S | 0 |
| 7.80 | H | H | CH₃ | CH₃ | Cl | H | S | 2 |
| 7.81 | H | H | H | H | Cl | Cl | S | 0 |
| 7.82 | H | H | H | H | Cl | Cl | S | 2 |
| 7.83 | CH₃ | CH₃ | H | H | Cl | Cl | S | 0 |
| 7.84 | CH₃ | CH₃ | H | H | Cl | Cl | S | 2 |
| 7.85 | H | H | H | CH₃ | Cl | Cl | S | 0 |
| 7.86 | H | H | H | CH₃ | Cl | Cl | S | 2 |
| 7.87 | H | H | CH₃ | CH₃ | Cl | Cl | S | 0 |
| 7.88 | H | H | CH₃ | CH₃ | Cl | Cl | S | 2 |
| 7.89 | H | H | H | H | CH₃ | CH₃ | S | 0 |
| 7.90 | H | H | H | H | CH₃ | CH₃ | S | 2 |
| 7.91 | CH₃ | CH₃ | H | H | CH₃ | CH₃ | S | 0 |
| 7.92 | CH₃ | CH₃ | H | H | CH₃ | CH₃ | S | 2 |
| 7.93 | H | H | H | CH₃ | CH₃ | CH₃ | S | 0 |
| 7.94 | H | H | H | CH₃ | CH₃ | CH₃ | S | 2 |
| 7.95 | H | H | CH₃ | CH₃ | CH₃ | CH₃ | S | 0 |
| 7.96 | H | H | CH₃ | CH₃ | CH₃ | CH₃ | S | 2 |
| 7.97 | H | H | H | H | NO₂ | H | S | 0 |
| 7.98 | H | H | H | H | NO₂ | H | S | 2 |
| 7.99 | CH₃ | CH₃ | H | H | NO₂ | H | S | 0 |
| 7.100 | CH₃ | CH₃ | H | H | NO₂ | H | S | 2 |
| 7.101 | H | H | H | CH₃ | NO₂ | H | S | 0 |
| 7.102 | H | H | H | CH₃ | NO₂ | H | S | 2 |
| 7.103 | H | H | CH₃ | CH₃ | NO₂ | H | S | 0 |
| 7.104 | H | H | CH₃ | CH₃ | NO₂ | H | S | 2 |
| 7.105 | H | H | H | H | OCH₃ | H | S | 0 |
| 7.106 | H | H | H | H | OCH₃ | H | S | 2 |
| 7.107 | CH₃ | CH₃ | H | H | OCH₃ | H | S | 0 |
| 7.108 | CH₃ | CH₃ | H | H | OCH₃ | H | S | 2 |
| 7.109 | H | H | H | CH₃ | OCH₃ | H | S | 0 |
| 7.110 | H | H | H | CH₃ | OCH₃ | H | S | 2 |
| 7.111 | H | H | CH₃ | CH₃ | OCH₃ | H | S | 0 |
| 7.112 | H | H | CH₃ | CH₃ | OCH₃ | H | S | 2 |
| 7.113 | H | H | H | H | H | H | SO₂ | 0 |
| 7.114 | H | H | H | H | H | H | SO₂ | 2 |
| 7.115 | CH₃ | CH₃ | H | H | H | H | SO₂ | 0 |
| 7.116 | CH₃ | CH₃ | H | H | H | H | SO₂ | 2 |
| 7.117 | H | H | H | CH₃ | H | H | SO₂ | 0 |
| 7.118 | H | H | H | CH₃ | H | H | SO₂ | 2 |
| 7.119 | H | H | CH₃ | CH₃ | H | H | SO₂ | 0 |
| 7.120 | H | H | CH₃ | CH₃ | H | H | SO₂ | 2 |
| 7.121 | H | H | H | H | CH₃ | H | SO₂ | 0 |
| 7.122 | H | H | H | H | CH₃ | H | SO₂ | 2 |
| 7.123 | CH₃ | CH₃ | H | H | CH₃ | H | SO₂ | 0 |
| 7.124 | CH₃ | CH₃ | H | H | CH₃ | H | SO₂ | 2 |
| 7.125 | H | H | H | CH₃ | CH₃ | H | SO₂ | 0 |
| 7.126 | H | H | H | CH₃ | CH₃ | H | SO₂ | 2 |
| 7.127 | H | H | CH₃ | CH₃ | CH₃ | H | SO₂ | 0 |
| 7.128 | H | H | CH₃ | CH₃ | CH₃ | H | SO₂ | 2 |
| 7.129 | H | H | H | H | Cl | H | SO₂ | 0 |
| 7.130 | H | H | H | H | Cl | H | SO₂ | 2 |
| 7.131 | CH₃ | CH₃ | H | H | Cl | H | SO₂ | 0 |
| 7.132 | CH₃ | CH₃ | H | H | Cl | H | SO₂ | 2 |
| 7.133 | H | H | H | CH₃ | Cl | H | SO₂ | 0 |
| 7.134 | H | H | H | CH₃ | Cl | H | SO₂ | 2 |
| 7.135 | H | H | CH₃ | CH₃ | Cl | H | SO₂ | 0 |
| 7.136 | H | H | CH₃ | CH₃ | Cl | H | SO₂ | 2 |
| 7.137 | H | H | H | H | Cl | Cl | SO₂ | 0 |
| 7.138 | H | H | H | H | Cl | Cl | SO₂ | 2 |
| 7.139 | CH₃ | CH₃ | H | H | Cl | Cl | SO₂ | 0 |
| 7.140 | CH₃ | CH₃ | H | H | Cl | Cl | SO₂ | 2 |
| 7.141 | H | H | H | CH₃ | Cl | Cl | SO₂ | 0 |
| 7.142 | H | H | H | CH₃ | Cl | Cl | SO₂ | 2 |
| 7.143 | H | H | CH₃ | CH₃ | Cl | Cl | SO₂ | 0 |
| 7.144 | H | H | CH₃ | CH₃ | Cl | Cl | SO₂ | 2 |
| 7.145 | H | H | H | H | CH₃ | CH₃ | SO₂ | 0 |
| 7.146 | H | H | H | H | CH₃ | CH₃ | SO₂ | 2 |
| 7.147 | CH₃ | CH₃ | H | H | CH₃ | CH₃ | SO₂ | 0 |
| 7.148 | CH₃ | CH₃ | H | H | CH₃ | CH₃ | SO₂ | 2 |
| 7.149 | H | H | H | CH₃ | CH₃ | CH₃ | SO₂ | 0 |
| 7.150 | H | H | H | CH₃ | CH₃ | CH₃ | SO₂ | 2 |
| 7.151 | H | H | CH₃ | CH₃ | CH₃ | CH₃ | SO₂ | 0 |
| 7.152 | H | H | CH₃ | CH₃ | CH₃ | CH₃ | SO₂ | 2 |
| 7.153 | H | H | H | H | NO₂ | H | SO₂ | 0 |
| 7.154 | H | H | H | H | NO₂ | H | SO₂ | 2 |
| 7.155 | CH₃ | CH₃ | H | H | NO₂ | H | SO₂ | 0 |
| 7.156 | CH₃ | CH₃ | H | H | NO₂ | H | SO₂ | 2 |
| 7.157 | H | H | H | CH₃ | NO₂ | H | SO₂ | 0 |
| 7.158 | H | H | H | CH₃ | NO₂ | H | SO₂ | 2 |
| 7.159 | H | H | CH₃ | CH₃ | NO₂ | H | SO₂ | 0 |
| 7.160 | H | H | CH₃ | CH₃ | NO₂ | H | SO₂ | 2 |
| 7.161 | H | H | H | H | OCH₃ | H | SO₂ | 0 |
| 7.162 | H | H | H | H | OCH₃ | H | SO₂ | 2 |
| 7.163 | CH₃ | CH₃ | H | H | OCH₃ | H | SO₂ | 0 |
| 7.164 | CH₃ | CH₃ | H | H | OCH₃ | H | SO₂ | 2 |
| 7.165 | H | H | H | CH₃ | OCH₃ | H | SO₂ | 0 |
| 7.166 | H | H | H | CH₃ | OCH₃ | H | SO₂ | 2 |
| 7.167 | H | H | CH₃ | CH₃ | OCH₃ | H | SO₂ | 0 |

TABLE 3-continued

| No. | R⁵ | R⁶ | R⁷ | R⁸ | M | L | X | n |
|---|---|---|---|---|---|---|---|---|
| 7.168 | H | H | CH$_3$ | CH$_3$ | OCH$_3$ | H | SO$_2$ | 2 |

TABLE 4

| No. | R⁵ | R⁶ | R⁷ | R⁸ | L | M | X | n |
|---|---|---|---|---|---|---|---|---|
| 4.1 | H | H | H | H | CH$_3$ | H | O | 0 |
| 4.2 | H | H | H | H | CH$_3$ | H | O | 2 |
| 4.3 | CH$_3$ | CH$_3$ | H | H | CH$_3$ | H | O | 0 |
| 4.4 | CH$_3$ | CH$_3$ | H | H | CH$_3$ | H | O | 2 |
| 4.5 | H | H | H | CH$_3$ | CH$_3$ | H | O | 0 |
| 4.6 | H | H | H | CH$_3$ | CH$_3$ | H | O | 2 |
| 4.7 | H | H | CH$_3$ | CH$_3$ | CH$_3$ | H | O | 0 |
| 4.8 | H | H | CH$_3$ | CH$_3$ | CH$_3$ | H | O | 2 |
| 4.9 | H | H | H | H | Cl | H | O | 0 |
| 4.10 | H | H | H | H | Cl | H | O | 2 |
| 4.11 | CH$_3$ | CH$_3$ | H | H | Cl | H | O | 0 |
| 4.12 | CH$_3$ | CH$_3$ | H | H | Cl | H | O | 2 |
| 4.13 | H | H | H | CH$_3$ | Cl | H | O | 0 |
| 4.14 | H | H | H | CH$_3$ | Cl | H | O | 2 |
| 4.15 | H | H | CH$_3$ | CH$_3$ | Cl | H | O | 0 |
| 4.16 | H | H | CH$_3$ | CH$_3$ | Cl | H | O | 2 |
| 4.17 | H | H | H | H | Cl | Cl | O | 0 |
| 4.18 | H | H | H | H | Cl | Cl | O | 2 |
| 4.19 | CH$_3$ | CH$_3$ | H | H | Cl | Cl | O | 0 |
| 4.20 | CH$_3$ | CH$_3$ | H | H | Cl | Cl | O | 2 |
| 4.21 | H | H | H | CH$_3$ | Cl | Cl | O | 0 |
| 4.22 | H | H | H | CH$_3$ | Cl | Cl | O | 2 |
| 4.23 | H | H | CH$_3$ | CH$_3$ | Cl | Cl | O | 0 |
| 4.24 | H | H | CH$_3$ | CH$_3$ | Cl | Cl | O | 2 |
| 4.25 | H | H | H | H | CH$_3$ | CH$_3$ | O | 0 |
| 4.26 | H | H | H | H | CH$_3$ | CH$_3$ | O | 2 |
| 4.27 | CH$_3$ | CH$_3$ | H | H | CH$_3$ | CH$_3$ | O | 0 |
| 4.28 | CH$_3$ | CH$_3$ | H | H | CH$_3$ | CH$_3$ | O | 2 |
| 4.29 | H | H | H | CH$_3$ | CH$_3$ | CH$_3$ | O | 0 |
| 4.30 | H | H | H | CH$_3$ | CH$_3$ | CH$_3$ | O | 2 |
| 4.31 | H | H | CH$_3$ | CH$_3$ | CH$_3$ | CH$_3$ | O | 0 |
| 4.32 | H | H | CH$_3$ | CH$_3$ | CH$_3$ | CH$_3$ | O | 2 |
| 4.33 | H | H | H | H | CH$_3$ | H | S | 0 |
| 4.34 | H | H | H | H | CH$_3$ | H | S | 2 |
| 4.35 | CH$_3$ | CH$_3$ | H | H | CH$_3$ | H | S | 0 |
| 4.36 | CH$_3$ | CH$_3$ | H | H | CH$_3$ | H | S | 2 |
| 4.37 | H | H | H | CH$_3$ | CH$_3$ | H | S | 0 |
| 4.38 | H | H | H | CH$_3$ | CH$_3$ | H | S | 2 |
| 4.39 | H | H | CH$_3$ | CH$_3$ | CH$_3$ | H | S | 0 |
| 4.40 | H | H | CH$_3$ | CH$_3$ | CH$_3$ | H | S | 2 |
| 4.41 | H | H | H | H | Cl | H | S | 0 |
| 4.42 | H | H | H | H | Cl | H | S | 2 |
| 4.43 | CH$_3$ | CH$_3$ | H | H | Cl | H | S | 0 |
| 4.44 | CH$_3$ | CH$_3$ | H | H | Cl | H | S | 2 |
| 4.45 | H | H | H | CH$_3$ | Cl | H | S | 0 |
| 4.46 | H | H | H | CH$_3$ | Cl | H | S | 2 |
| 4.47 | H | H | CH$_3$ | CH$_3$ | Cl | H | S | 0 |
| 4.48 | H | H | CH$_3$ | CH$_3$ | Cl | H | S | 2 |
| 4.49 | H | H | H | H | Cl | Cl | S | 0 |
| 4.50 | H | H | H | H | Cl | Cl | S | 2 |
| 4.51 | CH$_3$ | CH$_3$ | H | H | Cl | Cl | S | 0 |
| 4.52 | CH$_3$ | CH$_3$ | H | H | Cl | Cl | S | 2 |
| 4.53 | H | H | H | CH$_3$ | Cl | Cl | S | 0 |
| 4.54 | H | H | H | CH$_3$ | Cl | Cl | S | 2 |
| 4.55 | H | H | CH$_3$ | CH$_3$ | Cl | Cl | S | 0 |
| 4.56 | H | H | CH$_3$ | CH$_3$ | Cl | Cl | S | 2 |
| 4.57 | H | H | H | H | CH$_3$ | CH$_3$ | S | 0 |
| 4.58 | 14 | H | H | H | CH$_3$ | CH$_3$ | S | 2 |
| 4.59 | CH$_3$ | CH$_3$ | H | H | CH$_3$ | CH$_3$ | S | 0 |
| 4.60 | CH$_3$ | CH$_3$ | H | H | CH$_3$ | CH$_3$ | S | 2 |
| 4.61 | H | H | H | CH$_3$ | CH$_3$ | CH$_3$ | S | 0 |
| 4.62 | H | H | H | CH$_3$ | CH$_3$ | CH$_3$ | S | 2 |
| 4.63 | H | H | CH$_3$ | CH$_3$ | CH$_3$ | CH$_3$ | S | 0 |
| 4.64 | H | H | CH$_3$ | CH$_3$ | CH$_3$ | CH$_3$ | S | 2 |
| 4.65 | H | H | H | H | CH$_3$ | H | SO$_2$ | 0 |
| 4.66 | H | H | H | H | CH$_3$ | H | SO$_2$ | 2 |
| 4.67 | CH$_3$ | CH$_3$ | H | H | CH$_3$ | H | SO$_2$ | 0 |
| 4.68 | CH$_3$ | CH$_3$ | H | H | CH$_3$ | H | SO$_2$ | 2 |
| 4.69 | H | H | H | CH$_3$ | CH$_3$ | H | SO$_2$ | 0 |
| 4.70 | H | H | H | CH$_3$ | CH$_3$ | H | SO$_2$ | 2 |
| 4.71 | H | H | CH$_3$ | CH$_3$ | CH$_3$ | H | SO$_2$ | 0 |
| 4.72 | H | H | CH$_3$ | CH$_3$ | CH$_3$ | H | SO$_2$ | 2 |
| 4.73 | H | H | H | H | Cl | H | SO$_2$ | 0 |
| 4.74 | H | H | H | H | Cl | H | SO$_2$ | 2 |
| 4.75 | CH$_3$ | CH$_3$ | H | H | Cl | H | SO$_2$ | 0 |
| 4.76 | CH$_3$ | CH$_3$ | H | H | Cl | H | SO$_2$ | 2 |
| 4.77 | H | H | H | CH$_3$ | Cl | H | SO$_2$ | 0 |
| 4.78 | H | H | H | CH$_3$ | Cl | H | SO$_2$ | 2 |
| 4.79 | H | H | CH$_3$ | CH$_3$ | Cl | H | SO$_2$ | 0 |
| 4.80 | H | H | CH$_3$ | CH$_3$ | Cl | H | SO$_2$ | 2 |
| 4.81 | H | H | H | H | Cl | Cl | SO$_2$ | 0 |
| 4.82 | H | H | H | H | Cl | Cl | SO$_2$ | 2 |
| 4.83 | CH$_3$ | CH$_3$ | H | H | Cl | Cl | SO$_2$ | 0 |
| 4.84 | CH$_3$ | CH$_3$ | H | H | Cl | Cl | SO$_2$ | 2 |
| 4.85 | H | H | H | CH$_3$ | Cl | Cl | SO$_2$ | 0 |
| 4.86 | H | H | H | CH$_3$ | Cl | Cl | SO$_2$ | 2 |
| 4.87 | H | H | CH$_3$ | CH$_3$ | Cl | Cl | SO$_2$ | 0 |
| 4.88 | H | H | CH$_3$ | CH$_3$ | Cl | Cl | SO$_2$ | 2 |
| 4.89 | H | H | H | H | CH$_3$ | CH$_3$ | SO$_2$ | 0 |
| 4.90 | H | H | H | H | CH$_3$ | CH$_3$ | SO$_2$ | 2 |
| 4.91 | CH$_3$ | CH$_3$ | H | H | CH$_3$ | CH$_3$ | SO$_2$ | 0 |
| 4.92 | CH$_3$ | CH$_3$ | H | H | CH$_3$ | CH$_3$ | SO$_2$ | 2 |
| 4.93 | H | H | H | CH$_3$ | CH$_3$ | CH$_3$ | SO$_2$ | 0 |
| 4.94 | H | H | H | CH$_3$ | CH$_3$ | CH$_3$ | SO$_2$ | 2 |
| 4.95 | H | H | CH$_3$ | CH$_3$ | CH$_3$ | CH$_3$ | SO$_2$ | 0 |
| 4.96 | H | H | CH$_3$ | CH$_3$ | CH$_3$ | CH$_3$ | SO$_2$ | 2 |

TABLE 5

[Structure: cyclohexanedione-hydroxy ring with R5, R6, R7, R8 substituents connected via C(=O) to a benzothiazine/benzoxazine ring bearing M, L, X, R1, R2, R3, R4, (O)n substituents]

| No. | R⁵ | R⁶ | R⁷ | R⁸ | R¹ | R² | R³ | R⁴ | M | L | X | n |
|---|---|---|---|---|---|---|---|---|---|---|---|---|
| 5.1 | H | H | H | H | H | H | CH₃ | H | H | H | O | 0 |
| 5.2 | H | H | H | H | H | H | CH₃ | H | H | H | O | 2 |
| 5.3 | CH₃ | CH₃ | H | H | H | H | CH₃ | H | H | H | O | 0 |
| 5.4 | CH₃ | CH₃ | H | H | H | H | CH₃ | H | H | H | O | 2 |
| 5.5 | H | H | H | CH₃ | H | H | CH₃ | H | H | H | O | 0 |
| 5.6 | H | H | H | CH₃ | H | H | CH₃ | H | H | H | O | 2 |
| 5.7 | H | H | CH₃ | CH₃ | H | H | CH₃ | H | H | H | O | 0 |
| 5.8 | H | H | CH₃ | CH₃ | H | H | CH₃ | H | H | H | O | 2 |
| 5.9 | H | H | H | H | H | H | CH₃ | H | CH₃ | H | O | 0 |
| 5.10 | H | H | H | H | H | H | CH₃ | H | CH₃ | H | O | 2 |
| 5.11 | CH₃ | CH₃ | H | H | H | H | CH₃ | H | CH₃ | H | O | 0 |
| 5.12 | CH₃ | CH₃ | H | H | H | H | CH₃ | H | CH₃ | H | O | 2 |
| 5.13 | H | H | H | CH₃ | H | H | CH₃ | H | CH₃ | H | O | 0 |
| 5.14 | H | H | H | CH₃ | H | H | CH₃ | H | CH₃ | H | O | 2 |
| 5.15 | H | H | CH₃ | CH₃ | H | H | CH₃ | H | CH₃ | H | O | 0 |
| 5.16 | H | H | CH₃ | CH₃ | H | H | CH₃ | H | CH₃ | H | O | 2 |
| 5.17 | H | H | H | H | H | H | CH₃ | H | Cl | H | O | 0 |
| 5.18 | H | H | H | H | H | H | CH₃ | H | Cl | H | O | 2 |
| 5.19 | CH₃ | CH₃ | H | H | H | H | CH₃ | H | Cl | H | O | 0 |
| 5.20 | CH₃ | CH₃ | H | H | H | H | CH₃ | H | Cl | H | O | 2 |
| 5.21 | H | H | H | CH₃ | H | H | CH₃ | H | Cl | H | O | 0 |
| 5.22 | H | H | H | CH₃ | H | H | CH₃ | H | Cl | H | O | 2 |
| 5.23 | H | H | CH₃ | CH₃ | H | H | CH₃ | H | Cl | H | O | 0 |
| 5.24 | H | H | CH₃ | CH₃ | H | H | CH₃ | H | Cl | H | O | 2 |
| 5.25 | H | H | H | H | H | H | CH₃ | H | Cl | Cl | O | 0 |
| 5.26 | H | H | H | H | H | H | CH₃ | H | Cl | Cl | O | 2 |
| 5.27 | CH₃ | CH₃ | H | H | H | H | CH₃ | H | Cl | Cl | O | 0 |
| 5.28 | CH₃ | CH₃ | H | H | H | H | CH₃ | H | Cl | Cl | O | 2 |
| 5.29 | H | H | H | CH₃ | H | H | CH₃ | H | Cl | Cl | O | 0 |
| 5.30 | H | H | H | CH₃ | H | H | CH₃ | H | Cl | Cl | O | 2 |
| 5.31 | H | H | CH₃ | CH₃ | H | H | CH₃ | H | Cl | Cl | O | 0 |
| 5.32 | H | H | CH₃ | CH₃ | H | H | CH₃ | H | Cl | Cl | O | 2 |
| 5.33 | H | H | H | H | H | H | CH₃ | H | CH₃ | CH₃ | O | 0 |
| 5.34 | H | H | H | H | H | H | CH₃ | H | CH₃ | CH₃ | O | 2 |
| 5.35 | CH₃ | CH₃ | H | H | H | H | CH₃ | H | CH₃ | CH₃ | O | 0 |
| 5.36 | CH₃ | CH₃ | H | H | H | H | CH₃ | H | CH₃ | CH₃ | O | 2 |
| 5.37 | H | H | H | CH₃ | H | H | CH₃ | H | CH₃ | CH₃ | O | 0 |
| 5.38 | H | H | H | CH₃ | H | H | CH₃ | H | CH₃ | CH₃ | O | 2 |
| 5.39 | H | H | CH₃ | CH₃ | H | H | CH₃ | H | CH₃ | CH₃ | O | 0 |
| 5.40 | H | H | CH₃ | CH₃ | H | H | CH₃ | H | CH₃ | CH₃ | O | 2 |
| 5.41 | H | H | H | H | H | H | CH₃ | H | OCH₃ | H | O | 0 |
| 5.42 | H | H | H | H | H | H | CH₃ | H | OCH₃ | H | O | 2 |
| 5.43 | CH₃ | CH₃ | H | H | H | H | CH₃ | H | OCH₃ | H | O | 0 |
| 5.44 | CH₃ | CH₃ | H | H | H | H | CH₃ | H | OCH₃ | H | O | 2 |
| 5.45 | H | H | H | CH₃ | H | H | CH₃ | H | OCH₃ | H | O | 0 |
| 5.46 | H | H | H | CH₃ | H | H | CH₃ | H | OCH₃ | H | O | 2 |
| 5.47 | H | H | CH₃ | CH₃ | H | H | CH₃ | H | OCH₃ | H | O | 0 |
| 5.48 | H | H | CH₃ | CH₃ | H | H | CH₃ | H | OCH₃ | H | O | 2 |
| 5.49 | H | H | H | H | H | H | CH₃ | H | H | H | S | 0 |
| 5.50 | H | H | H | H | H | H | CH₃ | H | H | H | S | 2 |
| 5.51 | CH₃ | CH₃ | H | H | H | H | CH₃ | H | H | H | S | 0 |
| 5.52 | CH₃ | CH₃ | H | H | H | H | CH₃ | H | H | H | S | 2 |
| 5.53 | H | H | H | CH₃ | H | H | CH₃ | H | H | H | S | 0 |
| 5.54 | H | H | H | CH₃ | H | H | CH₃ | H | H | H | S | 2 |
| 5.55 | H | H | CH₃ | CH₃ | H | H | CH₃ | H | H | H | S | 0 |
| 5.56 | H | H | CH₃ | CH₃ | H | H | CH₃ | H | H | H | S | 2 |
| 5.57 | H | H | H | H | H | H | CH₃ | H | CH₃ | H | S | 0 |
| 5.58 | H | H | H | H | H | H | CH₃ | H | CH₃ | H | S | 2 |
| 5.59 | CH₃ | CH₃ | H | H | H | H | CH₃ | H | CH₃ | H | S | 0 |
| 5.60 | CH₃ | CH₃ | H | H | H | H | CH₃ | H | CH₃ | H | S | 2 |
| 5.61 | H | H | H | CH₃ | H | H | CH₃ | H | CH₃ | H | S | 0 |
| 5.62 | H | H | H | CH₃ | H | H | CH₃ | H | CH₃ | H | S | 2 |
| 5.63 | H | H | CH₃ | CH₃ | H | H | CH₃ | H | CH₃ | H | S | 0 |
| 5.64 | H | H | CH₃ | CH₃ | H | H | CH₃ | H | CH₃ | H | S | 2 |
| 5.65 | H | H | H | H | H | H | CH₃ | H | Cl | H | S | 0 |
| 5.66 | H | H | H | H | H | H | CH₃ | H | Cl | H | S | 2 |

TABLE 5-continued

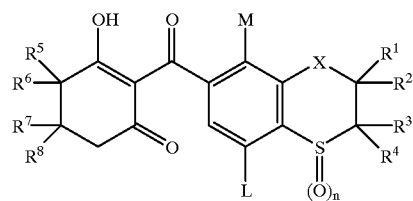

| No. | R⁵ | R⁶ | R⁷ | R⁸ | R¹ | R² | R³ | R⁴ | M | L | X | n |
|---|---|---|---|---|---|---|---|---|---|---|---|---|
| 5.67 | CH₃ | CH₃ | H | H | H | H | CH₃ | H | Cl | H | S | 0 |
| 5.68 | CH₃ | CH₃ | H | H | H | H | CH₃ | H | Cl | H | S | 2 |
| 5.69 | H | H | H | CH₃ | H | H | CH₃ | H | Cl | H | S | 0 |
| 5.70 | H | H | H | CH₃ | H | H | CH₃ | H | Cl | H | S | 2 |
| 5.71 | H | H | CH₃ | CH₃ | H | H | CH₃ | H | Cl | H | S | 0 |
| 5.72 | H | H | CH₃ | CH₃ | H | H | CH₃ | H | Cl | H | S | 2 |
| 5.73 | H | H | H | H | H | H | CH₃ | H | Cl | Cl | S | 0 |
| 5.74 | H | H | H | H | H | H | CH₃ | H | Cl | Cl | S | 2 |
| 5.75 | CH₃ | CH₃ | H | H | H | H | CH₃ | H | Cl | Cl | S | 0 |
| 5.76 | CH₃ | CH₃ | H | H | H | H | CH₃ | H | Cl | Cl | S | 2 |
| 5.77 | H | H | H | CH₃ | H | H | CH₃ | H | Cl | Cl | S | 0 |
| 5.78 | H | H | H | CH₃ | H | H | CH₃ | H | Cl | Cl | S | 2 |
| 5.79 | H | H | CH₃ | CH₃ | H | H | CH₃ | H | Cl | Cl | S | 0 |
| 5.80 | H | H | CH₃ | CH₃ | H | H | CH₃ | H | Cl | Cl | S | 2 |
| 5.81 | H | H | H | H | H | H | CH₃ | H | CH₃ | CH₃ | S | 0 |
| 5.82 | H | H | H | H | H | H | CH₃ | H | CH₃ | CH₃ | S | 2 |
| 5.83 | CH₃ | CH₃ | H | H | H | H | CH₃ | H | CH₃ | CH₃ | S | 0 |
| 5.84 | CH₃ | CH₃ | H | H | H | H | CH₃ | H | CH₃ | CH₃ | S | 2 |
| 5.85 | H | H | H | CH₃ | H | H | CH₃ | H | CH₃ | CH₃ | S | 0 |
| 5.86 | H | H | H | CH₃ | H | H | CH₃ | H | CH₃ | CH₃ | S | 2 |
| 5.87 | H | H | CH₃ | CH₃ | H | H | CH₃ | H | CH₃ | CH₃ | S | 0 |
| 5.88 | H | H | CH₃ | CH₃ | H | H | CH₃ | H | CH₃ | CH₃ | S | 2 |
| 5.89 | H | H | H | H | H | H | CH₃ | H | OCH₃ | H | S | 0 |
| 5.90 | H | H | H | H | H | H | CH₃ | H | OCH₃ | H | S | 2 |
| 5.91 | CH₃ | CH₃ | H | H | H | H | CH₃ | H | OCH₃ | H | S | 0 |
| 5.92 | CH₃ | CH₃ | H | H | H | H | CH₃ | H | OCH₃ | H | S | 2 |
| 5.93 | H | H | H | CH₃ | H | H | CH₃ | H | OCH₃ | H | S | 0 |
| 5.94 | H | H | H | CH₃ | H | H | CH₃ | H | OCH₃ | H | S | 2 |
| 5.95 | H | H | CH₃ | CH₃ | H | H | CH₃ | H | OCH₃ | H | S | 0 |
| 5.96 | H | H | CH₃ | CH₃ | H | H | CH₃ | H | OCH₃ | H | S | 2 |
| 5.97 | H | H | H | H | H | H | CH₃ | H | H | H | SO₂ | 0 |
| 5.98 | H | H | H | H | H | H | CH₃ | H | H | H | SO₂ | 2 |
| 5.99 | CH₃ | CH₃ | H | H | H | H | CH₃ | H | H | H | SO₂ | 0 |
| 5.100 | CH₃ | CH₃ | H | H | H | H | CH₃ | H | H | H | SO₂ | 2 |
| 5.101 | H | H | H | CH₃ | H | H | CH₃ | H | H | H | SO₂ | 0 |
| 5.102 | H | H | H | CH₃ | H | H | CH₃ | H | H | H | SO₂ | 2 |
| 5.103 | H | H | CH₃ | CH₃ | H | H | CH₃ | H | H | H | SO₂ | 0 |
| 5.104 | H | H | CH₃ | CH₃ | H | H | CH₃ | H | H | H | SO₂ | 2 |
| 5.105 | H | H | H | H | H | H | CH₃ | H | CH₃ | H | SO₂ | 0 |
| 5.106 | H | H | H | H | H | H | CH₃ | H | CH₃ | H | SO₂ | 2 |
| 5.107 | CH₃ | CH₃ | H | H | H | H | CH₃ | H | CH₃ | H | SO₂ | 0 |
| 5.108 | CH₃ | CH₃ | H | H | H | H | CH₃ | H | CH₃ | H | SO₂ | 2 |
| 5.109 | H | H | H | CH₃ | H | H | CH₃ | H | CH₃ | H | SO₂ | 0 |
| 5.110 | H | H | H | CH₃ | H | H | CH₃ | H | CH₃ | H | SO₂ | 2 |
| 5.111 | H | H | CH₃ | CH₃ | H | H | CH₃ | H | CH₃ | H | SO₂ | 0 |
| 5.112 | H | H | CH₃ | CH₃ | H | H | CH₃ | H | CH₃ | H | SO₂ | 2 |
| 5.113 | H | H | H | H | H | H | CH₃ | H | Cl | H | SO₂ | 0 |
| 5.114 | H | H | H | H | H | H | CH₃ | H | Cl | H | SO₂ | 2 |
| 5.115 | CH₃ | CH₃ | H | H | H | H | CH₃ | H | Cl | H | SO₂ | 0 |
| 5.116 | CH₃ | CH₃ | H | H | H | H | CH₃ | H | Cl | H | SO₂ | 2 |
| 5.117 | H | H | H | CH₃ | H | H | CH₃ | H | Cl | H | SO₂ | 0 |
| 5.118 | H | H | H | CH₃ | H | H | CH₃ | H | Cl | H | SO₂ | 2 |
| 5.119 | H | H | CH₃ | CH₃ | H | H | CH₃ | H | Cl | H | SO₂ | 0 |
| 5.120 | H | H | CH₃ | CH₃ | H | H | CH₃ | H | Cl | H | SO₂ | 2 |
| 5.121 | H | H | H | H | H | H | CH₃ | H | Cl | Cl | SO₂ | 0 |
| 5.122 | H | H | H | H | H | H | CH₃ | H | Cl | Cl | SO₂ | 2 |
| 5.123 | CH₃ | CH₃ | H | H | H | H | CH₃ | H | Cl | Cl | SO₂ | 0 |
| 5.124 | CH₃ | CH₃ | H | H | H | H | CH₃ | H | Cl | Cl | SO₂ | 2 |
| 5.125 | H | H | H | CH₃ | H | H | CH₃ | H | Cl | Cl | SO₂ | 0 |
| 5.126 | H | H | H | CH₃ | H | H | CH₃ | H | Cl | Cl | SO₂ | 2 |
| 5.127 | H | H | CH₃ | CH₃ | H | H | CH₃ | H | Cl | Cl | SO₂ | 0 |
| 5.128 | H | H | CH₃ | CH₃ | H | H | CH₃ | H | Cl | Cl | SO₂ | 2 |
| 5.129 | H | H | H | H | H | H | CH₃ | H | CH₃ | CH₃ | SO₂ | 0 |
| 5.130 | H | H | H | H | H | H | CH₃ | H | CH₃ | CH₃ | SO₂ | 2 |
| 5.131 | CH₃ | CH₃ | H | H | H | H | CH₃ | H | CH₃ | CH₃ | SO₂ | 0 |
| 5.132 | CH₃ | CH₃ | H | H | H | H | CH₃ | H | CH₃ | CH₃ | SO₂ | 2 |

TABLE 5-continued

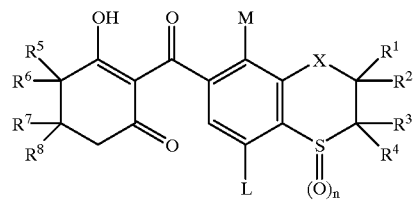

| No. | R⁵ | R⁶ | R⁷ | R⁸ | R¹ | R² | R³ | R⁴ | M | L | X | n |
|---|---|---|---|---|---|---|---|---|---|---|---|---|
| 5.133 | H | H | H | CH₃ | H | H | CH₃ | H | CH₃ | CH₃ | SO₂ | 0 |
| 5.134 | H | H | H | CH₃ | H | H | CH₃ | H | CH₃ | CH₃ | SO₂ | 2 |
| 5.135 | H | H | CH₃ | CH₃ | H | H | CH₃ | H | CH₃ | CH₃ | SO₂ | 0 |
| 5.136 | H | H | CH₃ | CH₃ | H | H | CH₃ | H | CH₃ | CH₃ | SO₂ | 2 |
| 5.137 | H | H | H | H | H | H | CH₃ | CH₃ | H | H | O | 0 |
| 5.138 | H | H | H | H | H | H | CH₃ | CH₃ | H | H | O | 2 |
| 5.139 | CH₃ | CH₃ | H | H | H | H | CH₃ | CH₃ | H | H | O | 0 |
| 5.140 | CH₃ | CH₃ | H | H | H | H | CH₃ | CH₃ | H | H | O | 2 |
| 5.141 | H | H | H | CH₃ | H | H | CH₃ | CH₃ | H | H | O | 0 |
| 5.142 | H | H | H | CH₃ | H | H | CH₃ | CH₃ | H | H | O | 2 |
| 5.143 | H | H | CH₃ | CH₃ | H | H | CH₃ | CH₃ | H | H | O | 0 |
| 5.144 | H | H | CH₃ | CH₃ | H | H | CH₃ | CH₃ | H | H | O | 2 |
| 5.145 | H | H | H | H | H | H | CH₃ | CH₃ | CH₃ | H | O | 0 |
| 5.146 | H | H | H | H | H | H | CH₃ | CH₃ | CH₃ | H | O | 2 |
| 5.147 | CH₃ | CH₃ | H | H | H | H | CH₃ | CH₃ | CH₃ | H | O | 0 |
| 5.148 | CH₃ | CH₃ | H | H | H | H | CH₃ | CH₃ | CH₃ | H | O | 2 |
| 5.149 | H | H | H | CH₃ | H | H | CH₃ | CH₃ | CH₃ | H | O | 0 |
| 5.150 | H | H | H | CH₃ | H | H | CH₃ | CH₃ | CH₃ | H | O | 2 |
| 5.151 | H | H | CH₃ | CH₃ | H | H | CH₃ | CH₃ | CH₃ | H | O | 0 |
| 5.152 | H | H | CH₃ | CH₃ | H | H | CH₃ | CH₃ | CH₃ | H | O | 2 |
| 5.153 | H | H | H | H | H | H | CH₃ | CH₃ | Cl | H | O | 0 |
| 5.154 | H | H | H | H | H | H | CH₃ | CH₃ | Cl | H | O | 2 |
| 5.155 | CH₃ | CH₃ | H | H | H | H | CH₃ | CH₃ | Cl | H | O | 0 |
| 5.156 | CH₃ | CH₃ | H | H | H | H | CH₃ | CH₃ | Cl | H | O | 2 |
| 5.157 | H | H | H | CH₃ | H | H | CH₃ | CH₃ | Cl | H | O | 0 |
| 5.158 | H | H | H | CH₃ | H | H | CH₃ | CH₃ | Cl | H | O | 2 |
| 5.159 | H | H | CH₃ | CH₃ | H | H | CH₃ | CH₃ | Cl | H | O | 0 |
| 5.160 | H | H | CH₃ | CH₃ | H | H | CH₃ | CH₃ | Cl | H | O | 2 |
| 5.161 | H | H | H | H | H | H | CH₃ | CH₃ | Cl | Cl | O | 0 |
| 5.162 | H | H | H | H | H | H | CH₃ | CH₃ | Cl | Cl | O | 2 |
| 5.163 | CH₃ | CH₃ | H | H | H | H | CH₃ | CH₃ | Cl | Cl | O | 0 |
| 5.164 | CH₃ | CH₃ | H | H | H | H | CH₃ | CH₃ | Cl | Cl | O | 2 |
| 5.165 | H | H | H | CH₃ | H | H | CH₃ | CH₃ | Cl | Cl | O | 0 |
| 5.166 | H | H | H | CH₃ | H | H | CH₃ | CH₃ | Cl | Cl | O | 2 |
| 5.167 | H | H | CH₃ | CH₃ | H | H | CH₃ | CH₃ | Cl | Cl | O | 0 |
| 5.168 | H | H | CH₃ | CH₃ | H | H | CH₃ | CH₃ | Cl | Cl | O | 2 |
| 5.169 | H | H | H | H | H | H | CH₃ | CH₃ | CH₃ | CH₃ | O | 0 |
| 5.170 | H | H | H | H | H | H | CH₃ | CH₃ | CH₃ | CH₃ | O | 2 |
| 5.171 | CH₃ | CH₃ | H | H | H | H | CH₃ | CH₃ | CH₃ | CH₃ | O | 0 |
| 5.172 | CH₃ | CH₃ | H | H | H | H | CH₃ | CH₃ | CH₃ | CH₃ | O | 2 |
| 5.173 | H | H | H | CH₃ | H | H | CH₃ | CH₃ | CH₃ | CH₃ | O | 0 |
| 5.174 | H | H | H | CH₃ | H | H | CH₃ | CH₃ | CH₃ | CH₃ | O | 2 |
| 5.175 | H | H | CH₃ | CH₃ | H | H | CH₃ | CH₃ | CH₃ | CH₃ | O | 0 |
| 5.176 | H | H | CH₃ | CH₃ | H | H | CH₃ | CH₃ | CH₃ | CH₃ | O | 2 |
| 5.177 | H | H | H | H | H | H | CH₃ | CH₃ | OCH₃ | H | O | 0 |
| 5.178 | H | H | H | H | H | H | CH₃ | CH₃ | OCH₃ | H | O | 2 |
| 5.179 | CH₃ | CH₃ | H | H | H | H | CH₃ | CH₃ | OCH₃ | H | O | 0 |
| 5.180 | CH₃ | CH₃ | H | H | H | H | CH₃ | CH₃ | OCH₃ | H | O | 2 |
| 5.181 | H | H | H | CH₃ | H | H | CH₃ | CH₃ | OCH₃ | H | O | 0 |
| 5.182 | H | H | H | CH₃ | H | H | CH₃ | CH₃ | OCH₃ | H | O | 2 |
| 5.183 | H | H | CH₃ | CH₃ | H | H | CH₃ | CH₃ | OCH₃ | H | O | 0 |
| 5.184 | H | H | CH₃ | CH₃ | H | H | CH₃ | CH₃ | OCH₃ | H | O | 2 |
| 5.185 | H | H | H | H | H | H | CH₃ | CH₃ | H | H | S | 0 |
| 5.186 | H | H | H | H | H | H | CH₃ | CH₃ | H | H | S | 2 |
| 5.187 | CH₃ | CH₃ | H | H | H | H | CH₃ | CH₃ | H | H | S | 0 |
| 5.188 | CH₃ | CH₃ | H | H | H | H | CH₃ | CH₃ | H | H | S | 2 |
| 5.189 | H | H | H | CH₃ | H | H | CH₃ | CH₃ | H | H | S | 0 |
| 5.190 | H | H | H | CH₃ | H | H | CH₃ | CH₃ | H | H | S | 2 |
| 5.191 | H | H | CH₃ | CH₃ | H | H | CH₃ | CH₃ | H | H | S | 0 |
| 5.192 | H | H | CH₃ | CH₃ | H | H | CH₃ | CH₃ | H | H | S | 2 |
| 5.193 | H | H | H | H | H | H | CH₃ | CH₃ | CH₃ | H | S | 0 |
| 5.194 | H | H | H | H | H | H | CH₃ | CH₃ | CH₃ | H | S | 2 |
| 5.195 | CH₃ | CH₃ | H | H | H | H | CH₃ | CH₃ | CH₃ | H | S | 0 |
| 5.196 | CH₃ | CH₃ | H | H | H | H | CH₃ | CH₃ | CH₃ | H | S | 2 |
| 5.197 | H | H | H | CH₃ | H | H | CH₃ | CH₃ | CH₃ | H | S | 0 |
| 5.198 | H | H | H | CH₃ | H | A | CH₃ | CH₃ | CH₃ | H | S | 2 |

TABLE 5-continued

Structure: cyclohexanedione with OH, connected via C=O to benzothiazine-type ring system with substituents R¹-R⁸, M, L, X, (O)ₙ

| No. | R⁵ | R⁶ | R⁷ | R⁸ | R¹ | R² | R³ | R⁴ | M | L | X | n |
|---|---|---|---|---|---|---|---|---|---|---|---|---|
| 5.199 | H | H | CH₃ | CH₃ | H | H | CH₃ | CH₃ | CH₃ | H | S | 0 |
| 5.200 | H | H | CH₃ | CH₃ | H | H | CH₃ | CH₃ | CH₃ | H | S | 2 |
| 5.201 | H | H | H | H | H | H | CH₃ | CH₃ | Cl | H | S | 0 |
| 5.202 | H | H | H | H | H | H | CH₃ | CH₃ | Cl | H | S | 2 |
| 5.203 | CH₃ | CH₃ | H | H | H | H | CH₃ | CH₃ | Cl | H | S | 0 |
| 5.204 | CH₃ | CH₃ | H | H | H | H | CH₃ | CH₃ | Cl | H | S | 2 |
| 5.205 | H | H | H | CH₃ | H | H | CH₃ | CH₃ | Cl | H | S | 0 |
| 5.206 | H | H | H | CH₃ | H | H | CH₃ | CH₃ | Cl | H | S | 2 |
| 5.207 | H | H | CH₃ | CH₃ | H | H | CH₃ | CH₃ | Cl | H | S | 0 |
| 5.208 | H | H | CH₃ | CH₃ | H | H | CH₃ | CH₃ | Cl | H | S | 2 |
| 5.209 | H | H | H | H | H | H | CH₃ | CH₃ | Cl | Cl | S | 0 |
| 5.210 | H | H | H | H | H | H | CH₃ | CH₃ | Cl | Cl | S | 2 |
| 5.211 | CH₃ | CH₃ | H | H | H | H | CH₃ | CH₃ | Cl | Cl | S | 0 |
| 5.212 | CH₃ | CH₃ | H | H | H | H | CH₃ | CH₃ | Cl | Cl | S | 2 |
| 5.213 | H | H | H | CH₃ | H | H | CH₃ | CH₃ | Cl | Cl | S | 0 |
| 5.214 | H | H | H | CH₃ | H | H | CH₃ | CH₃ | Cl | Cl | S | 2 |
| 5.215 | H | H | CH₃ | CH₃ | H | H | CH₃ | CH₃ | Cl | Cl | S | 0 |
| 5.216 | H | H | CH₃ | CH₃ | H | H | CH₃ | CH₃ | Cl | Cl | S | 2 |
| 5.217 | H | H | H | H | H | H | CH₃ | CH₃ | CH₃ | CH₃ | S | 0 |
| 5.218 | H | H | H | H | H | H | CH₃ | CH₃ | CH₃ | CH₃ | S | 2 |
| 5.219 | CH₃ | CH₃ | H | H | H | H | CH₃ | CH₃ | CH₃ | CH₃ | S | 0 |
| 5.220 | CH₃ | CH₃ | H | H | H | H | CH₃ | CH₃ | CH₃ | CH₃ | S | 2 |
| 5.221 | H | H | H | CH₃ | H | H | CH₃ | CH₃ | CH₃ | CH₃ | S | 0 |
| 5.222 | H | H | H | CH₃ | H | H | CH₃ | CH₃ | CH₃ | CH₃ | S | 2 |
| 5.223 | H | H | CH₃ | CH₃ | H | H | CH₃ | CH₃ | CH₃ | CH₃ | S | 0 |
| 5.224 | H | H | CH₃ | CH₃ | H | H | CH₃ | CH₃ | CH₃ | CH₃ | S | 2 |
| 5.225 | H | H | H | H | H | H | CH₃ | CH₃ | OCH₃ | H | S | 0 |
| 5.226 | H | H | H | H | H | H | CH₃ | CH₃ | OCH₃ | H | S | 2 |
| 5.227 | CH₃ | CH₃ | H | H | H | H | CH₃ | CH₃ | OCH₃ | H | S | 0 |
| 5.228 | CH₃ | CH₃ | H | H | H | H | CH₃ | CH₃ | OCH₃ | H | S | 2 |
| 5.229 | H | H | H | CH₃ | H | H | CH₃ | CH₃ | OCH₃ | H | S | 0 |
| 5.230 | H | H | H | CH₃ | H | H | CH₃ | CH₃ | OCH₃ | H | S | 2 |
| 5.231 | H | H | CH₃ | CH₃ | H | H | CH₃ | CH₃ | OCH₃ | H | S | 0 |
| 5.232 | H | H | CH₃ | CH₃ | H | H | CH₃ | CH₃ | OCH₃ | H | S | 2 |
| 5.233 | H | H | H | H | H | H | CH₃ | CH₃ | H | H | SO₂ | 0 |
| 5.234 | H | H | H | H | H | H | CH₃ | CH₃ | H | H | SO₂ | 2 |
| 5.235 | CH₃ | CH₃ | H | H | H | H | CH₃ | CH₃ | H | H | SO₂ | 0 |
| 5.236 | CH₃ | CH₃ | H | H | H | H | CH₃ | CH₃ | H | H | SO₂ | 2 |
| 5.237 | H | H | H | CH₃ | H | H | CH₃ | CH₃ | H | H | SO₂ | 0 |
| 5.238 | H | H | H | CH₃ | H | H | CH₃ | CH₃ | H | H | SO₂ | 2 |
| 5.239 | H | H | CH₃ | CH₃ | H | H | CH₃ | CH₃ | H | H | SO₂ | 0 |
| 5.240 | H | H | CH₃ | CH₃ | H | H | CH₃ | CH₃ | H | H | SO₂ | 2 |
| 5.241 | H | H | H | H | H | H | CH₃ | CH₃ | CH₃ | H | SO₂ | 0 |
| 5.242 | H | H | H | H | H | H | CH₃ | CH₃ | CH₃ | H | SO₂ | 2 |
| 5.243 | CH₃ | CH₃ | H | H | H | H | CH₃ | CH₃ | CH₃ | H | SO₂ | 0 |
| 5.244 | CH₃ | CH₃ | H | H | H | H | CH₃ | CH₃ | CH₃ | H | SO₂ | 2 |
| 5.245 | H | H | H | CH₃ | H | H | CH₃ | CH₃ | CH₃ | H | SO₂ | 0 |
| 5.246 | H | H | H | CH₃ | H | H | CH₃ | CH₃ | CH₃ | H | SO₂ | 2 |
| 5.247 | H | H | CH₃ | CH₃ | H | H | CH₃ | CH₃ | CH₃ | H | SO₂ | 0 |
| 5.248 | H | H | CH₃ | CH₃ | H | H | CH₃ | CH₃ | CH₃ | H | SO₂ | 2 |
| 5.249 | H | H | H | H | H | H | CH₃ | CH₃ | Cl | H | SO₂ | 0 |
| 5.250 | H | H | H | H | H | H | CH₃ | CH₃ | Cl | H | SO₂ | 2 |
| 5.251 | CH₃ | CH₃ | H | H | H | H | CH₃ | CH₃ | Cl | H | SO₂ | 0 |
| 5.252 | CH₃ | CH₃ | H | H | H | H | CH₃ | CH₃ | Cl | H | SO₂ | 2 |
| 5.253 | H | H | H | CH₃ | H | H | CH₃ | CH₃ | Cl | H | SO₂ | 0 |
| 5.254 | H | H | H | CH₃ | H | H | CH₃ | CH₃ | Cl | H | SO₂ | 2 |
| 5.255 | H | H | CH₃ | CH₃ | H | H | CH₃ | CH₃ | Cl | H | SO₂ | 0 |
| 5.256 | H | H | CH₃ | CH₃ | H | H | CH₃ | CH₃ | Cl | H | SO₂ | 2 |
| 5.257 | H | H | H | H | H | H | CH₃ | CH₃ | Cl | Cl | SO₂ | 0 |
| 5.258 | H | H | H | H | H | H | CH₃ | CH₃ | Cl | Cl | SO₂ | 2 |
| 5.259 | CH₃ | CH₃ | H | H | H | H | CH₃ | CH₃ | Cl | Cl | SO₂ | 0 |
| 5.260 | CH₃ | CH₃ | H | H | H | H | CH₃ | CH₃ | Cl | Cl | SO₂ | 2 |
| 5.261 | H | H | H | CH₃ | H | H | CH₃ | CH₃ | Cl | Cl | SO₂ | 0 |
| 5.262 | H | H | H | CH₃ | H | H | CH₃ | CH₃ | Cl | Cl | SO₂ | 2 |
| 5.263 | H | H | CH₃ | CH₃ | H | H | CH₃ | CH₃ | Cl | Cl | SO₂ | 0 |
| 5.264 | H | H | CH₃ | CH₃ | H | H | CH₃ | CH₃ | Cl | Cl | SO₂ | 2 |

TABLE 5-continued

| No. | R⁵ | R⁶ | R⁷ | R⁸ | R¹ | R² | R³ | R⁴ | M | L | X | n |
|---|---|---|---|---|---|---|---|---|---|---|---|---|
| 5.265 | H | H | H | H | H | H | CH₃ | CH₃ | CH₃ | CH₃ | SO₂ | 0 |
| 5.266 | H | H | H | H | H | H | CH₃ | CH₃ | CH₃ | CH₃ | SO₂ | 2 |
| 5.267 | CH₃ | CH₃ | H | H | H | H | CH₃ | CH₃ | CH₃ | CH₃ | SO₂ | 0 |
| 5.268 | CH₃ | CH₃ | H | H | H | H | CH₃ | CH₃ | CH₃ | CH₃ | SO₂ | 2 |
| 5.269 | H | H | H | CH₃ | H | H | CH₃ | CH₃ | CH₃ | CH₃ | SO₂ | 0 |
| 5.270 | H | H | H | CH₃ | H | H | CH₃ | CH₃ | CH₃ | CH₃ | SO₂ | 2 |
| 5.271 | H | H | CH₃ | CH₃ | H | H | CH₃ | CH₃ | CH₃ | CH₃ | SO₂ | 0 |
| 5.272 | H | H | CH₃ | CH₃ | H | H | CH₃ | CH₃ | CH₃ | CH₃ | SO₂ | 2 |
| 5.273 | H | H | H | H | H | CH₃ | H | CH₃ | H | H | O | 0 |
| 5.274 | H | H | H | H | H | CH₃ | H | CH₃ | H | H | O | 2 |
| 5.275 | CH₃ | CH₃ | H | H | H | CH₃ | H | CH₃ | H | H | O | 0 |
| 5.276 | CH₃ | CH₃ | H | H | H | CH | H | CH₃ | H | H | O | 2 |
| 5.277 | H | H | H | CH₃ | H | CH₃ | H | CH₃ | H | H | O | 0 |
| 5.278 | H | H | H | CH₃ | H | CH₃ | H | CH₃ | H | H | O | 2 |
| 5.279 | H | H | CH₃ | CH₃ | H | CH₃ | H | CH₃ | H | H | O | 0 |
| 5.280 | H | H | CH₃ | CH₃ | H | CH₃ | H | CH₃ | H | H | O | 2 |
| 5.281 | H | H | H | H | H | CH₃ | H | CH₃ | CH₃ | H | O | 0 |
| 5.282 | H | H | H | H | H | CH₃ | H | CH₃ | CH₃ | H | O | 2 |
| 5.283 | CH₃ | CH₃ | H | H | H | CH₃ | H | CH₃ | CH₃ | H | O | 0 |
| 5.284 | CH₃ | CH₃ | H | H | H | CH₃ | H | CH₃ | CH₃ | H | O | 2 |
| 5.285 | H | H | H | CH₃ | H | CH₃ | H | CH₃ | CH₃ | H | O | 0 |
| 5.286 | H | H | H | CH₃ | H | CH₃ | H | CH₃ | CH₃ | H | O | 2 |
| 5.287 | H | H | CH₃ | CH₃ | H | CH₃ | H | CH₃ | CH₃ | H | O | 0 |
| 5.288 | H | H | CH₃ | CH₃ | H | CH₃ | H | CH₃ | CH₃ | H | O | 2 |
| 5.289 | H | H | H | H | H | CH₃ | H | CH₃ | Cl | H | O | 0 |
| 5.290 | H | H | H | H | H | CH₃ | H | CH₃ | Cl | H | O | 2 |
| 5.291 | CH₃ | CH₃ | H | H | H | CH₃ | H | CH₃ | Cl | H | O | 0 |
| 5.292 | CH₃ | CH₃ | H | H | H | CH₃ | H | CH₃ | Cl | H | O | 2 |
| 5.293 | H | H | H | CH₃ | H | CH₃ | H | CH₃ | Cl | H | O | 0 |
| 5.294 | H | H | H | CH₃ | H | CH₃ | H | CH₃ | Cl | H | O | 2 |
| 5.295 | H | H | CH₃ | CH₃ | H | CH₃ | H | CH₃ | Cl | H | O | 0 |
| 5.296 | H | H | CH₃ | CH₃ | H | CH₃ | H | CH₃ | Cl | H | O | 2 |
| 5.297 | H | H | H | H | H | CH₃ | H | CH₃ | Cl | Cl | O | 0 |
| 5.298 | H | H | H | H | H | CH₃ | H | CH₃ | Cl | Cl | O | 2 |
| 5.299 | CH₃ | CH₃ | H | H | H | CH₃ | H | CH₃ | Cl | Cl | O | 0 |
| 5.300 | CH₃ | CH₃ | H | H | H | CH₃ | H | CH₃ | Cl | Cl | O | 2 |
| 5.301 | H | H | H | CH₃ | H | CH₃ | H | CH₃ | Cl | Cl | O | 0 |
| 5.302 | H | H | H | CH₃ | H | CH₃ | H | CH₃ | Cl | Cl | O | 2 |
| 5.303 | H | H | CH₃ | CH₃ | H | CH₃ | H | CH₃ | Cl | Cl | O | 0 |
| 5.304 | H | H | CH₃ | CH₃ | H | CH₃ | H | CH₃ | Cl | Cl | O | 2 |
| 5.305 | H | H | H | H | H | CH₃ | H | CH₃ | CH₃ | CH₃ | O | 0 |
| 5.306 | H | H | H | H | H | CH₃ | H | CH₃ | CH₃ | CH₃ | O | 2 |
| 5.307 | CH₃ | CH₃ | H | H | H | CH₃ | H | CH₃ | CH₃ | CH₃ | O | 0 |
| 5.308 | CH₃ | CH₃ | H | H | H | CH₃ | H | CH₃ | CH₃ | CH₃ | O | 2 |
| 5.309 | H | H | H | CH₃ | H | CH₃ | H | CH₃ | CH₃ | CH₃ | O | 0 |
| 5.310 | H | H | H | CH₃ | H | CH₃ | H | CH₃ | CH₃ | CH₃ | O | 2 |
| 5.311 | H | H | CH₃ | CH₃ | H | CH₃ | H | CH₃ | CH₃ | CH₃ | O | 0 |
| 5.312 | H | H | CH₃ | CH₃ | H | CH₃ | H | CH₃ | CH₃ | CH₃ | O | 2 |
| 5.313 | H | H | H | H | H | CH₃ | H | CH₃ | OCH₃ | H | O | 0 |
| 5.314 | H | H | H | H | H | CH₃ | H | CH₃ | OCH₃ | H | O | 2 |
| 5.315 | CH₃ | CH₃ | H | H | H | CH₃ | H | CH₃ | OCH₃ | H | O | 0 |
| 5.316 | CH₃ | CH₃ | H | H | H | CH₃ | H | CH₃ | OCH₃ | H | O | 2 |
| 5.317 | H | H | H | CH₃ | H | CH₃ | H | CH₃ | OCH₃ | H | O | 0 |
| 5.318 | H | H | H | CH₃ | H | CH₃ | H | CH₃ | OCH₃ | H | O | 2 |
| 5.319 | H | H | CH₃ | CH₃ | H | CH₃ | H | CH₃ | OCH₃ | H | O | 0 |
| 5.320 | H | H | CH₃ | CH₃ | H | CH₃ | H | CH₃ | OCH₃ | H | O | 2 |
| 5.321 | H | H | H | H | H | CH₃ | H | CH₃ | H | H | S | 0 |
| 5.322 | H | H | H | H | H | CH₃ | H | CH₃ | H | H | S | 2 |
| 5.323 | CH₃ | CH₃ | H | H | H | CH₃ | H | CH₃ | H | H | S | 0 |
| 5.324 | CH₃ | CH₃ | H | H | H | CH₃ | H | CH₃ | H | H | S | 2 |
| 5.325 | H | H | H | CH₃ | H | CH₃ | H | CH₃ | H | H | S | 0 |
| 5.326 | H | H | H | CH₃ | H | CH₃ | H | CH₃ | H | H | S | 2 |
| 5.327 | H | H | CH₃ | CH₃ | H | CH₃ | H | CH₃ | H | H | S | 0 |
| 5.328 | H | H | CH₃ | CH₃ | H | CH₃ | H | CH₃ | H | H | S | 2 |
| 5.329 | H | H | H | H | H | CH₃ | H | CH₃ | CH₃ | H | S | 0 |
| 5.330 | H | H | H | H | H | CH₃ | H | CH₃ | CH₃ | H | S | 2 |

TABLE 5-continued

| No. | R⁵ | R⁶ | R⁷ | R⁸ | R¹ | R² | R³ | R⁴ | M | L | X | n |
|---|---|---|---|---|---|---|---|---|---|---|---|---|
| 5.331 | CH₃ | CH₃ | H | H | H | CH₃ | H | CH₃ | CH₃ | H | S | 0 |
| 5.332 | CH₃ | CH₃ | H | H | H | CH₃ | H | CH₃ | CH₃ | H | S | 2 |
| 5.333 | H | H | H | CH₃ | H | CH₃ | H | CH₃ | CH₃ | H | S | 0 |
| 5.334 | H | H | H | CH₃ | H | CH₃ | H | CH₃ | CH₃ | H | S | 2 |
| 5.335 | H | H | CH₃ | CH₃ | H | CH₃ | H | CH₃ | CH₃ | H | S | 0 |
| 5.336 | H | H | CH₃ | CH₃ | H | CH₃ | H | CH₃ | CH₃ | H | S | 2 |
| 5.337 | H | H | H | H | H | CH₃ | H | CH₃ | Cl | H | S | 0 |
| 5.338 | H | H | H | H | H | CH₃ | H | CH₃ | Cl | H | S | 2 |
| 5.339 | CH₃ | CH₃ | H | H | H | CH₃ | H | CH₃ | Cl | H | S | 0 |
| 5.340 | CH₃ | CH₃ | H | H | H | CH₃ | H | CH₃ | Cl | H | S | 2 |
| 5.341 | H | H | H | CH₃ | H | CH₃ | H | CH₃ | Cl | H | S | 0 |
| 5.342 | H | H | H | CH₃ | H | CH₃ | H | CH₃ | Cl | H | S | 2 |
| 5.343 | H | H | CH₃ | CH₃ | H | CH₃ | H | CH₃ | Cl | H | S | 0 |
| 5.344 | H | H | CH₃ | CH₃ | H | CH₃ | H | CH₃ | Cl | H | S | 2 |
| 5.345 | H | H | H | H | H | CH₃ | H | CH₃ | Cl | Cl | S | 0 |
| 5.346 | H | H | H | H | H | CH₃ | H | CH₃ | Cl | Cl | S | 2 |
| 5.347 | CH₃ | CH₃ | H | H | H | CH₃ | H | CH₃ | Cl | Cl | S | 0 |
| 5.348 | CH₃ | CH₃ | H | H | H | CH₃ | H | CH₃ | Cl | Cl | S | 2 |
| 5.349 | H | H | H | CH₃ | H | CH₃ | H | CH₃ | Cl | Cl | S | 0 |
| 5.350 | H | H | H | CH₃ | H | CH₃ | H | CH₃ | Cl | Cl | S | 2 |
| 5.351 | H | H | CH₃ | CH₃ | H | CH₃ | H | CH₃ | Cl | Cl | S | 0 |
| 5.352 | H | H | CH₃ | CH₃ | H | CH₃ | H | CH₃ | Cl | Cl | S | 2 |
| 5.353 | H | H | H | H | H | CH₃ | H | CH₃ | CH₃ | CH₃ | S | 0 |
| 5.354 | H | H | H | H | H | CH₃ | H | CH₃ | CH₃ | CH₃ | S | 2 |
| 5.355 | CH₃ | CH₃ | H | H | H | CH₃ | H | CH₃ | CH₃ | CH₃ | S | 0 |
| 5.356 | CH₃ | CH₃ | H | H | H | CH₃ | H | CH₃ | CH₃ | CH₃ | S | 2 |
| 5.357 | H | H | H | CH₃ | H | CH₃ | H | CH₃ | CH₃ | CH₃ | S | 0 |
| 5.358 | H | H | H | CH₃ | H | CH₃ | H | CH₃ | CH₃ | CH₃ | S | 2 |
| 5.359 | H | H | CH₃ | CH₃ | H | CH₃ | H | CH₃ | CH₃ | CH₃ | S | 0 |
| 5.360 | H | H | CH₃ | CH₃ | H | CH₃ | H | CH₃ | CH₃ | CH₃ | S | 2 |
| 5.361 | H | H | H | H | H | CH₃ | H | CH₃ | OCH₃ | H | S | 0 |
| 5.362 | H | H | H | H | H | CH₃ | H | CH₃ | OCH₃ | H | S | 2 |
| 5.363 | CH₃ | CH₃ | H | H | H | CH₃ | H | CH₃ | OCH₃ | H | S | 0 |
| 5.364 | CH₃ | CH₃ | H | H | H | CH₃ | H | CH₃ | OCH₃ | H | S | 2 |
| 5.365 | H | H | H | CH₃ | H | CH₃ | H | CH₃ | OCH₃ | H | S | 0 |
| 5.366 | H | H | H | CH₃ | H | CH₃ | H | CH₃ | OCH₃ | H | S | 2 |
| 5.367 | H | H | CH₃ | CH₃ | H | CH₃ | H | CH₃ | OCH₃ | H | S | 0 |
| 5.368 | H | H | CH₃ | CH₃ | H | CH₃ | H | CH₃ | OCH₃ | H | S | 2 |
| 5.369 | H | H | H | H | H | CH₃ | H | CH₃ | H | H | SO₂ | 0 |
| 5.370 | H | H | H | H | H | CH₃ | H | CH₃ | H | H | SO₂ | 2 |
| 5.371 | CH₃ | CH₃ | H | H | H | CH₃ | H | CH₃ | H | H | SO₂ | 0 |
| 5.372 | CH₃ | CH₃ | H | H | H | CH₃ | H | CH₃ | H | H | SO₂ | 2 |
| 5.373 | H | H | H | CH₃ | H | CH₃ | H | CH₃ | H | H | SO₂ | 0 |
| 5.374 | H | H | H | CH₃ | H | CH₃ | H | CH₃ | H | H | SO₂ | 2 |
| 5.375 | H | H | CH₃ | CH₃ | H | CH₃ | H | CH₃ | H | H | SO₂ | 0 |
| 5.376 | H | H | CH₃ | CH₃ | H | CH₃ | H | CH₃ | H | H | SO₂ | 2 |
| 5.377 | H | H | H | H | H | CH₃ | H | CH₃ | CH₃ | H | SO₂ | 0 |
| 5.378 | H | H | H | H | H | CH₃ | H | CH₃ | CH₃ | H | SO₂ | 2 |
| 5.379 | CH₃ | CH₃ | H | H | H | CH₃ | H | CH₃ | CH₃ | H | SO₂ | 0 |
| 5.380 | CH₃ | CH₃ | H | H | H | CH₃ | H | CH₃ | CH₃ | H | SO₂ | 2 |
| 5.381 | H | H | H | CH₃ | H | CH₃ | H | CH₃ | CH₃ | H | SO₂ | 0 |
| 5.382 | H | H | H | CH₃ | H | CH₃ | H | CH₃ | CH₃ | H | SO₂ | 2 |
| 5.383 | H | H | CH₃ | CH₃ | H | CH₃ | H | CH₃ | CH₃ | H | SO₂ | 0 |
| 5.384 | H | H | CH₃ | CH₃ | H | CH₃ | H | CH₃ | CH₃ | H | SO₂ | 2 |
| 5.385 | H | H | H | H | H | CH₃ | H | CH₃ | Cl | H | SO₂ | 0 |
| 5.386 | H | H | H | H | H | CH₃ | H | CH₃ | Cl | H | SO₂ | 2 |
| 5.387 | CH₃ | CH₃ | H | H | H | CH₃ | H | CH₃ | Cl | H | SO₂ | 0 |
| 5.388 | CH₃ | CH₃ | H | H | H | CH₃ | H | CH₃ | Cl | H | SO₂ | 2 |
| 5.389 | H | H | H | CH₃ | H | CH₃ | H | CH₃ | Cl | H | SO₂ | 0 |
| 5.390 | H | H | H | CH₃ | H | CH₃ | H | CH₃ | Cl | H | SO₂ | 2 |
| 5.391 | H | H | CH₃ | CH₃ | H | CH₃ | H | CH₃ | Cl | H | SO₂ | 0 |
| 5.392 | H | H | CH₃ | CH₃ | H | CH₃ | H | CH₃ | Cl | H | SO₂ | 2 |
| 5.393 | H | H | H | H | H | CH₃ | H | CH₃ | Cl | Cl | SO₂ | 0 |
| 5.394 | H | H | H | H | H | CH₃ | H | CH₃ | Cl | Cl | SO₂ | 2 |
| 5.395 | CH₃ | CH₃ | H | H | H | CH₃ | H | CH₃ | Cl | Cl | SO₂ | 0 |
| 5.396 | CH₃ | CH₃ | H | H | H | CH₃ | H | CH₃ | Cl | Cl | SO₂ | 2 |

TABLE 5-continued

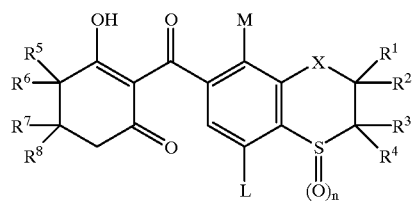

| No. | R5 | R6 | R7 | R8 | R1 | R2 | R3 | R4 | M | L | X | n |
|---|---|---|---|---|---|---|---|---|---|---|---|---|
| 5.397 | H | H | H | CH3 | H | CH3 | H | CH3 | Cl | Cl | SO2 | 0 |
| 5.398 | H | H | H | CH3 | H | CH3 | H | CH3 | Cl | Cl | SO2 | 2 |
| 5.399 | H | H | CH3 | CH3 | H | CH3 | H | CH3 | Cl | Cl | SO2 | 0 |
| 5.400 | H | H | CH3 | CH3 | H | CH3 | H | CH3 | Cl | Cl | SO2 | 2 |
| 5.401 | H | H | H | H | H | CH3 | H | CH3 | CH3 | CH3 | SO2 | 0 |
| 5.402 | H | H | H | H | H | CH3 | H | CH3 | CH3 | CH3 | SO2 | 2 |
| 5.403 | CH3 | CH3 | H | H | H | CH3 | H | CH3 | CH3 | CH3 | SO2 | 0 |
| 5.404 | CH3 | CH3 | H | H | H | CH3 | H | CH3 | CH3 | CH3 | SO2 | 2 |
| 5.405 | H | H | H | CH3 | H | CH3 | H | CH3 | CH3 | CH3 | SO2 | 0 |
| 5.406 | H | H | H | CH3 | H | CH3 | H | CH3 | CH3 | CH3 | SO2 | 2 |
| 5.407 | H | H | CH3 | CH3 | H | CH3 | H | CH3 | CH3 | CH3 | SO2 | 0 |
| 5.408 | H | H | CH3 | CH3 | H | CH3 | H | CH3 | CH3 | CH3 | SO2 | 2 |

TABLE 6

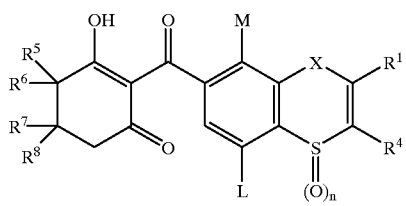

| No. | R5 | R6 | R7 | R8 | R1 | R4 | M | L | X | n |
|---|---|---|---|---|---|---|---|---|---|---|
| 6.1 | H | H | H | H | H | CH3 | H | H | O | 0 |
| 6.2 | H | H | H | H | H | CH3 | H | H | O | 2 |
| 6.3 | CH3 | CH3 | H | H | H | CH3 | H | H | O | 0 |
| 6.4 | CH3 | CH3 | H | H | H | CH3 | H | H | O | 2 |
| 6.5 | H | H | H | CH3 | H | CH3 | H | H | O | 0 |
| 6.6 | H | H | H | CH3 | H | CH3 | H | H | O | 2 |
| 6.7 | H | H | CH3 | CH3 | H | CH3 | H | H | O | 0 |
| 6.8 | H | H | CH3 | CH3 | H | CH3 | H | H | O | 2 |
| 6.9 | H | H | H | H | H | CH3 | CH3 | H | O | 0 |
| 6.10 | H | H | H | H | H | CH3 | CH3 | H | O | 2 |
| 6.11 | CH3 | CH3 | H | H | H | CH3 | CH3 | H | O | 0 |
| 6.12 | CH3 | CH3 | H | H | H | CH3 | CH3 | H | O | 2 |
| 6.13 | H | H | H | CH3 | H | CH3 | CH3 | H | O | 0 |
| 6.14 | H | H | H | CH3 | H | CH3 | CH3 | H | O | 2 |
| 6.15 | H | H | CH3 | CH3 | H | CH3 | CH3 | H | O | 0 |
| 6.16 | H | H | CH3 | CH3 | H | CH3 | CH3 | H | O | 2 |
| 6.17 | H | H | H | H | H | CH3 | Cl | H | O | 0 |
| 6.18 | H | H | H | H | H | CH3 | Cl | H | O | 2 |
| 6.19 | CH3 | CH3 | H | H | H | CH3 | Cl | H | O | 0 |
| 6.20 | CH3 | CH3 | H | H | H | CH3 | Cl | H | O | 2 |
| 6.21 | H | H | H | CH3 | H | CH3 | Cl | H | O | 0 |
| 6.22 | H | H | H | CH3 | H | CH3 | Cl | H | O | 2 |
| 6.23 | H | H | CH3 | CH3 | H | CH3 | Cl | H | O | 0 |
| 6.24 | H | H | CH3 | CH3 | H | CH3 | Cl | H | O | 2 |
| 6.25 | H | H | H | H | H | CH3 | Cl | Cl | O | 0 |
| 6.26 | H | H | H | H | H | CH3 | Cl | Cl | O | 2 |
| 6.27 | CH3 | CH3 | H | H | H | CH3 | Cl | Cl | O | 0 |
| 6.28 | CH3 | CH3 | H | H | H | CH3 | Cl | Cl | O | 2 |
| 6.29 | H | H | H | CH3 | H | CH3 | Cl | Cl | O | 0 |
| 6.30 | H | H | H | CH3 | H | CH3 | Cl | Cl | O | 2 |
| 6.31 | H | H | CH3 | CH3 | H | CH3 | Cl | Cl | O | 0 |
| 6.32 | H | H | CH3 | CH3 | H | CH3 | Cl | Cl | O | 2 |
| 6.33 | H | H | H | H | H | CH3 | CH3 | CH3 | O | 0 |
| 6.34 | H | H | H | H | H | CH3 | CH3 | CH3 | O | 2 |
| 6.35 | CH3 | CH3 | H | H | H | CH3 | CH3 | CH3 | O | 0 |
| 6.36 | CH3 | CH3 | H | H | H | CH3 | CH3 | CH3 | O | 2 |

TABLE 6-continued

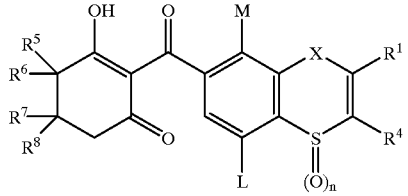

| No. | R⁵ | R⁶ | R⁷ | R⁸ | R¹ | R⁴ | M | L | X | n |
|---|---|---|---|---|---|---|---|---|---|---|
| 6.37 | H | H | H | CH₃ | H | CH₃ | CH₃ | CH₃ | O | 0 |
| 6.38 | H | H | H | CH₃ | H | CH₃ | CH₃ | CH₃ | O | 2 |
| 6.39 | H | H | CH₃ | CH₃ | H | CH₃ | CH₃ | CH₃ | O | 0 |
| 6.40 | H | H | CH₃ | CH₃ | H | CH₃ | CH₃ | CH₃ | O | 2 |
| 6.41 | H | H | H | H | H | CH₃ | H | H | S | 0 |
| 6.42 | H | H | H | H | H | CH₃ | H | H | S | 2 |
| 6.43 | CH₃ | CH₃ | H | H | H | CH₃ | H | H | S | 0 |
| 6.44 | CH₃ | CH₃ | H | H | H | CH₃ | H | H | S | 2 |
| 6.45 | H | H | H | CH₃ | H | CH₃ | H | H | S | 0 |
| 6.46 | H | H | H | CH₃ | H | CH₃ | H | H | S | 2 |
| 6.47 | H | H | CH₃ | CH₃ | H | CH₃ | H | H | S | 0 |
| 6.48 | H | H | CH₃ | CH₃ | H | CH₃ | H | H | S | 2 |
| 6.49 | H | H | H | H | H | CH₃ | CH₃ | H | S | 0 |
| 6.50 | H | H | H | H | H | CH₃ | CH₃ | H | S | 2 |
| 6.51 | CH₃ | CH₃ | H | H | H | CH₃ | CH₃ | H | S | 0 |
| 6.52 | CH₃ | CH₃ | H | H | H | CH₃ | CH₃ | H | S | 2 |
| 6.53 | H | H | H | CH₃ | H | CH₃ | CH₃ | H | S | 0 |
| 6.54 | H | H | H | CH₃ | H | CH₃ | CH₃ | H | S | 2 |
| 6.55 | H | H | CH₃ | CH₃ | H | CH₃ | CH₃ | H | S | 0 |
| 6.56 | H | H | CH₃ | CH₃ | H | CH₃ | CH₃ | H | S | 2 |
| 6.57 | H | H | H | H | H | CH₃ | Cl | H | S | 0 |
| 6.58 | H | H | H | H | H | CH₃ | Cl | H | S | 2 |
| 6.59 | CH₃ | CH₃ | H | H | H | CH₃ | Cl | H | S | 0 |
| 6.60 | CH₃ | CH₃ | H | H | H | CH₃ | Cl | H | S | 2 |
| 6.61 | H | H | H | CH₃ | H | CH₃ | Cl | H | S | 0 |
| 6.62 | H | H | H | CH₃ | H | CH₃ | Cl | H | S | 2 |
| 6.63 | H | H | CH₃ | CH₃ | H | CH₃ | Cl | H | S | 0 |
| 6.64 | H | H | CH₃ | CH₃ | H | CH₃ | Cl | H | S | 2 |
| 6.65 | H | H | H | H | H | CH₃ | Cl | Cl | S | 0 |
| 6.66 | H | H | H | H | H | CH₃ | Cl | Cl | S | 2 |
| 6.67 | CH₃ | CH₃ | H | H | H | CH₃ | Cl | Cl | S | 0 |
| 6.68 | CH₃ | CH₃ | H | H | H | CH₃ | Cl | Cl | S | 2 |
| 6.69 | H | H | H | CH₃ | H | CH₃ | Cl | Cl | S | 0 |
| 6.70 | H | H | H | CH₃ | H | CH₃ | Cl | Cl | S | 2 |
| 6.71 | H | H | CH₃ | CH₃ | H | CH₃ | Cl | Cl | S | 0 |
| 6.72 | H | H | CH₃ | CH₃ | H | CH₃ | Cl | Cl | S | 2 |
| 6.73 | H | H | H | H | H | CH₃ | CH₃ | CH₃ | S | 0 |
| 6.74 | H | H | H | H | H | CH₃ | CH₃ | CH₃ | S | 2 |
| 6.75 | CH₃ | CH₃ | H | H | H | CH₃ | CH₃ | CH₃ | S | 0 |
| 6.76 | CH₃ | CH₃ | H | H | H | CH₃ | CH₃ | CH₃ | S | 2 |
| 6.77 | H | H | H | CH₃ | H | CH₃ | CH₃ | CH₃ | S | 0 |
| 6.78 | H | H | H | CH₃ | H | CH₃ | CH₃ | CH₃ | S | 2 |
| 6.79 | H | H | CH₃ | CH₃ | H | CH₃ | CH₃ | CH₃ | S | 0 |
| 6.80 | H | H | CH₃ | CH₃ | H | CH₃ | CH₃ | CH₃ | S | 2 |
| 6.81 | H | H | H | H | H | CH₃ | H | H | SO₂ | 0 |
| 6.82 | H | H | H | H | H | CH₃ | H | H | SO₂ | 2 |
| 6.83 | CH₃ | CH₃ | H | H | H | CH₃ | H | H | SO₂ | 0 |
| 6.84 | CH₃ | CH₃ | H | H | H | CH₃ | H | H | SO₂ | 2 |
| 6.85 | H | H | H | CH₃ | H | CH₃ | H | H | SO₂ | 0 |
| 6.86 | H | H | H | CH₃ | H | CH₃ | H | H | SO₂ | 2 |
| 6.87 | H | H | CH₃ | CH₃ | H | CH₃ | H | H | SO₂ | 0 |
| 6.88 | H | H | CH₃ | CH₃ | H | CH₃ | H | H | SO₂ | 2 |
| 6.89 | H | H | H | H | H | CH₃ | CH₃ | H | SO₂ | 0 |
| 6.90 | H | H | H | H | H | CH₃ | CH₃ | H | SO₂ | 2 |
| 6.91 | CH₃ | CH₃ | H | H | H | CH₃ | CH₃ | H | SO₂ | 0 |
| 6.92 | CH₃ | CH₃ | H | H | H | CH₃ | CH₃ | H | SO₂ | 2 |
| 6.93 | H | H | H | CH₃ | H | CH₃ | CH₃ | H | SO₂ | 0 |
| 6.94 | H | H | H | CH₃ | H | CH₃ | CH₃ | H | SO₂ | 2 |
| 6.95 | H | H | CH₃ | CH₃ | H | CH₃ | CH₃ | H | SO₂ | 0 |
| 6.96 | H | H | CH₃ | CH₃ | H | CH₃ | CH₃ | H | SO₂ | 2 |
| 6.97 | H | H | H | H | H | CH₃ | Cl | H | SO₂ | 0 |
| 6.98 | H | H | H | H | H | CH₃ | Cl | H | SO₂ | 2 |
| 6.99 | CH₃ | CH₃ | H | H | H | CH₃ | Cl | H | SO₂ | 0 |
| 6.100 | CH₃ | CH₃ | H | H | H | CH₃ | Cl | H | SO₂ | 2 |
| 6.101 | H | H | H | CH₃ | H | CH₃ | Cl | H | SO₂ | 0 |
| 6.102 | H | H | H | CH₃ | H | CH₃ | Cl | H | SO₂ | 2 |

TABLE 6-continued

[Structure: cyclohexanedione-OH with carbonyl linked to benzene ring bearing M, L substituents and fused thiazine/oxazine ring with X, R¹, R⁴, S(O)ₙ]

| No. | $R^5$ | $R^6$ | $R^7$ | $R^8$ | $R^1$ | $R^4$ | M | L | X | n |
|---|---|---|---|---|---|---|---|---|---|---|
| 6.103 | H | H | $CH_3$ | $CH_3$ | H | $CH_3$ | Cl | H | $SO_2$ | 0 |
| 6.104 | H | H | $CH_3$ | $CH_3$ | H | $CH_3$ | Cl | H | $SO_2$ | 2 |
| 6.105 | H | H | H | H | H | $CH_3$ | Cl | Cl | $SO_2$ | 0 |
| 6.106 | H | H | H | H | H | $CH_3$ | Cl | Cl | $SO_2$ | 2 |
| 6.107 | $CH_3$ | $CH_3$ | H | H | H | $CH_3$ | Cl | Cl | $SO_2$ | 0 |
| 6.108 | $CH_3$ | $CH_3$ | H | H | H | $CH_3$ | Cl | Cl | $SO_2$ | 2 |
| 6.109 | H | H | H | $CH_3$ | H | $CH_3$ | Cl | Cl | $SO_2$ | 0 |
| 6.110 | H | H | H | $CH_3$ | H | $CH_3$ | Cl | Cl | $SO_2$ | 2 |
| 6.111 | H | H | $CH_3$ | $CH_3$ | H | $CH_3$ | Cl | Cl | $SO_2$ | pard 0 |
| 6.112 | H | H | $CH_3$ | $CH_3$ | H | $CH_3$ | Cl | Cl | $SO_2$ | 2 |
| 6.113 | H | H | H | H | H | $CH_3$ | $CH_3$ | $CH_3$ | $SO_2$ | 0 |
| 6.114 | H | H | H | H | H | $CH_3$ | $CH_3$ | $CH_3$ | $SO_2$ | 2 |
| 6.115 | $CH_3$ | $CH_3$ | H | H | H | $CH_3$ | $CH_3$ | $CH_3$ | $SO_2$ | 0 |
| 6.116 | $CH_3$ | $CH_3$ | H | H | H | $CH_3$ | $CH_3$ | $CH_3$ | $SO_2$ | 2 |
| 6.117 | H | H | H | $CH_3$ | H | $CH_3$ | $CH_3$ | $CH_3$ | $SO_2$ | 0 |
| 6.118 | H | H | H | $CH_3$ | H | $CH_3$ | $CCH_3$ | $CH_3$ | $SO_2$ | 2 |
| 6.119 | H | H | $CH_3$ | $CH_3$ | H | $CH_3$ | $CH_3$ | $CH_3$ | $SO_2$ | 0 |
| 6.120 | H | H | $CH_3$ | $CH_3$ | H | $CH_3$ | $CH_3$ | $CH_3$ | $SO_2$ | 2 |
| 6.121 | H | H | H | H | $CH_3$ | H | H | H | O | 0 |
| 6.122 | H | H | H | H | $CH_3$ | H | H | H | O | 2 |
| 6.123 | $CH_3$ | $CH_3$ | H | H | $CH_3$ | H | H | H | O | 0 |
| 6.124 | $CH_3$ | $CH_3$ | H | H | $CH_3$ | H | H | H | O | 2 |
| 6.125 | H | H | H | $CH_3$ | $CH_3$ | H | H | H | O | 0 |
| 6.126 | H | H | H | $CH_3$ | $CH_3$ | H | H | H | O | 2 |
| 6.127 | H | H | $CH_3$ | $CH_3$ | $CH_3$ | H | H | H | O | 0 |
| 6.128 | H | H | $CH_3$ | $CH_3$ | $CH_3$ | H | H | H | O | 2 |
| 6.129 | H | H | H | H | $CH_3$ | H | $CH_3$ | H | O | 0 |
| 6.130 | H | H | H | H | $CH_3$ | H | $CH_3$ | H | O | 2 |
| 6.131 | $CH_3$ | $CH_3$ | H | H | $CH_3$ | H | $CH_3$ | H | O | 0 |
| 6.132 | $CH_3$ | $CH_3$ | H | H | $CH_3$ | H | $CH_3$ | H | O | 2 |
| 6.133 | H | H | H | $CH_3$ | $CH_3$ | H | $CH_3$ | H | O | 0 |
| 6.134 | H | H | H | $CH_3$ | $CH_3$ | H | $CH_3$ | H | O | 2 |
| 6.135 | H | H | $CH_3$ | $CH_3$ | $CH_3$ | H | $CH_3$ | H | O | 0 |
| 6.136 | H | H | $CH_3$ | $CH_3$ | $CH_3$ | H | $CH_3$ | H | O | 2 |
| 6.137 | H | H | H | H | $CH_3$ | H | Cl | H | O | 0 |
| 6.138 | H | H | H | H | $CH_3$ | H | Cl | H | O | 2 |
| 6.139 | $CH_3$ | $CH_3$ | H | H | $CH_3$ | H | Cl | H | O | 0 |
| 6.140 | $CH_3$ | $CH_3$ | H | H | $CH_3$ | H | Cl | H | O | 2 |
| 6.141 | H | H | H | $CH_3$ | $CH_3$ | H | Cl | H | O | 0 |
| 6.142 | H | H | H | $CH_3$ | $CH_3$ | H | Cl | H | O | 2 |
| 6.143 | H | H | $CH_3$ | $CH_3$ | $CH_3$ | H | Cl | H | O | 0 |
| 6.144 | H | H | $CH_3$ | $CH_3$ | $CH_3$ | H | Cl | H | O | 2 |
| 6.145 | H | H | H | H | $CH_3$ | H | Cl | Cl | O | 0 |
| 6.146 | H | H | H | H | $CH_3$ | H | Cl | Cl | O | 2 |
| 6.147 | $CH_3$ | $CH_3$ | H | H | $CH_3$ | H | Cl | Cl | O | 0 |
| 6.148 | $CH_3$ | $CH_3$ | H | H | $CH_3$ | H | Cl | Cl | O | 2 |
| 6.149 | H | H | H | $CH_3$ | $CH_3$ | H | Cl | Cl | O | 0 |
| 6.150 | H | H | H | $CH_3$ | $CH_3$ | H | Cl | Cl | O | 2 |
| 6.151 | H | H | $CH_3$ | $CH_3$ | $CH_3$ | H | Cl | Cl | O | 0 |
| 6.152 | H | H | $CH_3$ | $CH_3$ | $CH_3$ | H | Cl | Cl | O | 2 |
| 6.153 | H | H | H | H | $CH_3$ | H | $CH_3$ | $CH_3$ | O | 0 |
| 6.154 | H | H | H | H | $CH_3$ | H | $CH_3$ | $CH_3$ | O | 2 |
| 6.155 | $CH_3$ | $CH_3$ | H | H | $CH_3$ | H | $CH_3$ | $CH_3$ | O | 0 |
| 6.156 | $CH_3$ | $CH_3$ | H | H | $CH_3$ | H | $CH_3$ | $CH_3$ | O | 2 |
| 6.157 | H | H | H | $CH_3$ | $CH_3$ | H | $CH_3$ | $CH_3$ | O | 0 |
| 6.158 | H | H | H | $CH_3$ | $CH_3$ | H | $CH_3$ | $CH_3$ | O | 2 |
| 6.159 | H | H | $CH_3$ | $CH_3$ | $CH_3$ | H | $CH_3$ | $CH_3$ | O | 0 |
| 6.160 | H | H | $CH_3$ | $CH_3$ | $CH_3$ | H | $CH_3$ | $CH_3$ | O | 2 |
| 6.161 | H | H | H | H | $CH_3$ | H | H | H | S | 0 |
| 6.162 | H | H | H | H | $CH_3$ | H | H | H | S | 2 |
| 6.163 | $CH_3$ | $CH_3$ | H | H | $CH_3$ | H | H | H | S | 0 |
| 6.164 | $CH_3$ | $CH_3$ | H | H | $CH_3$ | H | H | H | S | 2 |
| 6.165 | H | H | H | $CH_3$ | $CH_3$ | H | H | H | S | 0 |
| 6.166 | H | H | H | $CH_3$ | $CH_3$ | H | H | H | S | 2 |
| 6.167 | H | H | $CH_3$ | $CH_3$ | $CH_3$ | H | H | H | S | 0 |
| 6.168 | H | H | $CH_3$ | $CH_3$ | $CH_3$ | H | H | H | S | 2 |

TABLE 6-continued

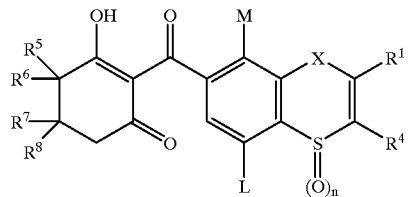

| No. | R⁵ | R⁶ | R⁷ | R⁸ | R¹ | R⁴ | M | L | X | n |
|---|---|---|---|---|---|---|---|---|---|---|
| 6.169 | H | H | H | H | CH₃ | H | CH₃ | H | S | 0 |
| 6.170 | H | H | H | H | CH₃ | H | CH₃ | H | S | 2 |
| 6.171 | CH₃ | CH₃ | H | H | CH₃ | H | CH₃ | H | S | 0 |
| 6.172 | CH₃ | CH₃ | H | H | CH₃ | H | CH₃ | H | S | 2 |
| 6.173 | H | H | H | CH₃ | CH₃ | H | CH₃ | H | S | 0 |
| 6.174 | H | H | H | CH₃ | CH₃ | H | CH₃ | H | S | 2 |
| 6.175 | H | H | CH₃ | CH₃ | CH₃ | H | CH₃ | H | S | 0 |
| 6.176 | H | H | CH₃ | CH₃ | CH₃ | H | CH₃ | H | S | 2 |
| 6.177 | H | H | H | H | CH₃ | H | Cl | H | S | 0 |
| 6.178 | H | H | H | H | CH₃ | H | Cl | H | S | 2 |
| 6.179 | CH₃ | CH₃ | H | H | CH₃ | H | Cl | H | S | 0 |
| 6.180 | CH₃ | CH₃ | H | H | CH₃ | H | Cl | H | S | 2 |
| 6.181 | H | H | H | CH₃ | CH₃ | H | Cl | H | S | 0 |
| 6.182 | H | H | H | CH₃ | CH₃ | H | Cl | H | S | 2 |
| 6.183 | H | H | CH₃ | CH₃ | CH₃ | H | Cl | H | S | 0 |
| 6.184 | H | H | CH₃ | CH₃ | CH₃ | H | Cl | H | S | 2 |
| 6.185 | H | H | H | H | CH₃ | H | Cl | Cl | S | 0 |
| 6.186 | H | H | H | H | CH₃ | H | Cl | Cl | S | 2 |
| 6.187 | CH₃ | CH₃ | H | H | CH₃ | H | Cl | Cl | S | 0 |
| 6.188 | CH₃ | CH₃ | H | H | CH₃ | H | Cl | Cl | S | 2 |
| 6.189 | H | H | H | CH₃ | CH₃ | H | Cl | Cl | S | 0 |
| 6.190 | H | H | H | CH₃ | CH₃ | H | Cl | Cl | S | 2 |
| 6.191 | H | H | CH₃ | CH₃ | CH₃ | H | Cl | Cl | S | 0 |
| 6.192 | H | H | CH₃ | CH₃ | CH₃ | H | Cl | Cl | S | 2 |
| 6.193 | H | H | H | H | CH₃ | H | CH₃ | CH₃ | S | 0 |
| 6.194 | H | H | H | H | CH₃ | H | CH₃ | CH₃ | S | 2 |
| 6.195 | CH₃ | CH₃ | H | H | CH₃ | H | CH₃ | CH₃ | S | 0 |
| 6.196 | CH₃ | CH₃ | H | H | CH₃ | H | CH₃ | CH₃ | S | 2 |
| 6.197 | H | H | H | CH₃ | CH₃ | H | CH₃ | CH₃ | S | 0 |
| 6.198 | H | H | H | CH₃ | CH₃ | H | CH₃ | CH₃ | S | 2 |
| 6.199 | H | H | CH₃ | CH₃ | CH₃ | H | CH₃ | CH₃ | S | 0 |
| 6.200 | H | H | CH₃ | CH₃ | CH₃ | H | CH₃ | CH₃ | S | 2 |
| 6.201 | H | H | H | H | CH₃ | H | H | H | SO₂ | 0 |
| 6.202 | H | H | H | H | CH₃ | H | H | H | SO₂ | 2 |
| 6.203 | CH₃ | CH₃ | H | H | CH₃ | H | H | H | SO₂ | 0 |
| 6.204 | CH₃ | CH₃ | H | H | CH₃ | H | H | H | SO₂ | 2 |
| 6.205 | H | H | H | CH₃ | CH₃ | H | H | H | SO₂ | 0 |
| 6.206 | H | H | H | CH₃ | CH₃ | H | H | H | SO₂ | 2 |
| 6.207 | H | H | CH₃ | CH₃ | CH₃ | H | H | H | SO₂ | 0 |
| 6.208 | H | H | CH₃ | CH₃ | CH₃ | H | H | H | SO₂ | 2 |
| 6.209 | H | H | H | H | CH₃ | H | CH₃ | H | SO₂ | 0 |
| 6.210 | H | H | H | H | CH₃ | H | CH₃ | H | SO₂ | 2 |
| 6.211 | CH₃ | CH₃ | H | H | CH₃ | H | CH₃ | H | SO₂ | 0 |
| 6.212 | CH₃ | CH₃ | H | H | CH₃ | H | CH₃ | H | SO₂ | 2 |
| 6.213 | H | H | H | CH₃ | CH₃ | H | CH₃ | H | SO₂ | 0 |
| 6.214 | H | H | H | CH₃ | CH₃ | H | CH₃ | H | SO₂ | 2 |
| 6.215 | H | H | CH₃ | CH₃ | CH₃ | H | CH₃ | H | SO₂ | 0 |
| 6.216 | H | H | CH₃ | CH₃ | CH₃ | H | CH₃ | H | SO₂ | 2 |
| 6.217 | H | H | H | H | CH₃ | H | Cl | H | SO₂ | 0 |
| 6.218 | H | H | H | H | CH₃ | H | Cl | H | SO₂ | 2 |
| 6.219 | CH₃ | CH₃ | H | H | CH₃ | H | Cl | H | SO₂ | 0 |
| 6.220 | CH₃ | CH₃ | H | H | CH₃ | H | Cl | H | SO₂ | 2 |
| 6.221 | H | H | H | CH₃ | CH₃ | H | Cl | H | SO₂ | 0 |
| 6.222 | H | H | H | CH₃ | CH₃ | H | Cl | H | SO₂ | 2 |
| 6.223 | H | H | CH₃ | CH₃ | CH₃ | H | Cl | H | SO₂ | 0 |
| 6.224 | H | H | CH₃ | CH₃ | CH₃ | H | Cl | H | SO₂ | 2 |
| 6.225 | H | H | H | H | CH₃ | H | Cl | Cl | SO₂ | 0 |
| 6.226 | H | H | H | H | CH₃ | H | Cl | Cl | SO₂ | 2 |
| 6.227 | CH₃ | CH₃ | H | H | CH₃ | H | Cl | Cl | SO₂ | 0 |
| 6.228 | CH₃ | CH₃ | H | H | CH₃ | H | Cl | Cl | SO₂ | 2 |
| 6.229 | H | H | H | CH₃ | CH₃ | H | Cl | Cl | SO₂ | 0 |
| 6.230 | H | H | H | CH₃ | CH₃ | H | Cl | Cl | SO₂ | 2 |
| 6.231 | H | H | CH₃ | CH₃ | CH₃ | H | Cl | Cl | SO₂ | 0 |
| 6.232 | H | H | CH₃ | CH₃ | CH₃ | H | Cl | Cl | SO₂ | 2 |
| 6.233 | H | H | H | H | CH₃ | H | CH₃ | CH₃ | SO₂ | 0 |
| 6.234 | H | H | H | H | CH₃ | H | CH₃ | CH₃ | SO₂ | 2 |

TABLE 6-continued

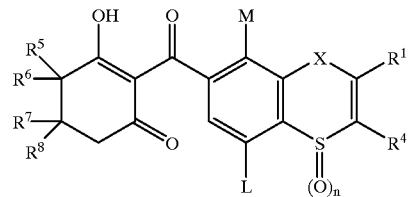

| No. | R⁵ | R⁶ | R⁷ | R⁸ | R¹ | R⁴ | M | L | X | n |
|---|---|---|---|---|---|---|---|---|---|---|
| 6.235 | CH₃ | CH₃ | H | H | CH₃ | H | CH₃ | CH₃ | SO₂ | 0 |
| 6.236 | CH₃ | CH₃ | H | H | CH₃ | H | CH₃ | CH₃ | SO₂ | 2 |
| 6.237 | H | H | H | CH₃ | CH₃ | H | CH₃ | CH₃ | SO₂ | 0 |
| 6.238 | H | H | H | CH₃ | CH₃ | H | CH₃ | CH₃ | SO₂ | 2 |
| 6.239 | H | H | CH₃ | CH₃ | CH₃ | H | CH₃ | CH₃ | SO₂ | 0 |
| 6.240 | H | H | CH₃ | CH₃ | CH₃ | H | CH₃ | CH₃ | SO₂ | 2 |
| 6.241 | H | H | H | H | CH₃ | CH₃ | H | H | O | 0 |
| 6.242 | H | H | H | H | CH₃ | CH₃ | H | H | O | 2 |
| 6.243 | CH₃ | CH₃ | H | H | CH₃ | CH₃ | H | H | O | 0 |
| 6.244 | CH₃ | CH₃ | H | H | CH₃ | CH₃ | H | H | O | 2 |
| 6.245 | H | H | H | CH₃ | CH₃ | CH₃ | H | H | O | 0 |
| 6.246 | H | H | H | CH₃ | CH₃ | CH₃ | H | H | O | 2 |
| 6.247 | H | H | CH₃ | CH₃ | CH₃ | CH₃ | H | H | O | 0 |
| 6.248 | H | H | CH₃ | CH₃ | CH₃ | CH₃ | H | H | O | 2 |
| 6.249 | H | H | H | H | CH₃ | CH₃ | CH₃ | H | O | 0 |
| 6.250 | H | H | H | H | CH₃ | CH₃ | CH₃ | H | O | 2 |
| 6.251 | CH₃ | CH₃ | H | H | CH₃ | CH₃ | CH₃ | H | O | 0 |
| 6.252 | CH₃ | CH₃ | H | H | CH₃ | CH₃ | CH₃ | H | O | 2 |
| 6.253 | H | H | H | CH₃ | CH₃ | CH₃ | CH₃ | H | O | 0 |
| 6.254 | H | H | H | CH₃ | CH₃ | CH₃ | CH₃ | H | O | 2 |
| 6.255 | H | H | CH₃ | CH₃ | CH₃ | CH₃ | CH₃ | H | O | 0 |
| 6.256 | H | H | CH₃ | CH₃ | CH₃ | CH₃ | CH₃ | H | O | 2 |
| 6.257 | H | H | H | H | CH₃ | CH₃ | Cl | H | O | 0 |
| 6.258 | H | H | H | H | CH₃ | CH₃ | Cl | H | O | 2 |
| 6.259 | CH₃ | CH₃ | H | H | CH₃ | CH₃ | Cl | H | O | 0 |
| 6.260 | CH₃ | CH₃ | H | H | CH₃ | CH₃ | Cl | H | O | 2 |
| 6.261 | H | H | H | CH₃ | CH₃ | CH₃ | Cl | H | O | 0 |
| 6.262 | H | H | H | CH₃ | CH₃ | CH₃ | Cl | H | O | 2 |
| 6.263 | H | H | CH₃ | CH₃ | CH₃ | CH₃ | Cl | H | O | 0 |
| 6.264 | H | H | CH₃ | CH₃ | CH₃ | CH₃ | Cl | H | O | 2 |
| 6.265 | H | H | H | H | CH₃ | CH₃ | Cl | Cl | O | 0 |
| 6.266 | H | H | H | H | CH₃ | CH₃ | Cl | Cl | O | 2 |
| 6.267 | CH₃ | CH₃ | H | H | CH₃ | CH₃ | Cl | Cl | O | 0 |
| 6.268 | CH₃ | CH₃ | H | H | CH₃ | CH₃ | Cl | Cl | O | 2 |
| 6.269 | H | H | H | CH₃ | CH₃ | CH₃ | Cl | Cl | O | 0 |
| 6.270 | H | H | H | CH₃ | CH₃ | CH₃ | Cl | Cl | O | 2 |
| 6.271 | H | H | CH₃ | CH₃ | CH₃ | CH₃ | Cl | Cl | O | 0 |
| 6.272 | H | H | CH₃ | CH₃ | CH₃ | CH₃ | Cl | Cl | O | 2 |
| 6.273 | H | H | H | H | CH₃ | CH₃ | CH₃ | CH₃ | O | 0 |
| 6.274 | H | H | H | H | CH₃ | CH₃ | CH₃ | CH₃ | O | 2 |
| 6.275 | CH₃ | CH₃ | H | H | CH₃ | CH₃ | CH₃ | CH₃ | O | 0 |
| 6.276 | CH₃ | CH₃ | H | H | CH₃ | CH₃ | CH₃ | CH₃ | O | 2 |
| 6.277 | H | H | H | CH₃ | CH₃ | CH₃ | CH₃ | CH₃ | O | 0 |
| 6.278 | H | H | H | CH₃ | CH₃ | CH₃ | CH₃ | CH₃ | O | 2 |
| 6.279 | H | H | CH₃ | CH₃ | CH₃ | CH₃ | CH₃ | CH₃ | O | 0 |
| 6.280 | H | H | CH₃ | CH₃ | CH₃ | CH₃ | CH₃ | CH₃ | O | 2 |
| 6.281 | H | H | H | H | CH₃ | CH₃ | H | H | S | 0 |
| 6.282 | H | H | H | H | CH₃ | CH₃ | H | H | S | 2 |
| 6.283 | CH₃ | CH₃ | H | H | CH₃ | CH₃ | H | H | S | 0 |
| 6.284 | CH₃ | CH₃ | H | H | CH₃ | CH₃ | H | H | S | 2 |
| 6.285 | H | H | H | CH₃ | CH₃ | CH₃ | H | H | S | 0 |
| 6.286 | H | H | H | CH₃ | CH₃ | CH₃ | H | H | S | 2 |
| 6.287 | H | H | CH₃ | CH₃ | CH₃ | CH₃ | H | H | S | 0 |
| 6.288 | H | H | CH₃ | CH₃ | CH₃ | CH₃ | H | H | S | 2 |
| 6.289 | H | H | H | H | CH₃ | CH₃ | CH₃ | H | S | 0 |
| 6.290 | H | H | H | H | CH₃ | CH₃ | CH₃ | H | S | 2 |
| 6.291 | CH₃ | CH₃ | H | H | CH₃ | CH₃ | CH₃ | H | S | 0 |
| 6.292 | CH₃ | CH₃ | H | H | CH₃ | CH₃ | CH₃ | H | S | 2 |
| 6.293 | H | H | H | CH₃ | CH₃ | CH₃ | CH₃ | H | S | 0 |
| 6.294 | H | H | H | CH₃ | CH₃ | CH₃ | CH₃ | H | S | 2 |
| 6.295 | H | H | CH₃ | CH₃ | CH₃ | CH₃ | CH₃ | H | S | 0 |
| 6.296 | H | H | CH₃ | CH₃ | CH₃ | CH₃ | CH₃ | H | S | 2 |
| 6.297 | H | H | H | H | CH₃ | CH₃ | Cl | H | S | 0 |
| 6.298 | H | H | H | H | CH₃ | CH₃ | Cl | H | S | 2 |
| 6.299 | CH₃ | CH₃ | H | H | CH₃ | CH₃ | Cl | H | S | 0 |
| 6.300 | CH₃ | CH₃ | H | H | CH₃ | CH₃ | Cl | H | S | 2 |

TABLE 6-continued

| No. | $R^5$ | $R^6$ | $R^7$ | $R^8$ | $R^1$ | $R^4$ | M | L | X | n |
|---|---|---|---|---|---|---|---|---|---|---|
| 6.301 | H | H | H | $CH_3$ | $CH_3$ | $CH_3$ | Cl | H | S | 0 |
| 6.302 | H | H | H | $CH_3$ | $CH_3$ | $CH_3$ | Cl | H | S | 2 |
| 6.303 | H | H | $CH_3$ | $CH_3$ | $CH_3$ | $CH_3$ | Cl | H | S | 0 |
| 6.304 | H | H | $CH_3$ | $CH_3$ | $CH_3$ | $CH_3$ | Cl | H | S | 2 |
| 6.305 | H | H | H | H | $CH_3$ | $CH_3$ | Cl | Cl | S | 0 |
| 6.306 | H | H | H | H | $CH_3$ | $CH_3$ | Cl | Cl | S | 2 |
| 6.307 | $CH_3$ | $CH_3$ | H | H | $CH_3$ | $CH_3$ | Cl | Cl | S | 0 |
| 6.308 | $CH_3$ | $CH_3$ | H | H | $CH_3$ | $CH_3$ | Cl | Cl | S | 2 |
| 6.309 | H | H | H | $CH_3$ | $CH_3$ | $CH_3$ | Cl | Cl | S | 0 |
| 6.310 | H | H | H | $CH_3$ | $CH_3$ | $CH_3$ | Cl | Cl | S | 2 |
| 6.311 | H | H | $CH_3$ | $CH_3$ | $CH_3$ | $CH_3$ | Cl | Cl | S | 0 |
| 6.312 | H | H | $CH_3$ | $CH_3$ | $CH_3$ | $CH_3$ | Cl | Cl | S | 2 |
| 6.313 | H | H | H | H | $CH_3$ | $CH_3$ | $CH_3$ | $CH_3$ | S | 0 |
| 6.314 | H | H | H | H | $CH_3$ | $CH_3$ | $CH_3$ | $CH_3$ | S | 2 |
| 6.315 | $CH_3$ | $CH_3$ | H | H | $CH_3$ | $CH_3$ | $CH_3$ | $CH_3$ | S | 0 |
| 6.316 | $CH_3$ | $CH_3$ | H | H | $CH_3$ | $CH_3$ | $CH_3$ | $CH_3$ | S | 2 |
| 6.317 | H | H | H | $CH_3$ | $CH_3$ | $CH_3$ | $CH_3$ | $CH_3$ | S | 0 |
| 6.318 | H | H | H | $CH_3$ | $CH_3$ | $CH_3$ | $CH_3$ | $CH_3$ | S | 2 |
| 6.319 | H | H | $CH_3$ | $CH_3$ | $CH_3$ | $CH_3$ | $CH_3$ | $CH_3$ | S | 0 |
| 6.320 | H | H | $CH_3$ | $CH_3$ | $CH_3$ | $CH_3$ | $CH_3$ | $CH_3$ | S | 2 |
| 6.321 | H | H | H | H | $CH_3$ | $CH_3$ | H | H | $SO_2$ | 0 |
| 6.322 | H | H | H | H | $CH_3$ | $CH_3$ | H | H | $SO_2$ | 2 |
| 6.323 | $CH_3$ | $CH_3$ | H | H | $CH_3$ | $CH_3$ | H | H | $SO_2$ | 0 |
| 6.324 | $CH_3$ | $CH_3$ | H | H | $CH_3$ | $CH_3$ | H | H | $SO_2$ | 2 |
| 6.325 | H | H | H | $CH_3$ | $CH_3$ | $CH_3$ | H | H | $SO_2$ | 0 |
| 6.326 | H | H | H | $CH_3$ | $CH_3$ | $CH_3$ | H | H | $SO_2$ | 2 |
| 6.327 | H | H | $CH_3$ | $CH_3$ | $CH_3$ | $CH_3$ | H | H | $SO_2$ | 0 |
| 6.328 | H | H | $CH_3$ | $CH_3$ | $CH_3$ | $CH_3$ | H | H | $SO_2$ | 2 |
| 6.329 | H | H | H | H | $CH_3$ | $CH_3$ | $CH_3$ | H | $SO_2$ | 0 |
| 6.330 | H | H | H | H | $CH_3$ | $CH_3$ | $CH_3$ | H | $SO_2$ | 2 |
| 6.331 | $CH_3$ | $CH_3$ | H | H | $CH_3$ | $CH_3$ | $CH_3$ | H | $SO_2$ | 0 |
| 6.332 | $CH_3$ | $CH_3$ | H | H | $CH_3$ | $CH_3$ | $CH_3$ | H | $SO_2$ | 2 |
| 6.333 | H | H | H | $CH_3$ | $CH_3$ | $CH_3$ | $CH_3$ | H | $SO_2$ | 0 |
| 6.334 | H | H | H | $CH_3$ | $CH_3$ | $CH_3$ | $CH_3$ | H | $SO_2$ | 2 |
| 6.335 | H | H | $CH_3$ | $CH_3$ | $CH_3$ | $CH_3$ | $CH_3$ | H | $SO_2$ | 0 |
| 6.336 | H | H | $CH_3$ | $CH_3$ | $CH_3$ | $CH_3$ | $CH_3$ | H | $SO_2$ | 2 |
| 6.337 | H | H | H | H | $CH_3$ | $CH_3$ | Cl | H | $SO_2$ | 0 |
| 6.338 | H | H | H | H | $CH_3$ | $CH_3$ | Cl | H | $SO_2$ | 2 |
| 6.339 | $CH_3$ | $CH_3$ | H | H | $CH_3$ | $CH_3$ | Cl | H | $SO_2$ | 0 |
| 6.340 | $CH_3$ | $CH_3$ | H | H | $CH_3$ | $CH_3$ | Cl | H | $SO_2$ | 2 |
| 6.341 | H | H | H | $CH_3$ | $CH_3$ | $CH_3$ | Cl | H | $SO_2$ | 0 |
| 6.342 | H | H | H | $CH_3$ | $CH_3$ | $CH_3$ | Cl | H | $SO_2$ | 2 |
| 6.343 | H | H | $CH_3$ | $CH_3$ | $CH_3$ | $CH_3$ | Cl | H | $SO_2$ | 0 |
| 6.344 | H | H | $CH_3$ | $CH_3$ | $CH_3$ | $CH_3$ | Cl | H | $SO_2$ | 2 |
| 6.345 | H | H | H | H | $CH_3$ | $CH_3$ | Cl | Cl | $SO_2$ | 0 |
| 6.346 | H | H | H | H | $CH_3$ | $CH_3$ | Cl | Cl | $SO_2$ | 2 |
| 6.347 | $CH_3$ | $CH_3$ | H | H | $CH_3$ | $CH_3$ | Cl | Cl | $SO_2$ | 0 |
| 6.348 | $CH_3$ | $CH_3$ | H | H | $CH_3$ | $CH_3$ | Cl | Cl | $SO_2$ | 2 |
| 6.349 | H | H | H | $CH_3$ | $CH_3$ | $CH_3$ | Cl | Cl | $SO_2$ | 0 |
| 6.350 | H | H | H | $CH_3$ | $CH_3$ | $CH_3$ | Cl | Cl | $SO_2$ | 2 |
| 6.351 | H | H | $CH_3$ | $CH_3$ | $CH_3$ | $CH_3$ | Cl | Cl | $SO_2$ | 0 |
| 6.352 | H | H | $CH_3$ | $CH_3$ | $CH_3$ | $CH_3$ | Cl | Cl | $SO_2$ | 2 |
| 6.353 | H | H | H | H | $CH_3$ | $CH_3$ | $CH_3$ | $CH_3$ | $SO_2$ | 0 |
| 6.354 | H | H | H | H | $CH_3$ | $CH_3$ | $CH_3$ | $CH_3$ | $SO_2$ | 2 |
| 6.355 | $CH_3$ | $CH_3$ | H | H | $CH_3$ | $CH_3$ | $CH_3$ | $CH_3$ | $SO_2$ | 0 |
| 6.356 | $CH_3$ | $CH_3$ | H | H | $CH_3$ | $CH_3$ | $CH_3$ | $CH_3$ | $SO_2$ | 2 |
| 6.357 | H | H | H | $CH_3$ | $CH_3$ | $CH_3$ | $CH_3$ | $CH_3$ | $SO_2$ | 0 |
| 6.358 | H | H | H | $CH_3$ | $CH_3$ | $CH_3$ | $CH_3$ | $CH_3$ | $SO_2$ | 2 |
| 6.359 | H | H | $CH_3$ | $CH_3$ | $CH_3$ | $CH_3$ | $CH_3$ | $CH_3$ | $SO_2$ | 0 |
| 6.360 | H | H | $CH_3$ | $CH_3$ | $CH_3$ | $CH_3$ | $CH_3$ | $CH_3$ | $SO_2$ | 2 |

PREPARATION EXAMPLES

A) Preparation Examples for the starting materials and intermediates

1. Ethyl 3-(2-bromoethoxy)-2-methylbenzoate 13.6 g (0.2 mol) of sodium methoxide are dissolved in 200 ml of ethanol. 36 g (0.2 mol) of ethyl 3-hydroxy-2-methylbenzoate are then added and the mixture is refluxed for 2 hours. 61.4 g (0.32 mol) of 1,2-dibromoethane are then added dropwise and the mixture is heated to reflux for 20 hours. The cooled reaction mixture is concentrated on a rotary evaporator. The residue is taken up with ethyl acetate and washed 3 times with dilute sodium hydroxide solution. The organic phase is dried and the solvent is distilled off. The useful product is purified by column chromatography.
Yield: 14.6 g of oil NMR(270 MHZ; CDCl$_3$; δ in ppm): 7.4 (d, 1H), 7.2 (tr, 1H), 6.9 (d, 1H), 4.4 (tr, 2H), 4.3 (q, 2H), 3.7 (tr, 2H), 2.4 (s, 3H), 1.5 (tr, 3H)

2. Ethyl 3-(2-methylsulfonylthioethoxy)-2-methylbenzoate 2 g (7 mmol) of ethyl 3-(2-bromoethoxy)-2-methylbenzoate and 1.1 g (7.3 mmol) of potassium thiomethanesulfonate are dissolved in 10 ml of abs. ethanol. The reaction mixture is refluxed for 20 hours. The solvent is then distilled off and the residue is taken up in methylene chloride and washed with water. The organic phase is dried over sodium sulfate and the solvent is removed. The useful product is purified by column chromatography.
Yield 1.1 g (50%)

NMR(270 MHZ; CDCl$_3$; δ in ppm): 7.4 (d, 1H), 7.2 (tr, 1H), 7.0 (d, 1H), 4.5 (tr, 2H), 4.3 (q, 2H), 3.6 (tr, 2H), 3.4 (s, 3H), 2.4 (s, 3H), 1.4 (tr, 3H)

3. Ethyl 8-methyl-2,3-dihydrobenz-1,4-oxathiin-7-carboxylate 1.0 g (3.4 mmol) of ethyl 3-(2-methylsulfonylthioethoxy)-2-methylbenzoate are dissolved in 5 ml of nitromethane. 0.42 g (3.14 mmol) of aluminum trichloride is added. The mixture is stirred at room temperature for 45 min. Working-up is carried out by addition of 10 ml of 2N hydrochloric acid and subsequent extraction with MTB ether. The combined organic phases are washed with water and sodium carbonate solution, dried over sodium sulfate and the solvent is distilled off.

Yield: 0.7 g (93%)

NMR(270 MHZ; CDCl$_3$; δ in ppm): 7.5 (d, 1H), 6.9 (d, 1H), 4.5 (tr, 2H), 4.3 (q, 2H), 3.2 (tr, 2H), 2.4 (s, 3H), 1.4 (tr, 3H), 4. 8-Methyl-2,3-dihydrobenz-1,4-oxathiin-7-carboxylic acid 4.0 g (0.0168 mol) of ethyl 8-methyl-2,3-dihydrobenz-1,4-oxathiin-7-carboxylate are heated to reflux together with 1.0 g (0.0252 mol) of sodium hydroxide in 40 ml of methanol/water. The mixture is stirred for 2 hours at the room temperature and the solvent is then distilled off. The residue is taken up with water. The mixture is extracted with ether and the aqueous phase is then acidified with 2N hydrochloric acid. The useful product precipitates, is filtered off with suction and washed with a little water. The product is dried in a vacuum drying oven at 40° C.

Yield: 2.9 g (82%)

NMR(270 MHZ; d$^6$-DMSO; δ in ppm): 12.3 (bs, 1H), 7.3 (d, 1H) 6.9 (d, 1H), 4.4 (tr, 2H), 3.2 (tr, 2H), 2.4 (s, 3H), 5. 8-Methyl-2,3-dihydro-4,4-dioxobenz-1,4-oxythiin-7-carboxylic acid 2.8 g (0.013 mol) of 8-methyl-2,3-dihydrobenz-1,4-oxathiin-7-carboxylic acid are initially introduced together with a spatula tipful of sodium tungstate in 30 ml of acetic acid.

The mixture is heated to 50° C. 3.3 g (0.029 mol) of hydrogen peroxide (30% strength) are added dropwise. The reaction solution is kept at 50–60° C. for a further 4 hours. The solution is added to ice-water. The precipitate is filtered off with suction, washed with water and dried in a vacuum drying oven at 40° C.

Yield: 2.7 g

Melting point: 234° C.

TABLE 7

III

| No. | T | R$^1$ | R$^2$ | R$^3$ | R$^4$ | X | M | L | n | Phys. data |
|---|---|---|---|---|---|---|---|---|---|---|
| 7.1 | OC$_2$H$_5$ | H | H | H | H | O | CH$_3$ | H | 0 | 1H-NMR(270 MHz; CDCl$_3$; in ppm): 7.5 (d, 1H), 6.9(d, 1H), 4.5(tr, 2H), 4.3(q, 2H), 3.2(tr, 2H), 2.4 (s, 3H), 1.4(tr, 3H) |
| 7.2 | HO | H | H | H | H | O | CH$_3$ | H | 0 | 1H-NMR(270 MHz; d$^6$-DMSO; in ppm): 12.3(bs, 1H), 7.3(d, 1H), 6.9(d, 1H), 4.4 (tr, 2H), 3.2(tr, 2H), 2.4(s, 3H) |
| 7.3 | HO | H | H | H | H | O | CH$_3$ | H | 2 | M.p.[° C.]: 234 |
| 7.4 | OCH$_3$ | H | H | H | H | S | CH$_3$ | H | 0 | M.p.[° C.]: 57 |
| 7.5 | OH | H | H | H | H | S | CH$_3$ | H | 0 | M.p.[° C.]: 179 |
| 7.6 | OH | H | H | H | H | SO$_2$ | CH$_3$ | H | 2 | 1H-NMR(250 MHz, d$^6$-DMSO): 13.8(bs), 8.11(d), 7.98(d), 4.40(m), 2.80(s) |

TABLE 7-continued

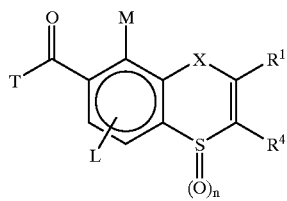

| No. | T | R¹ | R² | R³ | R⁴ | X | M | L | n | Phys. data |
|---|---|---|---|---|---|---|---|---|---|---|
| 7.7 | OC$_2$H$_5$ | H | H | H | H | O | Cl | H | 0 | 1H-NMR(CDCl$_3$): 7.3(2x d), 4.4(q), 4.5(tr), 3.2(tr), 1.4 (tr) |
| 7.8 | OH | H | H | H | H | O | Cl | H | 0 | M.p.[° C.]: 209° C. |
| 7.9 | OH | H | H | H | H | O | Cl | H | 2 | M.p.[° C.]: 225 |

TABLE 8

| No. | T | R¹ | R⁴ | X | M | L | n | Phys. data |
|---|---|---|---|---|---|---|---|---|
| 8.1 | OC$_2$H$_5$ | H | H | O | CH$_3$ | H | 0 | 1H-NMR(270 MHz; CDCl$_3$: 7.44(d), 6.85(d), 6.50(d), 5.25(d), 4.32(q), 2.36(s), 1.36(tr) |
| 8.2 | OH | H | H | O | CH$_3$ | H | 0 | M.p.[° C.]: 174 |
| 8.3 | OH | H | H | O | CH$_3$ | H | 2 | M.p.[° C.]: 205 |
| 8.4 | OC$_2$H$_5$ | H | H | O | Cl | H | 0 | M.p.[° C.]: 92 |
| 8.5 | OH | H | H | O | Cl | H | 0 | M.p.[° C.]: 201 |

Preparation of the final products 1. 2-(8-Methyl-2,3-dihydro-4,4-dioxobenz-1,4-oxathiin-7-carbonyl)-1,3-cyclohexanedione 0.9 g (3.72 mmol) of 8-methyl-2,3-dihydro-4,4-dioxobenz-1,4-oxathiin-7-carboxylic acid and 0.42 g (3.72 mmol) of 1,3-cyclohexadione are dissolved in 20 ml of acetonitrile. 0.81 g (3.9 mmol) of DCC (dicyclohexylcarbodiimide) is then added and the mixture is stirred for several hours until it has reacted completely. 0.75 g (7.44 mmol) of triethylamine and 0.2 ml of trimethylsilyl cyanide are then added dropwise. The mixture is stirred at RT for 3 hours. For working-up, the reaction mixture is poured into 100 ml of 2% strength sodium carbonate solution. The precipitate is filtered off with suction and the aqueous phase is washed with ethyl acetate. The aqueous phase is then acidified with 2N hydrochloric acid. The useful product precipitates. It is filtered off with suction, washed with water and dried in a vacuum drying oven.

Yield: 0.6 g

Melting point: 201° C.

TABLE 9

[Chemical structure with substituents $R^1$ through $R^8$, OH, O, M, X, L, $(O)_n$, and S]

| No. | $R^1$ | $R^2$ | $R^3$ | $R^4$ | $R^5$ | $R^6$ | $R^7$ | $R^8$ | X | M | L | n | Phys. data |
|---|---|---|---|---|---|---|---|---|---|---|---|---|---|
| 9.1 | H | H | H | H | H | H | H | H | O | CH₃ | H | 2 | M.p.[° C.]: 201 |
| 9.2 | H | H | H | H | H | H | CH₃ | CH₃ | O | CH₃ | H | 2 | M.p.[° C.]: 177 |
| 9.3 | H | H | H | H | H | H | H | H | O | CH₃ | H | 0 | M.p.[° C.]: 110 |
| 9.4 | H | H | H | H | H | H | CH₃ | CH₃ | O | CH₃ | H | 0 | M.p.[° C.]: 114 |
| 9.5 | H | H | H | H | CH₃ | CH₃ | H | H | O | CH₃ | H | 0 | M.p.[° C.]: 78 |
| 9.6 | H | H | H | H | H | H | H | H | SO₂ | CH₃ | H | 2 | M.p.[° C.]: 239 |
| 9.7 | H | H | H | H | H | H | CH₃ | H | SO₂ | CH₃ | H | 2 | M.p.[° C.]: 207 |
| 9.8 | H | H | H | H | H | H | CH₃ | CH₃ | SO₂ | CH₃ | H | 2 | M.p.[° C.]: 243 |
| 9.9 | H | H | H | H | CH₃ | CH₃ | H | H | SO₂ | CH₃ | H | 2 | M.p.[° C.]: 147 |
| 9.10 | H | H | H | H | H | H | H | H | S | CH₃ | H | 0 | M.p.[° C.]: 128 |
| 9.11 | H | H | H | H | H | H | CH₃ | CH₃ | S | CH₃ | H | 0 | M.p.[° C.]: 54 |
| 9.12 | H | H | H | H | CH₃ | CH₃ | H | H | S | CH₃ | H | 0 | M.p.[° C.]: 63 |
| 9.13 | H | H | H | H | H | H | H | H | O | Cl | H | 0 | M.p.[° C.]: 135 |
| 9.14 | H | H | H | H | H | H | CH₃ | CH₃ | O | Cl | H | 0 | M.p.[° C.]: 66 |

TABLE 10

[Chemical structure with substituents $R^5$, $R^6$, $R^7$, $R^8$, OH, O, M, X, $R^1$, $R^4$, S, L, $(O)_n$]

| No. | $R^5$ | $R^6$ | $R^7$ | $R^8$ | $R^1$ | $R^4$ | X | M | L | n | Phys. data |
|---|---|---|---|---|---|---|---|---|---|---|---|
| 10.1 | H | H | H | H | H | H | O | CH₃ | H | 0 | M.p.[° C.]: 94 |
| 10.2 | H | H | CH₃ | CH₃ | H | H | O | CH₃ | H | 0 | 1H-NMR(270 MHz, CDCl₃): 17.6(bs), 6.71 (m), 6.46(d), 5.23(d), 2.65(s), 2.33(s), 2.03(s), 1.12(s) |
| 10.3 | CH₃ | CH₃ | H | H | H | H | O | CH₃ | H | 0 | 1H-NMR(270 MHz, CDCl₃, isomer mixture): 17,45(g), 6.78(d), 6.68 (d), 6.47(d), 5.21(d), 2.80(m), 1.99(s), 1.89 (m), 1.18(s) and |

TABLE 10-continued

[Structure: cyclohexanedione with $R^5, R^6, R^7, R^8$ substituents connected via C(=O) to a benzene ring with M, L substituents, fused to ring containing X, $R^1$, $R^4$, S(=O)$_n$]

| No. | $R^5$ | $R^6$ | $R^7$ | $R^8$ | $R^1$ | $R^4$ | X | M | L | n | Phys. data |
|---|---|---|---|---|---|---|---|---|---|---|---|
| | | | | | | | | | | | 18.0(s), 6.78(d), 6.68 (d), 6.48(d), 5.22(d), 2.47(m), 2.21(s), 1.89 (m), 1.38(s) |
| 10.4 | H | H | H | H | H | H | O | CH$_3$ | H | 2 | M.p.[° C.]: 245 |
| 10.5 | H | H | CH$_3$ | CH$_3$ | H | H | O | CH$_3$ | H | 2 | M.p.[° C.]: 216 |
| 10.6 | CH$_3$ | CH$_3$ | H | H | H | H | O | CH$_3$ | H | 2 | M.p.[° C.]: 107 |
| 10.7 | H | H | H | H | H | H | O | Cl | H | 0 | M.p.[° C.]: 108 |
| 10.8 | H | H | CH$_3$ | CH$_3$ | H | H | O | Cl | H | 0 | M.p.[° C.]: 56 |

The compounds I and their agriculturally utilizable salts are suitable, both as isomer mixtures and in the form of the pure isomers, as herbicides. The herbicidal compositions comprising I control plant growth on uncultivated areas very well, particularly at high application rates. In crops such as wheat, rice, maize, soybeans and cotton, they act against broad-leaved weeds and grass weeds without noticeably damaging the crop plants. This effect occurs especially at low application rates.

Depending on the particular application method, the compounds I or compositions containing them can additionally be employed for eliminating undesired plants in a further number of crop plants. Suitable crops are, for example, the following:

*Allium cepa, Ananas comosus, Arachis hypogaea, Asparagus officinalis, Beta vulgaris* spp. *altissima, Beta vulagris* spp. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spp., *Manihot esculenta, Medicago sativa, Musa* spp., *Nicotiana tabacum (N.rustica), Olea europaea, Oryza sativa, Phaseolus lunatus, Phaseolus vulgaris, Picea abies,* Pinus spp., *Pisum sativum, Prunus avium, Prunus persica, Pyrus communis, Ribes sylestre* [sic], *Ricinus communis, Saccharum officinarum, Secale cereale, Solanum tuberosum, Sorghum bicolor (s. vulgare), Theobroma cacao, Trifolium pratense, Triticum aestivum, Triticum durum, Vicia faba, Vitis vinifera, Zea mays.*

Moreover, the compounds I can also be used in crops which as a result of breeding, including genetic engineering methods, are tolerant to the action of herbicides.

The application of the herbicidal compositions or of the active compounds can be carried out pre-emergence or post-emergence. If the active substances are less tolerable for certain crop plants, application techniques can be used in which the herbicidal compositions are sprayed with the aid of spray equipment such that the leaves of the sensitive crop plants are not affected if possible, while the active compounds reach the leaves of undesired plants growing under them or the uncovered soil surface (post-directed, lay-by).

The compounds I or the herbicidal compositions comprising them an be used, for example, in the form of directly sprayable aqueous solutions, powders, suspensions, even high-percentage aqueous, oily or other suspensions or dispersions, emulsions, oil dispersions, pastes, dusting compositions, broadcasting compositions or granules, by spraying, atomizing, dusting, broadcasting or watering. The application forms depend on the intended uses; they should in each case if possible guarantee the finest dispersion of the active compounds according to the invention.

Suitable inert additives are essentially: mineral oil fractions of medium to high boiling point, such as kerosene or diesel oil, also coal tar oils and oils of vegetable or animal origin, aliphatic, cyclic and aromatic hydrocarbons, eg. paraffin, tetrahydronaphthalene, alkylated naphthalenes or their derivatives, alkylated benzenes or their derivatives, alcohols such as methanol, ethanol, propanol, butanol, cyclohexanol, ketones such as cyclohexanone or strongly polar solvents, eg. amines such as N-methylpyrrolidone or water.

Aqueous application forms can be prepared from emulsion concentrates, suspensions, pastes, wettable powders or water-dispersible granules by addition of water. To prepare emulsions, pastes or oil dispersions, the substrates [sic], as such or dissolved in an oil or solvent, can be homogenized in water by means of wetting agents, adherents, dispersants or emulsifiers. However, concentrates consisting of active substance, wetting agent, adherent, dispersant or emulsifier and possibly solvent or oil can also be prepared, which are suitable for dilution with water.

Suitable surface-active substances (adjuvants) are the alkali metal, alkaline earth metal and ammonium salts of aromatic sulfonic acids, eg. lignosulfonic, phenolsulfonic, naphthalenesulfonic and dibutylnaphthalenesulfonic acid, and also of fatty acids, alkyl- and alkylarylsulfonates, alkyl, lauryl ether and fatty alcohol sulfates, as well as salts of sulfated hexa-, hepta- and octadecanols and also of fatty alcohol glycol ethers, condensation products of sulfonated naphthalene and its derivatives with formaldehyde, condensation products of naphthalene or of the naphthalenesulfonic acids with phenol and formaldehyde, polyoxyethylene octylphenol ethers, ethoxylated isooctyl-, octyl- or nonylphenol, alkylphenyl and tributylphenyl polyglycol ethers, alkylaryl polyether alcohols, isotridecyl alcohol, fatty alcohol-ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powder, broadcasting and dusting compositions can be prepared by mixing or joint grinding of the active substances with a solid carrier.

Granules, eg. coated, impregnated and homogeneous granules, can be prepared by binding the active compounds to solid carriers. Solid carriers are mineral earths such as silicic acids, silica gels, silicates, talc, kaolin, limestone, lime, chalk, bole, loess, clay, dolomite, diatomaceous earth, calcium and magnesium sulfate, magnesium oxide, ground synthetic materials, fertilizers, such as ammonium sulfate, ammonium phosphate, ammonium nitrate, ureas and vegetable products such as cereal flour, tree bark, wood and nutshell meal, cellulose powder or other solid carriers.

The concentrations of the active compounds I in the ready-to-use preparations can be varied within wide ranges. The formulations in general contain from 0.001 to 98% by weight, preferably 0.01 to 95% by weight, of active compound. The active compounds are employed here in a purity of from 90% to 100%, preferably 95% to 100% (according to NMR spectrum).

The compounds I according to the invention can be formulated, for example, as follows:

I. 20 parts by weight of the compound No. 9.1 are dissolved in a mixture which consists of 80 parts by weight of alkylated benzene, 10 parts by weight of the addition product of 8 to mol of ethylene oxide to 1 mol of oleic acid-N-monoethanolamide, 5 parts by weight of calcium salt of dodecylbenzenesulfonic acid and 5 parts by weight of the addition product of 40 mol of ethylene oxide to 1 mol of castor oil. By pouring out the solution and finely dispersing it in 100,000 parts by weight of water, an aqueous dispersion is obtained which contains 0.02% by weight of the active compound.

II. 20 parts by weight of the compound No. 9.1 are dissolved in a mixture which consists of 40 parts by weight of cyclohexanone, 30 parts by weight of isobutanol, 20 parts by weight of the addition product of 40 mol of isooctylphenol and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

III. 20 parts by weight of the active compound No. 9.1 are dissolved in a mixture which consists of 25 parts by weight of cyclohexanone, 65 parts by weight of a mineral oil fraction of boiling point 210 to 280° C. and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

IV. 20 parts by weight of the active compound No. 9.1 are well mixed with 3 parts by weight of the sodium salt of diisobutylnaphthalenesulfonic acid, 17 parts by weight of the sodium salt of a lignosulfonic acid from a sulfite waste liquor and 60 parts by weight of powdered silica gel and ground in a hammer mill. By finely dispersing the mixture in 20,000 parts by weight of water, a spray mixture is obtained which contains 0.1% by weight of the active compound.

V. 3 parts by weight of the active compound No. 9.1 are mixed with 97 parts by weight of finely divided kaolin. In this manner a broadcasting composition is obtained which contains 3% by weight of the active compound.

VI. 20 parts by weight of the active compound No. 9.1 are intimately mixed with 2 parts by weight of calcium salt of dodecylbenzenesulfonic acid, 8 parts by weight of fatty alcohol polyglycol ether, 2 parts by weight of sodium salt of a phenol-urea-formaldehyde condensate and 68 parts by weight of a paraffinic mineral oil. A stable oily dispersion is obtained.

VII. 1 part by weight of the compound 9.1 is dissolved in a mixture which consists of 70 parts by weight of cyclohexanone, 20 parts by weight of ethoxylated isooctylphenol and 10 parts by weight of ethoxylated castor oil. A stable emulsion concentrate is obtained.

VIII. 1 part by weight of the compound 9.1 is dissolved in a mixture which consists of 80 parts by weight of cyclohexanone and 20 parts by weight of Emulphor EL (ethoxylated caster caster oil). A stable emulsion concentrate is obtained.

To widen the spectrum of action and to achieve synergistic effects, the 2-hetaroylcyclohexane-1,3-diones I can be mixed with numerous representatives of other herbicidal or growth-regulating active compound groups and applied together. For example, suitable mixing components are 1,2,4-thiadiazoles, 1,3,4-thiadiazoles, amides, aminophosphoric acid and its derivatives, aminotriazoles, anilides, (het)aryloxyalkanoic acid and its derivatives, benzoic acid and its derivatives, benzothiadiazinones, 2-aroyl-1,3-cyclohexanediones, hetaryl aryl ketones, benzylisoxazolidinones, meta-CF3-phenyl derivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and heteroaryloxyphenoxypropionic acid esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

Additionally, it may be useful to apply the compounds I on their own or together in combination with other herbicides, also additionally mixed with further crop protection compositions, for example with compositions for controlling pests or phytopathogenic fungi or bacteria. Furthermore of interest is the miscibility with mineral salt solutions, which are employed for the elimination of nutritional and trace element deficiencies. Nonphytotoxic oils and oil concentrates can also be added.

The application rates of active compound are, depending on the control target, time of year, target plants and stage of growth, from 0.001 to 3.0, preferably 0.01 to 1.0, kg/ha of active substance (a.s.)

Use Examples

It was possible to show the herbicidal action of the 2-hetaroylcyclohexane-1,3-diones of the formula I by greenhouse tests:

The culture vessels used were plastic flowerpots containing loamy sand with about 3.0% humus as a substrate. The seeds of the test plants were sown separately according to species.

In the case of pre-emergence treatment, the active compounds suspended or emulsified in water were applied directly after sowing by means of finely dispersing nozzles. The containers were lightly watered in order to promote germination and growth, and then covered with transparent plastic hoods until the plants had taken root. This covering causes a uniform germination of the test plants, if this has not been adversely affected by the active compounds. The application rate for pre-emergence treatment was 0.0625 or 0.0313 kg/ha of a.s.

For the purpose of post-emergence treatment, the test plants, depending on growth form, are first raised to a growth height of from 3 to 15 cm and only then treated with the active compounds suspended or emulsified in water. For this, the test plants are either sown directly and grown in the same containers or they are first raised separately as seedlings and transplanted into the test containers a few days before treatment.

The plants were kept species-specifically at from 10–25° C. or 20–35° C. The test period extended over 2 to 4 weeks. During this time, the plants were tended, and their reaction to the individual treatments was evaluated.

Assessment was carried out on a scale from 0 to 100. 100 here means no emergence of the plants or complete destruction of at least the above-ground parts and 0 means no damage or normal course of growth.

The plants used in the greenhouse tests were made up of the following species:

| Botanical Name | Common Name |
| --- | --- |
| Chenopodium album (CHEAL) | lamb's-quarters (gossefoot [sic]) |
| Echinochloa crus-galli (ECHCG) | barnyard grass |
| Solanum nigrum (SOLNI) | black nightshade |
| Triticum aestivum (TRZAW) | winter wheat |
| Zea mays (ZEAMX) | Indian corn |

TABLE 11

Selective herbicidal activity on post-emergence use in a greenhouse

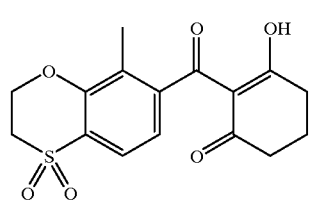

| Ex. No. 9.1 Application rate (kg/ha of a.s.) | 0.0625 | 0.0313 |
| --- | --- | --- |
| Test plants | Damage in % | |
| TRZAW | 0 | 0 |
| ZEAMX | 15 | 0 |
| ECHCG | 90 | 90 |
| CHEAL | 95 | 95 |
| SOLNI | 90 | 85 |

We claim:
1. A hetaroyl derivative of the formula I

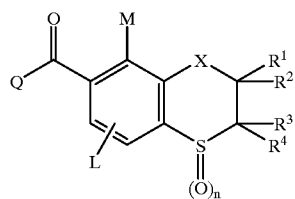

where the substituents have the following meanings:

L and M hydrogen, $C_1$–$C_6$-alkyl, $C_2$–$C_6$-alkenyl, $C_2$–$C_6$-alkynyl, $C_1$–$C_4$-alkoxy, it being possible for these groups to be unsubstituted or substituted by one to five halogen atoms or $C_1$–$C_4$-alkoxy; halogen, cyano, nitro;

X oxygen or sulfur which can be substituted by one or two oxygens;

n zero, one, two;

$R^1$ hydrogen, $C_1$–$C_6$-alkyl, $C_2$–$C_6$-alkenyl, $C_2$–$C_6$-alkynyl, $C_1$–$C_4$-alkoxy, it being possible for these groups to be unsubstituted or substituted by one to five halogen atoms or $C_1$–$C_4$-alkoxy; halogen;

phenyl which can be monosubstituted or polysubstituted by the following groups: $C_1$–$C_4$-alkyl, hydrogen, $C_1$–$C_4$-alkoxy, $C_1$–$C_4$-haloalkyl, $C_1$–$C_4$-haloalkoxy, halogen, nitro, cyano, $C_1$–$C_4$-alkyloxycarbonyl;

$R^2$ hydrogen, $C_1$–$C_6$-alkyl, $C_2$–$C_6$-alkenyl, $C_2$–$C_6$-alkynyl, $C_1$–$C_4$-alkoxy, it being possible for these groups to be unsubstituted or substituted by one to five halogen atoms or $C_1$–$C_4$-alkoxy; halogen;

phenyl which can be monosubstituted or polysubstituted by the following groups: $C_1$–$C_4$-alkyl, hydrogen, $C_1$–$C_4$-alkoxy, $C_1$–$C_4$-haloalkyl, $C_1$–$C_4$-haloalkoxy, halogen, nitro, cyano, $C_1$–$C_4$-alkyloxycarbonyl; $R^3$ and $R^2$ can form a bond;

$R^3$ hydrogen, $C_1$–$C_6$-alkyl, $C_2$–$C_6$-alkenyl, $C_2$–$C_6$-alkynyl, $C_1$–$C_4$-alkoxy, it being possible for these groups to be unsubstituted or substituted by one to five halogen atoms or $C_1$–$C_4$-alkoxy; halogen;

phenyl which can be monosubstituted or polysubstituted by the following groups:

$C_1$–$C_4$-alkyl, hydrogen, $C_1$–$C_4$-alkoxy, $C_1$–$C_4$-haloalkyl, $C_1$–$C_4$-haloalkoxy, halogen, nitro, cyano, $C_1$–$C_4$-alkyloxycarbonyl; $R^3$ and $R^2$ can form a bond;

$R^4$ hydrogen, $C_1$–$C_6$-alkyl, $C_2$–$C_6$-alkenyl, $C_2$–$C_6$-alkynyl, $C_1$–$C_4$-alkoxy, it being possible for these groups to be unsubstituted or substituted by one to five halogen atoms or $C_1$–$C_4$-alkoxy; halogen;

phenyl which can be monosubstituted or polysubstituted by the following groups: $C_1$–$C_4$-alkyl, hydrogen, $C_1$–$C_4$-alkoxy, $C_1$–$C_4$-haloalkyl, $C_1$–$C_4$-haloalkoxy, halogen, nitro, cyano, $C_1$–$C_4$-alkyloxycarbonyl;

Q a cyclohexane-1,3-dione ring, linked in the 2-position, of the formula II

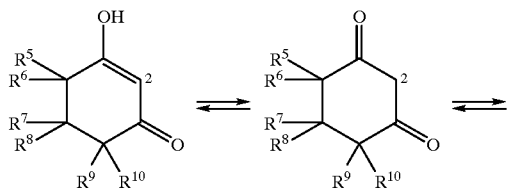
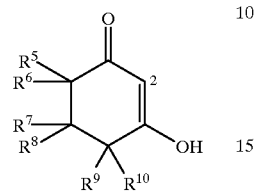
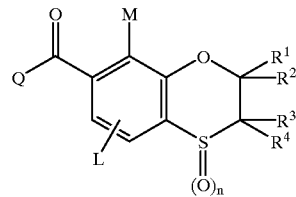

where the substituents have the following meanings:
$R^5$, $R^6$ and $R^{10}$ hydrogen, $C_1$–$C_4$-alkyl;
$R^7$ hydrogen, $C_1$–$C_4$-alkyl, $C_3$–$C_4$-cycloalkyl, it being possible for these groups, if desired, to carry one to three of the following substituents: halogen, $C_1$–$C_4$-thioalkyl or $C_1$–$C_4$-alkoxy; or
$R^7$ $C_1$–$C_4$-alkoxy; $C_1$–$C_6$-alkoxyalkyl, tetrahydropyran-3-yl, tetrahydropyran-4-yl; or
$R^7$ and $R^9$ can together form a bond or a three- to six-membered carbocyclic ring;
$R^8$ hydrogen, $C_1$–$C_4$-alkyl;
$R^9$ hydrogen, $C_1$–$C_4$-alkyl or a group $COOR^{11}$;
$R^{11}$ $C_1$–$C_4$-alkyl;
or agriculturally utilizable salts.

2. A hetaroyl derivative of the formula Ia

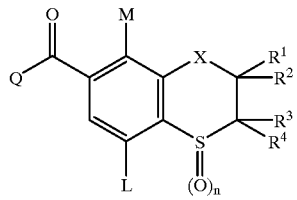

where L is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, cyano or nitro and M is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, cyano or nitro and Q, X, $R_1$ to $R_4$ and n have the meanings given in claim 1.

3. A hetaroyl derivative of the formula Ib

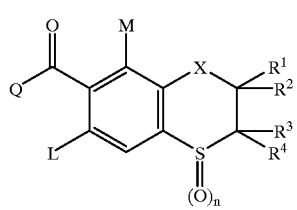

where L is $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, cyano or nitro and M is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, cyano or nitro and Q, X, $R_1$ to $R_4$ and n have the meanings given in claim 1.

4. A hetaroyl derivative of the formula I as defined in claim 1 where the radicals L and M are hydrogen, methyl, methoxy, chlorine, cyano, nitro and trifluoromethyl.

5. A hetaroyl derivative of the formula Ic

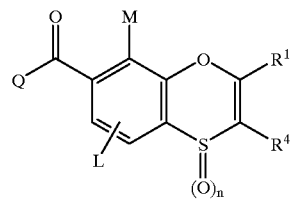

where L is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, cyano or nitro and M is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, cyano or nitro and Q, $R_1$ to $R_4$ and n have the meanings given in claim 1.

6. A hetaroyl derivative of the formula Id

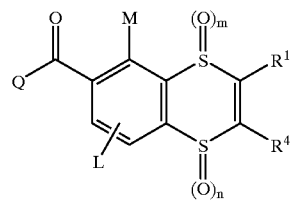

where L is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, cyano or nitro and M is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, cyano or nitro and Q, $R_1$, $R_4$ and n have the meanings given in claim 1.

7. A hetaroyl derivative of the formula Ie

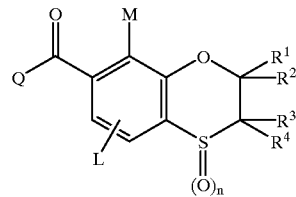

where L is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, cyano or nitro and M is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, cyano or nitro, and m is zero, one or two and Q, $R_1$, $R_4$ and n have the meanings given in claim 1.

8. A hetaroyl derivative of the formula If

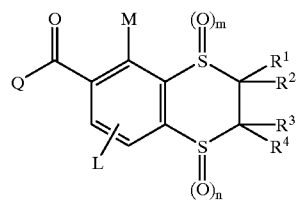

If where L is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, cyano or nitro and M is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, cyano or nitro, and m is zero, one or two and Q, $R_1$ to $R_4$ and n have the meanings given in claim 1.

9. A process for preparing the compound of the formula I as defined in claim 1, which comprises acylating the respective starting substances of the formula II

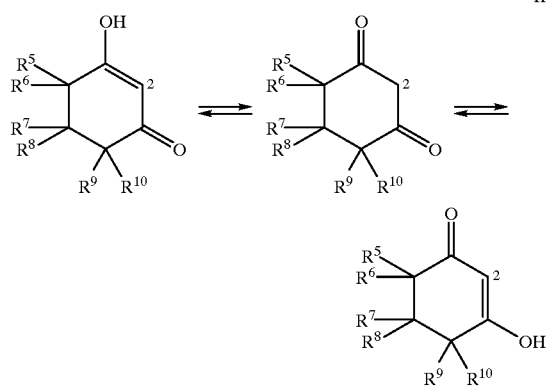

II using an acid chloride of the formula IIIa or an acid of the formula IIIb

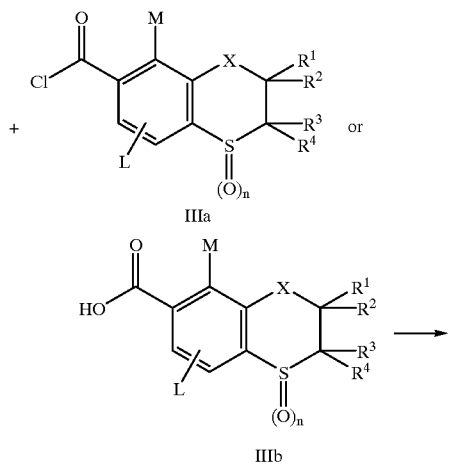

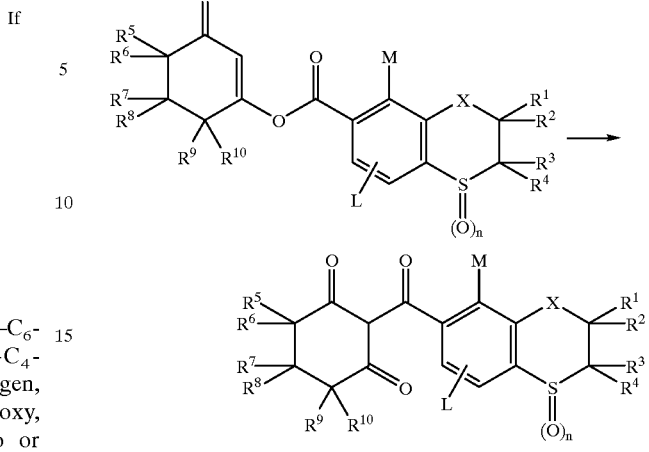

where L, M, X, $R^1$ to $R^4$ and n have the meanings mentioned in claim 1, and rearranging the acylation product to the compounds I in the presence of a catalyst.

10. A hetaroyl derivative of the formula IIIc

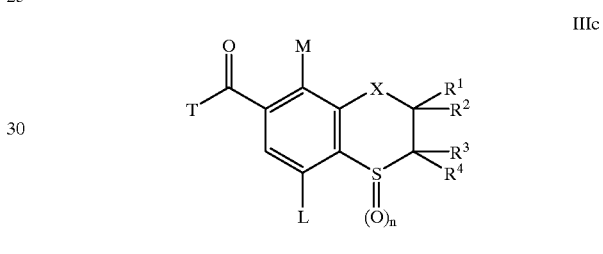

IIIc where T, L, M, X, $R^1$ to $R^4$ and n have the following meanings:
T chlorine, OH or $C_1$–$C_4$-alkoxy;
L hydrogen, $C_1$–$C_6$-alkyl, $C_2$–$C_6$-alkenyl, $C_2$–$C_6$-alkynyl, $C_1$–$C_4$-alkoxy, it being possible for these groups to be unsubstituted or substituted by one to five halogen atoms or $C_1$–$C_4$-alkoxy; halogen, cyano, nitro;
M hydrogen, $C_1$–$C_6$-alkyl, $C_2$–$C_6$-alkenyl, $C_2$–$C_6$-alkynyl, $C_1$–$C_4$-alkoxy, it being possible for these groups to be unsubstituted or substituted by one to five halogen atoms or $C_1$–$C_4$-alkoxy; halogen, cyano, nitro;
X, $R^1$, $R^2$, $R^3$, $R^4$ and n are as given in claim 1.

11. A hetaroyl derivative of the formula IIId

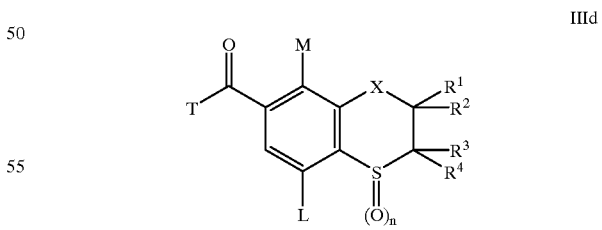

IIId where T, L, M, X, $R^1$ to $R^4$ and n have the following meanings:
T chlorine, OH or $C_1$–$C_4$-alkoxy;
L $C_1$–$C_6$-alkyl, $C_2$–$C_6$-alkenyl, $C_2$–$C_6$-alkynyl, $C_1$–$C_4$-alkoxy, it being possible for these groups to be unsubstituted or substituted by one to five halogen atoms or $C_1$–$C_4$-alkoxy; halogen, cyano, nitro;
M hydrogen, $C_1$–$C_6$-alkyl, $C_2$–$C_6$-alkenyl, $C_2$–$C_6$-alkynyl, $C_1$–$C_4$-alkoxy, it being possible for these groups to be unsubstituted or substituted by one to five halogen atoms or $C_1$–$C_4$-alkoxy; halogen, cyano, nitro;

X, $R^1$, $R^2$, $R^3$, $R^4$ and n are as given in claim 1.

12. A herbicidal composition, comprising at least one hetaroyl derivative of the formula I as defined in claim 1 and additives.

13. A method of controlling undesired plant growth, which comprises allowing a herbicidally active amount of a hetaroyl derivative of the formula I as defined in claim 1 to act on the plants or their habitat.

* * * * *